US012295669B2

(12) United States Patent
Mariappan et al.

(10) Patent No.: US 12,295,669 B2
(45) Date of Patent: May 13, 2025

(54) SYSTEMS AND METHODS FOR PERFORMING LOCALIZATION WITHIN A BODY

(71) Applicant: Acutus Medical, Inc., Carlsbad, CA (US)

(72) Inventors: Leo Mariappan, Oceanside, CA (US); Wesley D. Jones, Oceanside, CA (US); Marcus Frederick Julian, Vista, CA (US); Daniel Welsh, Encinitas, CA (US); Ragnar Olafsson, San Diego, CA (US); Steven Anthony Yon, San Diego, CA (US); Derrick Ren-Yu Chou, San Diego, CA (US); Michael C. Oliveira, San Marcos, CA (US); Jun Song, San Diego, CA (US); Ahmad Falahatpisheh, San Marcos, CA (US); Timothy J. Corvi, San Diego, CA (US); Graydon Ernest Beatty, Carlsbad, CA (US); Alexander J. Asconeguy, Murrieta, CA (US); Hongping Dai, Vista, CA (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 312 days.

(21) Appl. No.: 17/613,249

(22) PCT Filed: Jun. 4, 2020

(86) PCT No.: PCT/US2020/036110
§ 371 (c)(1),
(2) Date: Nov. 22, 2021

(87) PCT Pub. No.: WO2020/247619
PCT Pub. Date: Dec. 10, 2020

(65) Prior Publication Data
US 2022/0226046 A1 Jul. 21, 2022

Related U.S. Application Data

(60) Provisional application No. 62/857,055, filed on Jun. 4, 2019.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 5/063* (2013.01);
(Continued)

(58) Field of Classification Search
CPC ...... A61B 18/1492; A61B 2018/00577; A61B 2018/00839; A61B 2018/00875;
(Continued)

(56) References Cited

U.S. PATENT DOCUMENTS

| 4,173,228 A | 11/1979 | Van Steenwyk et al. |
| 4,841,977 A | 6/1989 | Griffith et al. |

(Continued)

FOREIGN PATENT DOCUMENTS

| CA | 2825736 | 5/2008 |
| CA | 2829626 | 9/2012 |

(Continued)

OTHER PUBLICATIONS

Leif et al., "Geometric modeling based on polygonal meshes". Eurographics 2000 Tutorial, Aug. 21, 2000.
(Continued)

*Primary Examiner* — Mark D Remaly
(74) *Attorney, Agent, or Firm* — Onello & Mello, LLP

(57) ABSTRACT

Provided herein are systems and methods for performing localization within a patient. A method of localization within a body comprises providing at least one processor coupled to at least one data storage device, establishing and calibrating a localization coordinate system within a body by executing a first localization mode by the at least one processor, recalibrating the localization coordinate system by executing a second localization mode by the at least one processor, and localizing a device within the localization coordinate system using the first localization mode and the second localization mode, by the at least one processor. The first localization mode can be an impedance-based localiza-
(Continued)

tion mode and the second localization mode can be magnetic-based localization mode, or vice versa.

25 Claims, 11 Drawing Sheets

(51) Int. Cl.
*A61B 18/14* (2006.01)
*A61B 18/00* (2006.01)
*A61B 90/00* (2016.01)

(52) U.S. Cl.
CPC .............. *A61B 18/1492* (2013.01); *A61B 2018/00577* (2013.01); *A61B 2018/00839* (2013.01); *A61B 2018/00875* (2013.01); *A61B 2034/2048* (2016.02); *A61B 2034/2051* (2016.02); *A61B 2034/2053* (2016.02); *A61B 2034/2063* (2016.02); *A61B 2034/2072* (2016.02); *A61B 2090/0818* (2016.02); *A61B 2090/3925* (2016.02); *A61B 2090/3929* (2016.02); *A61B 2090/3954* (2016.02); *A61B 2090/3966* (2016.02); *A61B 2090/397* (2016.02)

(58) Field of Classification Search
CPC .... A61B 2034/2048; A61B 2034/2051; A61B 2034/2053; A61B 2034/2063; A61B 2034/2072; A61B 2090/0818; A61B 2090/3925; A61B 2090/3929; A61B 2090/3954; A61B 2090/3966; A61B 2090/397; A61B 34/20; A61B 5/061; A61B 5/062; A61B 5/063
See application file for complete search history.

(56) References Cited

U.S. PATENT DOCUMENTS

| | | | |
|---|---|---|---|
| 5,041,973 A | 8/1991 | Lebron et al. |
| 5,156,151 A | 10/1992 | Imran |
| 5,293,868 A | 3/1994 | Nardella |
| 5,482,472 A | 1/1996 | Garoni et al. |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesley et al. |
| 5,795,299 A | 8/1998 | Eaton et al. |
| 5,820,568 A | 10/1998 | Willis |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,944,022 A | 8/1999 | Nardella et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 | 2/2001 | Noren et al. |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,556,695 B1 | 4/2003 | Packer et al. |
| 6,574,492 B1 | 6/2003 | Ben-Haim et al. |
| 6,640,119 B1 | 10/2003 | Budd et al. |
| 6,695,785 B2 | 2/2004 | Brisken et al. |
| 6,716,166 B2 | 4/2004 | Govari |
| 6,728,562 B1 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,094 B2 | 10/2007 | Nohara et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,351,914 B2 | 4/2008 | Kaneto et al. |
| 7,479,141 B2 | 1/2009 | Kleen et al. |
| 7,505,810 B2 | 3/2009 | Harlev et al. |
| 7,536,218 B2 | 5/2009 | Govari et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,848,789 B2 | 12/2010 | Govari et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,200,314 B2 | 6/2012 | Bladen et al. |
| 8,208,998 B2 | 6/2012 | Beatty et al. |
| 8,221,411 B2 | 7/2012 | Francischelli et al. |
| 8,233,972 B2 | 7/2012 | Zhang |
| 8,311,613 B2 | 11/2012 | Danehorn |
| 8,320,711 B2 | 11/2012 | Altmann et al. |
| 8,326,419 B2 | 12/2012 | Rosenberg et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,023,027 B2 | 5/2015 | Bar-Tal et al. |
| 9,026,196 B2 | 5/2015 | Curran et al. |

(56) References Cited

U.S. PATENT DOCUMENTS

| | | |
|---|---|---|
| 9,031,642 B2 | 5/2015 | Ghosh |
| 9,037,259 B2 | 5/2015 | Mathur |
| 9,044,245 B2 | 6/2015 | Condie et al. |
| 9,113,807 B2 | 8/2015 | Koyrakh et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,591,990 B2 | 3/2017 | Chen et al. |
| 9,603,651 B2 | 3/2017 | Ghosh |
| 9,610,024 B2 | 4/2017 | Scharf et al. |
| 9,662,033 B2 | 5/2017 | Severino |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,775,578 B2 | 10/2017 | Katz |
| 9,827,039 B2 | 11/2017 | Dandler et al. |
| 9,833,161 B2 | 12/2017 | Govari |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,045,707 B2 | 8/2018 | Govari |
| 10,082,395 B2 | 9/2018 | Koyrakh et al. |
| 10,201,311 B2 | 2/2019 | Chou et al. |
| 10,296,707 B2 | 5/2019 | Passerini et al. |
| 10,405,828 B2 | 9/2019 | Deladi et al. |
| 10,456,056 B2 | 10/2019 | Govari et al. |
| 10,593,234 B2 | 3/2020 | Zhu et al. |
| 10,653,318 B2 | 5/2020 | Welsh et al. |
| 10,856,827 B2 | 12/2020 | Katz |
| 10,945,633 B2 | 3/2021 | Chen et al. |
| 11,006,853 B2 | 5/2021 | Ludwin et al. |
| 11,179,199 B2 | 11/2021 | Everling |
| 11,839,481 B2 | 12/2023 | Severino |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0099292 A1 | 7/2002 | Brisken et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0163046 A1 | 8/2003 | Nohara et al. |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0113498 A1 | 6/2004 | Kroenke |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0221438 A1 | 9/2008 | Chen et al. |
| 2008/0287790 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0203992 A1 | 8/2009 | Govari et al. |
| 2009/0264781 A1 | 10/2009 | Scharf et al. |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0268059 A1 | 10/2010 | Ryu et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0230775 A1 | 9/2011 | Barley et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172702 A1 | 7/2012 | Koyrakh et al. |
| 2012/0172859 A1 | 7/2012 | Condie et al. |
| 2012/0184863 A1 | 7/2012 | Harlev et al. |
| 2012/0265054 A1 | 10/2012 | Olson |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |

(56) References Cited

U.S. PATENT DOCUMENTS

| | | |
|---|---|---|
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0221803 A1 | 8/2014 | Bar-Tal et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0045647 A1 | 2/2015 | Katz |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0294082 A1 | 10/2015 | Passerini et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0183824 A1 | 6/2016 | Severino |
| 2016/0192902 A1 | 7/2016 | Werneth et al. |
| 2016/0228023 A1 | 8/2016 | Govari |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0156595 A1 | 6/2017 | Katz |
| 2017/0172442 A1 | 6/2017 | Govari |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 3/2018 | Scharf et al. |
| 2018/0132938 A1 | 5/2018 | Everling |
| 2018/0146948 A1 | 5/2018 | Chou et al. |
| 2018/0296114 A1 | 10/2018 | Welsh et al. |
| 2018/0315347 A1 | 11/2018 | Zhu et al. |
| 2018/0368716 A1 | 12/2018 | Govari et al. |
| 2019/0125210 A1* | 5/2019 | Govari .................. A61B 5/062 |
| 2019/0159729 A1 | 5/2019 | Chou et al. |
| 2020/0138317 A1 | 5/2020 | Scharf et al. |
| 2020/0187801 A1 | 6/2020 | Scharf et al. |
| 2020/0205686 A1 | 7/2020 | Severino |
| 2021/0068694 A1 | 3/2021 | Chou et al. |

FOREIGN PATENT DOCUMENTS

| | | |
|---|---|---|
| CN | 1856213 | 11/2006 |
| CN | 101048100 | 10/2007 |
| CN | 201223445 | 4/2009 |
| CN | 201275144 | 7/2009 |
| CN | 101657153 | 2/2010 |
| CN | 102770085 | 11/2012 |
| CN | 103687533 | 3/2014 |
| CN | 104462650 | 3/2015 |
| EP | 1166714 | 1/2002 |
| EP | 1415608 | 10/2004 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 08164140 | 6/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003509145 | 3/2003 |
| JP | 2003511098 | 3/2003 |
| JP | 2004350702 | 12/2004 |
| JP | 2005536313 | 12/2005 |
| JP | 2006511296 | 4/2006 |
| JP | 2006525072 | 11/2006 |
| JP | 2007021218 | 2/2007 |
| JP | 2008149132 | 7/2008 |
| JP | 2009135109 | 6/2009 |
| JP | 2009136679 | 6/2009 |
| JP | 2010092446 | 4/2010 |
| JP | 2011504363 | 2/2011 |
| JP | 2011507656 | 3/2011 |
| JP | 2012509701 | 4/2012 |
| JP | 2013188476 | 9/2013 |
| JP | 2014506171 | 3/2014 |
| JP | 2014511737 | 5/2014 |
| JP | 2014514031 | 6/2014 |
| JP | 2014516723 | 7/2014 |
| JP | 2015036124 | 2/2015 |
| JP | 2016511026 | 4/2016 |
| JP | 2016123870 | 7/2016 |
| JP | 2016144642 | 8/2016 |
| JP | 2017047213 | 3/2017 |
| JP | 2017514553 | 6/2017 |
| JP | 2019005572 | 1/2019 |
| WO | 9406349 | 3/1994 |
| WO | 9905971 | 2/1999 |
| WO | 0007501 | 2/2000 |
| WO | 0040166 | 7/2000 |
| WO | 0245608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |

(56) References Cited

FOREIGN PATENT DOCUMENTS

| WO | 2014124231 | 2/2013 |
|---|---|---|
| WO | 2013101257 | 7/2013 |
| WO | 2013123549 | 8/2013 |
| WO | 2014036439 | 3/2014 |
| WO | 20014059308 | 4/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |
| WO | 2017192775 | 11/2017 |
| WO | 2019144103 | 7/2019 |
| WO | 2019217430 | 11/2019 |
| WO | 2020097438 | 5/2020 |

OTHER PUBLICATIONS

Partial European Search Report dated Apr. 29, 2014 issued in corresponding European Application No. 13176658.
Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik—Grundkurs Theoretische Physik 3, Springer Spectrum, p. 89-91.
Extended European Search Report dated Aug. 10, 2021 issued in corresponding European Application No. 19741310.7.
Flavia et al. "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, vol. 16, No. 10 (Oct. 2005) pp. 1071-1076.
European Office Action dated Oct. 4, 2023 issued in European Application No. 20749999.7.
Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Dec. 22, 2019 issued in corresponding Australian Application No. 2018278959.
Australian Office Action dated Feb. 26, 2018 issued in Australian Application No. 2017201560.
Australian Office Action dated Jan. 15, 2020 issued in corresponding Australian Application No. 2016262547.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 16, 2020 issued in corresponding Australian Application No. 2016260522.
Australian Office Action dated Mar. 17, 2018 issued in corresponding Australian Application No. 2013308531.
Australian Office Action dated May 30, 2016 issued in related Australian Application No. 2012225250.
Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22 2015 issued in corresponding Canadian Application No. 2656898.
Canadian Office Action dated Jan. 22, 2018 issued in corresponding Canadian Application No. 2932956.
Canadian Office Action dated Jul. 12, 2019 issued in corresponding Canadian Application No. 2881457.
Canadian Office Action dated Mar. 30, 2017 issued in corresponding Canadian Application No. 2747859.
Canadian Office Action dated May 20, 2020 issued in corresponding Canadian Application No. 2881457.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Chinese Office Action dated Apr. 8, 2020 issued in corresponding Chinese Application No. 201810153436.2.
Chinese Office Action dated Sep. 8, 2021 issued in corresponding Chinese Application No. 201680040709.1.
Communication Under Rule 71(3) EPC dated Nov. 15, 2021 issued in corresponding European Application No. 15768711.2.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
European Office Action dated Jun. 15, 2020 issued in corresponding European Application No. 15768711.2.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Dec. 3, 2021 issued in corresponding European Application No. 19800090.3.
Extended European Search Report dated Dec. 5, 2018 issued in corresponding European Application No. 16793622.8.
Extended European Search Report dated Jul. 23, 2021 issued in corresponding European Application No. 21150862.7.
Extended European Search Report dated Jul. 8, 2016 issued in corresponding European Application No. 14748567.6.
Extended European Search Report dated Mar. 14, 2017 issued in corresponding European Application No. 14843283.4.
Extended European Search Report dated Nov. 26, 2019 issued in corresponding European Application No. 19184148.5.
Extended European Search Report dated Oct. 18, 2017 issued in European Application No. 15768711.

(56) References Cited

OTHER PUBLICATIONS

Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
International Search Report and Written Opinion dated Aug. 11, 2016 issued in corresponding International Application No. PCT/US2016/032017.
International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jan. 14, 2020 issued in International Application No. PCT/US2019/060433.
International Search Report and Written Opinion dated Jul. 21, 2020 issued in corresponding International Application No. PCT/US2020/028779.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 14, 2020 issued in corresponding International Application No. PCT/US2020/036110.
International Search Report and Written Opinion dated Sep. 25, 2017, issued in corresponding Application No. PCT/US17/30922.
International Search Report dated Oct. 7, 2009 issued in corresponding International Application No. PCT/B2009/000071.
International Search Report issued Apr. 21, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101.
Japanese Notice of Allowance dated Jul. 11, 2017 issued in corresponding Japanese Application No. 2013-557-926, with English language summary.
Japanese Notice of Allowance dated Jul. 7, 2020 issued in corresponding Japanese Application No. 2016558799, with English translation of allowed claims.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 1, 2020 issued in corresponding Japanese Application No. 2017-559320, with English summary.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557-926, with English language summary.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jan. 7, 2020 issued in corresponding Japanese Application No. 2016-558799, with machine translation to English.
Japanese Office Action dated Jul. 23, 2019 issued in corresponding Japanese Application No. 2016-542062, with machine translation to English.
Japanese Office Action dated Jul. 28, 2020 issued in corresponding Japanese Application No. 2018-195960, with machine translation to English.
Japanese Office Action dated Jun. 27, 2017 issued in corresponding Japanese Application No. 2015-530101, with English language translation.
Japanese Office Action dated Jun. 29, 2021 issued in corresponding Japanese Application No. 2020-081074, with machine translation to English.
Japanese Office Action dated Jun. 30, 2020 issued in corresponding Japanese Application No. 2017559317, with machine translation to English.
Japanese Office Action dated Mar. 10, 2020 issued in corresponding Japanese Application No. 2017-559320, with machine translation to English.
Japanese Office Action dated Mar. 17, 2020 issued in corresponding Japanese Application No. 2019-071004, with machine translation to English.
Japanese Office Action dated Nov. 2, 2021 issued in corresponding Japanese Application No. 2020-192741, with English translation.
Japanese Office Action dated Oct. 10, 2017 issued in corresponding Japanese Application No. 2015-557091, with machine translation to English.
Japanese Office Action dated Oct. 15, 2019 issued in corresponding Japanese Application No. 2018-195960, with machine translation to English.
Japanese Office Action dated Sep. 26, 2017 issued in corresponding Japanese Application No. 2017-155346, with English translation.
Summons To Attend Oral Proceedings dated Dec. 20, 2019 issued in corresponding European Application No. 13763151.1.
Della Bella et al. "Non-contact mapping to guide catheter ablation of untolerated ventrical tachycardia" European Heart Journal, May 2002, 23(9)742-752.
Gupta et al. "Point of View Cardiac Mapping: Utility or Futility?", Indian Pacing and Electrophysiology Journal, vol. 2, No. 1, 2002, pp. 20-32.
He et al. "An equivalent body surface charge model representing three-dimensional bioelectrical activity" IEEE Transactions on Biomedical Engineering, 42.7 (Jul. 7, 1995) pp. 637-646.
Jackson, JD, "Surface Distributions of Charges and Dipoles and Discontinuities in the Electric Field and Potential", Classical Electrodynamics, 3rd edition, Dec. 1998, pp. 31-34.
Japanese Office Action dated Apr. 23, 2024 issued in Japanese Application No. 2021-572320, with machine translation to English.
Israel Office Action dated Jul. 29, 2024 issued in Israel Application No. 287822, with English translation.

(56) References Cited

OTHER PUBLICATIONS

Japanese Office Action dated Jan. 21, 2025 issued in Japanese Application No. 2021-572320, with machine translation to English.
Office Action dated Jan. 25, 2025 issued in Chinese Application No. 202080046108.8, with machine translation to English.

* cited by examiner

SYSTEMS AND METHODS FOR PERFORMING LOCALIZATION WITHIN A BODY

CROSS REFERENCE TO RELATED APPLICATIONS

The present application claims priority to U.S. Provisional Patent Application Ser. No. 62/857,055, entitled "Systems and Methods for Performing Localization Within a Body", filed Jun. 4, 2019, which is hereby incorporated by reference.

The present application, while not claiming priority to, may be related to U.S. Provisional Application Ser. No. 62/757,961, entitled "Systems and Methods for Calculating Patient Information", filed Nov. 9, 2018, which is hereby incorporated by reference.

The present application, while not claiming priority to, may be related to U.S. Provisional Application Ser. No. 62/668,659, entitled "Cardiac Information Processing System", filed May 8, 2018, which is hereby incorporated by reference.

The present application, while not claiming priority to, may be related to U.S. Provisional Application Ser. No. 62/619,897, entitled "System for Recognizing Cardiac Conduction Patterns", filed Jan. 21, 2018, and U.S. Provisional Application Ser. No. 62/668,647, entitled "System for Identifying Cardiac Conduction Patterns", filed May 8, 2018, each of which is hereby incorporated by reference.

The present application, while not claiming priority to, may be related to Patent Cooperation Treaty Application No. PCT/US2017/056064, entitled "Ablation System with Force Control", filed Oct. 11, 2017, which claims priority to U.S. Provisional Application Ser. No. 62/406,748, entitled "Ablation System with Force Control", filed Oct. 11, 2016, and U.S. Provisional Application Ser. No. 62/504,139, entitled "Ablation System with Force Control", filed May 20, 2017, each of which is hereby incorporated by reference.

The present application, while not claiming priority to, may be related to U.S. application Ser. No. 16/097,955, entitled "Cardiac Information Dynamic Display System and Method", filed Oct. 31, 2018, which is a 35 USC 371 national stage filing of Patent Cooperation Treaty Application No. PCT/US2017/030915, entitled "Cardiac Information Dynamic Display System and Method", filed May 3, 2017, published as WO 2017/192769, which claims priority to U.S. Provisional Application Ser. No. 62/331,351, entitled "Cardiac Information Dynamic Display System and Method", filed May 3, 2016, each of which is hereby incorporated by reference.

The present application, while not claiming priority to, may be related to U.S. application Ser. No. 16/012,051, entitled "Catheter, System and Methods of Medical Uses of Same, Including Diagnostic and Treatment Uses for the Heart", filed Jun. 19, 2018, which is a continuation of U.S. Pat. No. 10,004,459, entitled "Catheter, System and Methods of Medical Uses of Same, Including Diagnostic and Treatment Uses for the Heart", filed Feb. 20, 2015, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, published as WO 2014/036439, which claims priority to U.S. Patent Provisional Application Ser. No. 61/695,535, entitled "System and Method for Diagnosing and Treating Heart Tissue", filed Aug. 31, 2012, each of which is hereby incorporated by reference.

The present application, while not claiming priority to, may be related to U.S. application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/015261, entitled "Expandable Catheter Assembly with Flexible Printed Circuit Board (PCB) Electrical Pathways", filed Feb. 7, 2014, published as WO 2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, each of which is hereby incorporated by reference.

The present application, while not claiming priority to, may be related to U.S. patent application Ser. No. 16/014,370, entitled "Method and Device for Determining and Presenting Surface Charge and Dipole Densities on Cardiac Walls", filed Jun. 21, 2018, which is a continuation of U.S. patent application Ser. No. 15/435,763, entitled "Method and Device for Determining and Presenting Surface Charge and Dipole Densities on Cardiac Walls", filed Feb. 17, 2017, which is a continuation of U.S. Pat. No. 9,610,024, entitled "Method and Device for Determining and Presenting Surface Charge and Dipole Densities on Cardiac Walls", filed Sep. 25, 2015, which is a continuation of U.S. Pat. No. 9,167,982, entitled "Method and Device for Determining and Presenting Surface Charge and Dipole Densities on Cardiac Walls", filed Nov. 19, 2014, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of PCT Application No. PCT/CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 15/882,097, entitled "Device and Method for the Geometric Determination of Electrical Dipole Densities on the Cardiac Wall", filed Jan. 29, 2018, which is a continuation of U.S. Pat. No. 9,913,589, entitled "Device and Method for the Geometric Determination of Electrical Dipole Densities on the Cardiac Wall", filed Dec. 25, 2016, which is a continuation of U.S. Pat. No. 9,504,395, entitled "Device and Method for the Geometric Determination of Electrical Dipole Densities on the Cardiac Wall", filed Oct. 19, 2015, which is a continuation of U.S. Pat. No. 9,192,318, entitled "Device and Method for the Geometric Determination of Electrical Dipole Densities on the Cardiac Wall", filed Jul. 19, 2013, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB2009/000071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 15/926,187, entitled "Device and Method for the Geometric Determination of Electrical Dipole Densities on the Cardiac Wall", filed Mar. 20, 2018, which is a continuation of U.S. Pat. No. 9,968,268, entitled "Device and Method for the Geometric Determination of Electrical Dipole Densities on the Cardiac Wall", filed Aug. 8, 2017, which is a continuation of U.S. Pat. No. 9,757,044, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to U.S. Design patent application Ser. No. 29/593,043, entitled "Set of Transducer-Electrode Pairs for a Catheter", filed Feb. 6, 2017, which is a divisional of U.S. Design Pat. No. D782,686, entitled "Transducer-Electrode Pair for a Catheter", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to U.S. patent application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/15261, entitled "Expandable Catheter Assembly with Flexible Printed Circuit Board (PCB) Electrical Pathways", filed Feb. 7, 2014, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to U.S. patent application Ser. No. 16/111,538, entitled "Gas-Elimination Patient Access Device", filed Aug. 24, 2018, which is a continuation of U.S. Pat. No. 10,071,227, entitled "Gas-Elimination Patient Access Device", filed Jul. 14, 2016, which is a 35 USC 371 national stage filing of Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to U.S. patent application Ser. No. 15/128,563, entitled "Cardiac Analysis User Interface System and Method", filed Sep. 23, 2016, which is a 35 USC 371 national stage filing of Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to U.S. patent application Ser. No. 14/916,056, entitled "Devices and Methods for Determination of Electrical Dipole Densities on a Cardiac Surface", filed Mar. 2, 2016, which is a 35 USC 371 national stage filing of Patent Cooperation Treaty Application No. PCT/US2014/54942, entitled "Devices and Methods for Determination of Electrical Dipole Densities on a Cardiac Surface", filed Sep. 10, 2014, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

The present application, while not claiming priority to, may be related to U.S. patent application Ser. No. 15/569,457, entitled "Localization System and Method Useful in the Acquisition and Analysis of Cardiac Information", filed Oct. 26, 2017, which is a 35 USC 371 national stage filing of Patent Cooperation Treaty Application No. PCT/US2016/032420, entitled "Localization System and Method Useful in the Acquisition and Analysis of Cardiac Information", filed May 13, 2016, which claims priority to U.S. Patent Provisional Application Ser. No. 62/161,213, entitled "Localization System and Method Useful in the Acquisition and Analysis of Cardiac Information", filed May 13, 2015, which is hereby incorporated by reference.

The present application, while not claiming priority to, may be related to U.S. patent application Ser. No. 15/569,231, entitled "Cardiac Virtualization Test Tank and Testing System and Method", filed Oct. 25, 2017, which is a 35 USC 371 national stage filing of Patent Cooperation Treaty Application No. PCT/US2016/031823, filed May 11, 2016, which claims priority to U.S. Patent Provisional Application Ser. No. 62/160,501, entitled "Cardiac Virtualization Test Tank and Testing System and Method", filed May 12, 2015, which is hereby incorporated by reference.

The present application, while not claiming priority to, may be related to U.S. patent application Ser. No. 15/569,185, entitled "Cardiac Virtualization Test Tank and Testing System and Method", filed Oct. 25, 2017, which is a 35 USC 371 national stage filing of Patent Cooperation Treaty Application No. PCT/US2016/032017, filed May 12, 2016, which claims priority to U.S. Patent Provisional Application Ser. No. 62/160,529, entitled "Ultrasound Sequencing System and Method", filed May 12, 2015, which is hereby incorporated by reference.

The present application, while not claiming priority to, may be related to U.S. patent application Ser. No. 16/097,959, entitled "Cardiac Mapping System with Efficiency Algorithm", filed Oct. 31, 2018, which is a 35 USC 371 national stage filing of Patent Cooperation Treaty Application No. PCT/US2017/030922, entitled "Cardiac Mapping System with Efficiency Algorithm", filed May 3, 2017, which claims priority to U.S. Patent Provisional Application Ser. No. 62/413,104, entitled "Cardiac Mapping System with Efficiency Algorithm", filed Oct. 26, 2016, which is hereby incorporated by reference.

The present application, while not claiming priority to, may be related to U.S. Patent Provisional Application Ser.

No. 62/619,897, entitled "System for Recognizing Cardiac Conduction Patterns", filed Jan. 21, 2018, which is hereby incorporated by reference.

The present application, while not claiming priority to, may be related to U.S. Patent Provisional Application Ser. No. 62/668,647, entitled "System for Identifying Cardiac Conduction Patterns", filed May 8, 2018, which is hereby incorporated by reference.

The present application, while not claiming priority to, may be related to U.S. Provisional Application Ser. No. 62/668,659, entitled "Cardiac Information Processing System", filed May 8, 2018, which is hereby incorporated by reference.

FIELD OF THE INVENTION

The present invention relates generally to medical diagnostic and treatment systems, and in particular, to systems that record physiologic data, such as a cardiac data, from a patient.

BACKGROUND

Systems used by a clinician to perform a medical procedure, such as a diagnostic and/or therapeutic procedure, usually require assessment of one or more patient parameters, such as electrical and/or mechanical properties of tissue, as well as other patient information useful in performing the medical procedure. Procedures in which tissue is treated (e.g. ablated) often include an assessment of untreated tissue (e.g. before treatment), partially treated tissue (e.g. during treatment), and/or treated tissue (e.g. after treatment). It is often difficult to perform the assessment at the treatment site, due to limited space and other reasons. Accuracy and specificity of available assessments can be limited, and lead to lack of safety and/or lack of effectiveness of the treatment.

In such systems, localization can be performed to locate a catheter and its components within the anatomy of the patient, e.g., within a chamber of the heart. Localization can be accomplished by implementing a particular kind of localization mode. Some localization modes employ a spatially-distributed or spatially-varying field, present in or applied to the anatomy of the patient. In some instances, the field may interact with one or more intrinsic, local properties of the anatomy, to produce measurable effects or changes that encode the spatial information. Impedance-based localization is one mode often used, wherein a current-field or voltage-field is applied to the body and the resulting field distributes throughout the body, affected by the varying local impedances throughout the body. As a result, the corresponding voltage or current varies as a function of location. By measuring the voltage or current at any location, the position of the measurement within the body can be decoded by one of any number of means. However, impedance measurements are susceptible to changes in conditions during a procedure, such as those associated with a living being. Such changes can include changes in air, moisture, blood conductivity and so forth. These changes can detrimentally influence impedance measurements. A less common form of localization is magnetic-based localization, reliant on magnetic element such as coils to generate and sense magnetic fields. For this approach to be used, the device to be located would typically require a magnetic element. But only limited catheters have such elements. In either case, using one of these localization methods can be useful, even though the results may be less than desirable with respect to performing the procedure.

There is a need for systems that provide improved localization to enable improved performance of diagnostic and treatment procedures within the body.

SUMMARY

According to one aspect of the present inventive concepts, provided is a method of processing physiological information, comprising providing a processor coupled to a data storage device and providing a plurality of functional elements coupled to the processor and disposed within, on, and/or proximal to a body; establishing and calibrating a localization coordinate system by processing a first set of signals from a first set of the functional elements using a first localization mode; and recalibrating the localization coordinate system by processing a second set of signals from a second set of the functional elements using a second localization mode. The first localization mode is different from the second localization mode.

In some embodiments, the first and second localization modes are chosen from a group consisting of an impedance-based localization mode, a magnetic-based localization mode, and an ultrasound-based localization mode.

In some embodiments, the first localization mode is an impedance-based localization mode.

In some embodiments, the first localization mode is a magnetic-based localization mode.

In some embodiments, the first localization mode is an ultrasound-based localization mode.

In some embodiments, the second localization mode is an impedance-based localization mode.

In some embodiments, the second localization mode is a magnetic-based localization mode.

In some embodiments, the second localization mode is an ultrasound-based localization mode.

In some embodiments, the localization coordinate system is a three-dimensional (3D) coordinate system.

In some embodiments, an origin of the localization coordinated system is located within the body.

In some embodiments, the origin of the localization coordinated system is located within an organ of the body.

In some embodiments, the organ is a heart.

In some embodiments, the method includes inserting at least one object into the organ and/or the body, the at least one object comprising functional elements from the plurality of functional elements.

In some embodiments, the method includes localizing the at least one object within the localization coordinate system based on signals from functional elements of the at least one object and/or the first set and/or the second set of signals.

In some embodiments, the at least one object includes at least one catheter comprising catheter functional elements.

In some embodiments, the catheter functional elements include one or more signal sources generating at least some of the first and/or second set of signals.

In some embodiments, the catheter functional elements include one or more ultrasound elements.

In some embodiments, the catheter functional elements include one or more ultrasound sensors, transmitters, and/or transducers.

In some embodiments, the catheter functional elements include one or more magnetic elements.

In some embodiments, the one or more magnetic elements includes one or more magnetic coils.

In some embodiments, the catheter functional elements include one or more voltage or potential signal generation and/or sensing elements.

In some embodiments, the at least one catheter comprises a diagnostic catheter.

In some embodiments, the diagnostic catheter includes one or more magnetic elements used for magnetic-based localization.

In some embodiments, the diagnostic catheter includes one or more electrodes used for impedance-based localization.

In some embodiments, the diagnostic catheter includes one or more ultrasound elements used for ultrasound-based localization.

In some embodiments, the method further comprises localizing the diagnostic catheter within the localization coordinate system.

In some embodiments, the diagnostic catheter is a cardiac mapping catheter and the catheter functional elements include a plurality of electrodes configured to sense and/or record potentials related to cardiac activity and/or localization.

In some embodiments, the diagnostic catheter is a basket catheter and the catheter functional elements comprise a basket array of electrodes.

In some embodiments, the diagnostic catheter is a lasso catheter and the catheter functional elements comprise an array of electrodes.

In some embodiments, the diagnostic catheter includes a shaft having a distal end comprising an actuator slidable within a lumen of a sheath to deploy an array of functional elements within the body, and wherein the shaft, sheath, and/or actuator include one or more functional elements.

In some embodiments, each of the shaft and the actuator include one or more functional elements in the form of auxiliary electrodes, and the method comprises the processor determining relative distance measurements between the auxiliary electrodes on the shaft and the auxiliary electrodes on the actuator.

In some embodiments, the method further comprises the processor determining a shape of the array of functional elements based on the distance measurements.

In some embodiments, the array of functional elements is a basket array and the processor determines a shape of the basket array.

In some embodiments, the diagnostic catheter comprises at least one other functional element located on the shaft and chosen from a group consisting of an electrode, a coil, transducers, and/or a physiological sensor, and wherein the at least one other functional element is used for cardiac activity mapping and/or localization.

In some embodiments, the array of functional elements is a basket array, and the auxiliary electrodes include at least one magnetic sensor on the actuator and/or the shaft, and the method further comprises the processor determining a location and/or orientation of the basket array using the at least on magnetic sensor on the actuator and/or the shaft and magnetic localization.

In some embodiments, the basket array of functional elements has a known configuration and the method comprises the processor, using the known configuration of the basket array, locating one or more of the functional elements of the basket array based on determined locations of the at least one magnetic sensor.

In some embodiments, locating one or more of the functional elements of the basket array based includes estimating a position and orientation of all elements of the basket array could using magnetic localization.

In some embodiments, the method further comprises the processor determining a location and/or orientation of one or more additional device using magnetic localization by assessing, calculating, and/or determining a position of one or more elements of the one or more additional device relative to the magnetically localized basket array.

In some embodiments, the method further comprises the processor determining the relative position of the one or more additional device relative to basket array using one or more localization methods, such as ultrasonic localization and/or impedance based localization.

In some embodiments, the method further comprises performing intra-device localization using localization signals transmitted to and/or received from internally-located devices and/or functional elements and/or transmitted to and/or received from externally-located devices and/or functional elements.

In some embodiments, the at least one catheter comprises a second diagnostic catheter including a second set of catheter functional elements.

In some embodiments, the second set of catheter functional elements includes one or more electrodes used in the cardiac activity mapping and/or localization.

In some embodiments, the second diagnostic catheter is a coronary sinus mapping catheter structured and arranged for positioning within a coronary sinus of a heart.

In some embodiments, the coronary sinus mapping catheter comprises at least one catheter functional element located on a catheter shaft and chosen from a group consisting of an electrode, a magnetic element, a coil, an ultrasound element, a transducer, and/or a physiological sensor.

In some embodiments, the coronary sinus mapping catheter includes one or more magnetic elements used for magnetic-based localization.

In some embodiments, the coronary sinus mapping catheter includes one or more electrodes used for impedance-based localization.

In some embodiments, the coronary sinus mapping catheter includes one or more ultrasound elements used for ultrasound-based localization.

In some embodiments, the method further comprises localizing the coronary sinus mapping catheter within the localization coordinate system.

In some embodiments, the coronary sinus mapping catheter is a lasso catheter.

In some embodiments, the at least one catheter comprises a treatment catheter.

In some embodiments, the treatment catheter includes at least one treatment functional element.

In some embodiments, the at least one treatment functional element includes at least one ablation electrode.

In some embodiments, the treatment catheter includes one or more magnetic elements used for magnetic-based localization.

In some embodiments, the treatment catheter includes one or more electrodes used for impedance-based localization.

In some embodiments, the treatment catheter includes one or more ultrasound elements used for ultrasound-based localization.

In some embodiments, the method further comprises localizing the at least one treatment element within the localization coordinate system.

In some embodiments, the plurality of functional elements comprises external functional elements arranged outside and/or on the body, and wherein the external functional elements include one or more of the first set and/or the second set of functional elements.

In some embodiments, the external functional elements are chosen from a group of functional elements types consisting of impedance functional elements, magnetic functional elements, and functional elements.

In some embodiments, the functional elements types are chosen from a group consisting of an electrode, a voltage or potential sensor, an ultrasound transmitter, an ultrasound sensor, an ultrasound transducer, a magnetic element, and a magnetic coil.

In some embodiments, the method further comprises localizing at least one object within the localization coordinate system using signals generated and/or sensed by at least some of the external functional elements.

In some embodiments, the at least one object includes at least one catheter.

In some embodiments, the at least one catheter includes at least one diagnostic catheter.

In some embodiments, the at least one catheter includes at least one treatment catheter.

In some embodiments, the method includes providing at least one wearable garment comprising at least some of the external functional elements, including the one or more of the first set and/or second the set of functional elements, the wearable garment maintaining contact, pressure, and/or position of the external functional elements relative to the body.

In some embodiments, the at least one wearable garment takes the form of a vest, suit, shirt, bodysuit, or portion thereof.

In some embodiments, at least some of the external functional elements are removable from the at least one wearable garment.

In some embodiments, at least some of the external functional elements are embedded or disposed within the at least one wearable garment.

In some embodiments, the wearable garment includes at least two different external functional elements, as the one or more of the first set and/or the second set of functional elements, chosen from a group consisting of impedance functional elements, magnetic functional elements, and ultrasound functional elements.

In some embodiments, the at least two external functional elements includes a magnetic functional element and an impedance functional element.

In some embodiments, the at least two external functional elements includes a magnetic functional element and an ultrasound functional element.

In some embodiments, the at least two external functional elements includes an impedance functional element and an ultrasound functional element.

In some embodiments, the group consisting of the magnetic functional element, the impedance functional element, and the ultrasound functional element comprises at least two of an electrode, a voltage or potential sensor, an ultrasound transmitter, an ultrasound sensor, an ultrasound transducer, a magnetic element, and/or a magnetic coil.

In some embodiments, the method includes providing patches comprising at least some of the external functional elements, including the one or more of the first set and/or the second set of functional elements.

In some embodiments, the method includes affixing the patches to a torso of the body.

In some embodiments, one or more of the patches includes at least two different external functional elements, as the one or more of the first set and/or the second set of functional elements, chosen from a group consisting of a magnetic functional element, an impedance functional element, and an ultrasound functional element.

In some embodiments, the at least two external functional elements includes a magnetic functional element and an impedance functional element.

In some embodiments, the at least two external functional elements includes a magnetic functional element and an ultrasound functional element.

In some embodiments, the at least two external functional elements includes an impedance functional element and an ultrasound functional element.

In some embodiments, the group consisting of the magnetic functional element, the impedance functional element, and the ultrasound functional element comprises at least two of an electrode, a voltage or potential sensor, an ultrasound transmitter, an ultrasound sensor, an ultrasound transducer, a magnetic element, and/or a magnetic coil.

In some embodiments, the method further comprises recording physiologic data at one or more recording locations of the functional elements and transforming the physiological data into patient information at one or more target locations that are different from the recording locations.

In some embodiments, the method further comprises recording physiologic data at one or more recording locations of the first set and/or second set of functional elements.

In some embodiments, at least some of the physiological data is embodied in the first set and/or the second set of signals.

In some embodiments, the method further comprises applying a transfer matrix to the physiologic data at one or more recording locations to determine patient information at one or more target locations that are different from the recording locations.

In some embodiments, the method further comprises generating the transfer matrix from the first set and/or the second set of signals.

In some embodiments, generating the transfer matrix includes characterizing tissue properties between the recording locations and target locations.

In some embodiments, the transfer matrix is a scale matrix.

In some embodiments, the scale matrix is a combined scale matrix.

In some embodiments, generating the combined scale matrix includes generating a plurality of scale matrices and combining the plurality of scale matrices into a combined scale matrix.

In some embodiments, different ones of the plurality of scale matrices are generated at different locations within the localization coordinate system.

In some embodiments, the method includes determining if at least two of the plurality of scale matrices are sufficiently comparable that the localization data from the at least two scale matrices can be combined.

In some embodiments, if the at least two scale matrices are not sufficiently comparable, then adjusting at least one of the at least two scales matrices to make them comparable.

In some embodiments, adjusting at least one of the at least two scales matrices includes updating at least one localization parameter impacting a scale estimation of the combined scale matrix, such as a catheter shape.

In some embodiments, if the at least two scale matrices are sufficiently comparable, then stitching the at least two scale matrices together to generate the combined scale matrix.

In some embodiments, the scale matrix is a measure of a rate of change of a field value.

In some embodiments, the field value is a voltage or an impedance field.

In some embodiments, calibrating the localization coordinate system includes estimating the scale matrix.

In some embodiments, the method further comprises estimating the scale matrix by measuring voltage differences between functional elements having a known spacing.

In some embodiments, the functional elements are on a catheter whose dimensions are predetermined.

In some embodiments, the method further comprises the processor estimating, at particular cyclic time points of the patient's physiological variations, transformations and/or field properties to describe the field.

In some embodiments, the patient's physiological variations include heart and/or respiration cycles.

In some embodiments, the particular cyclic time points of the patient's physiological variations are time points when a complexity of the field is minimal, to simplify modeling, and at these particular time points, due to favorable physiological conditions, the applied field demonstrates reduced spatial non-linearity which allows for an easier description of the field and with lesser inputs.

In some embodiments, these time points are temporally located proximate a T wave and/or a P wave of an ECG signal of the patient.

In some embodiments, measuring the signal at a particular time point over a wider period of time leads to constancy of the source, and the constancy has a cycle that matches the time period of observation, and contributions to the signal changes from other sources can be observed within these measurements.

In some embodiments, transformations (e.g. models) describing the other sources can be estimated based on the observations.

In some embodiments, an artifact in the signal can comprise a discrete impulse, optionally caused by a short, high amplitude extraneous signal, such as a pacing pulse.

In some embodiments, the discrete impulse produces a waveform comprising a component with a "sharp" structure having a steep leading and/or trailing edge.

In some embodiments, when an artifact present in a localization signal, the processor observes a short "jump" in the determined position of the recording electrode or electrodes. Optionally wherein the localization signal is an impedance-based localization signal recorded by the electrode or electrodes to be localized.

In some embodiments, the method further comprises performing a thresholding algorithm based on observing signal variations during a non-artifact period, wherein the thresholding algorithm is configured to limit the observed jump in the position of the recording electrode or electrodes. Optionally, median filtering of the signal with a filtering period comparable to and/or greater than the length of an extraneous signal causing the artifact is also used to limit observed positional shift.

In some embodiments, the method further comprises the processor applying one or more additional filters to this signal comprising a component with a sharp structure, including filtering the artifact sufficiently to be negligible to observe. Optionally, the jump in the position of the recording electrode is negligible after two or more filters are applied.

In some embodiments, the method further comprises the process of limiting a sharp structure in the recorded signal by applying a first filter prior to a second filter can help prevent such a sharp structure from manifesting as an observable jump in the localized position of catheter. Optionally, the first filter is a median filter.

In some embodiments, the method further comprises the processor detecting a pacing pulse and, in response, ignoring or filtering signals recorded while the pacing pulse is present to avoid negatively affecting the localization of one or more other electrodes being localized while the pacing is present.

In some embodiments, the method further comprises localizing one or more of the functional elements relative to the body, wherein the localizing includes estimating a location of functional element by measuring a difference in a field value between the functional element and a location whose position with respect to the body and field value is known and multiplying the measured difference by the scale matrix, wherein the resultant output of is the position of the sensor with respect to the known location.

In some embodiments, the localization signals have a predominantly common mode component when recorded via one or more electrodes within the heart, and the method includes filtering the common mode signal from unintended circuit pathways and/or inter-connected system to substantially reduce leakage of the localization signals.

In some embodiments, the method further includes the processor using a common mode filter or common mode choke herein to prevent the common mode signal from leaking into the one or more unintended circuit pathways and/or inter-connected system. Optionally, the common mode filter or common mode chokes acts as a high impedance pathway relative to the one or more unintended circuit pathways and/or inter-connected system.

In some embodiments, the method further includes a pacing pulse passing though the common mode filter or common mode choke unimpeded, allowing for intended pacing functionality. Optionally, wherein the pacing pulse is recorded by an electrode connected to the one or more unintended circuit pathways and/or inter-connected system via the common mode filter or common mode choke.

In accordance with another aspect of the inventive concepts, provided is a physiological processing information system, comprising providing a processor coupled to a data storage device and providing a plurality of functional elements coupled to the processor and disposed within, on, and/or proximal to a body, including a first set of functional elements and a second set of functional elements. The processor is configured to process a first set of signals from the first set of functional elements to establish and calibrate a localization coordinate system using a first localization mode and process a second set of signals from the second set of functional elements to recalibrate the localization coordinate system using a second localization mode, and the first localization mode is different from the second localization mode.

In some embodiments, the first and second localization modes are chosen from a group consisting of an impedance-based localization mode, a magnetic-based localization mode, and an ultrasound-based localization mode.

In some embodiments, the first localization mode is an impedance-based localization mode.

In some embodiments, the first localization mode is a magnetic-based localization mode.

In some embodiments, the first localization mode is an ultrasound-based localization mode.

In some embodiments, the second localization mode is an impedance-based localization mode.

In some embodiments, the second localization mode is a magnetic-based localization mode.

In some embodiments, the second localization mode is an ultrasound-based localization mode.

In some embodiments, the localization coordinate system is a three-dimensional (3D) coordinate system.

In some embodiments, an origin of the localization coordinated system is located within the body.

In some embodiments, the origin of the localization coordinated system is located within an organ of the body.

In some embodiments, the organ is a heart.

In some embodiments, the system further comprises at least one object into insertable into the organ and/or the body, the at least one object comprising functional elements from the plurality of functional elements.

In some embodiments, the processor is configured to localize the at least one object within the localization coordinate system based on signals from functional elements of the at least one object and/or the first set and/or the second set of signals.

In some embodiments, the at least one object includes at least one catheter comprising catheter functional elements.

In some embodiments, the catheter functional elements include one or more signal sources configured to generate at least some of the first and/or second set of signals.

In some embodiments, the catheter functional elements include one or more ultrasound elements.

In some embodiments, the catheter functional elements include one or more ultrasound sensors, transmitters, and/or transducers.

In some embodiments, the catheter functional elements include one or more magnetic elements.

In some embodiments, the one or more magnetic elements includes one or more magnetic coils.

In some embodiments, the catheter functional elements include one or more voltage or potential signal generation and/or sensing elements.

In some embodiments, the at least one catheter comprises a diagnostic catheter.

In some embodiments, the diagnostic catheter includes one or more magnetic elements used for magnetic-based localization.

In some embodiments, the diagnostic catheter includes one or more electrodes used for impedance-based localization.

In some embodiments, the diagnostic catheter includes one or more ultrasound elements used for ultrasound-based localization. system In some embodiments, the processor is configured to localize the diagnostic catheter within the localization coordinate system.

In some embodiments, the diagnostic catheter is a cardiac mapping catheter and the catheter functional elements include a plurality of electrodes configured to sense and/or record potentials related to cardiac activity and/or localization.

In some embodiments, the diagnostic catheter is a basket catheter and the catheter functional elements comprise a basket array of electrodes.

In some embodiments, the diagnostic catheter is a lasso catheter and the catheter functional elements comprise an array of electrodes.

In some embodiments, the diagnostic catheter includes a shaft having a distal end comprising an actuator slidable within a lumen of a sheath to deploy an array of functional elements within the body, and wherein the shaft, sheath, and/or actuator include one or more functional elements.

In some embodiments, each of the shaft and the actuator include one or more functional elements in the form of auxiliary electrodes, and the processor is configured to determine relative distance measurements between the auxiliary electrodes on the shaft and the auxiliary electrodes on the actuator.

In some embodiments, the processor is configured to determine a shape of the array of functional elements based on the distance measurements.

In some embodiments, the array of functional elements is a basket array and the processor determines a shape of the basket array.

In some embodiments, the diagnostic catheter comprises at least one other functional element located on the shaft and chosen from a group consisting of an electrode, a coil, transducers, and/or a physiological sensor, and wherein the at least one other functional element is used for cardiac activity mapping and/or localization.

In some embodiments, the array of functional elements is a basket array, and the auxiliary electrodes include at least one magnetic sensor on the actuator and/or the shaft, and the processor is configured to determine a location and/or orientation of the basket array using the at least on magnetic sensor on the actuator and/or the shaft and magnetic localization.

In some embodiments, the basket array of functional elements has a known configuration, and the processor is configured, using the known configuration of the basket array, to locate one or more of the functional elements of the basket array based on determined locations of the at least one magnetic sensor.

In some embodiments, the processor is configured to estimate a position and orientation of all elements of the basket array using magnetic localization, to locate one or more of the functional elements of the basket array based.

In some embodiments, the processor is configured to determine a location and/or orientation of one or more additional device using magnetic localization by assessing, calculating, and/or determining a position of one or more elements of the one or more additional device relative to the magnetically localized basket array.

In some embodiments, the processor is configured to determine the relative position of the one or more additional device relative to basket array using one or more localization methods, such as ultrasonic localization and/or impedance based localization.

In some embodiments, the processor is configured to perform intra-device localization using localization signals transmitted to and/or received from internally-located devices and/or functional elements and/or transmitted to and/or received from externally-located devices and/or functional elements.

In some embodiments, the at least one catheter comprises a second diagnostic catheter including a second set of catheter functional elements.

In some embodiments, the second set of catheter functional elements includes one or more electrodes used in the cardiac activity mapping and/or localization.

In some embodiments, the second diagnostic catheter is a coronary sinus mapping catheter structured and arranged for positioning within a coronary sinus of a heart.

In some embodiments, the coronary sinus mapping catheter comprises at least one catheter functional element located on a catheter shaft and chosen from a group consisting of an electrode, a magnetic element, a coil, an ultrasound element, a transducer, and/or a physiological sensor.

In some embodiments, the coronary sinus mapping catheter includes one or more magnetic elements used for magnetic-based localization.

In some embodiments, the coronary sinus mapping catheter includes one or more electrodes used for impedance-based localization.

In some embodiments, the coronary sinus mapping catheter includes one or more ultrasound elements used for ultrasound-based localization.

In some embodiments, the processor is further configured to localize the coronary sinus mapping catheter within the localization coordinate system.

In some embodiments, the coronary sinus mapping catheter is a lasso catheter.

In some embodiments, the at least one catheter comprises a treatment catheter.

In some embodiments, the treatment catheter includes at least one treatment functional element.

In some embodiments, the at least one treatment functional element includes at least one ablation electrode.

In some embodiments, the treatment catheter includes one or more magnetic elements used for magnetic-based localization.

In some embodiments, the treatment catheter includes one or more electrodes used for impedance-based localization.

In some embodiments, the treatment catheter includes one or more ultrasound elements used for ultrasound-based localization.

In some embodiments, the processor is configured to localizing the at least one treatment element within the localization coordinate system.

In some embodiments, the plurality of functional elements comprises external functional elements arranged outside and/or on the body, and wherein the external functional elements include one or more of the first set and/or the second set of functional elements.

In some embodiments, the external functional elements are chosen from a group of functional elements types consisting of impedance functional elements, magnetic functional elements, and functional elements.

In some embodiments, the functional elements types are chosen from a group consisting of an electrode, a voltage or potential sensor, an ultrasound transmitter, an ultrasound sensor, an ultrasound transducer, a magnetic element, and a magnetic coil.

In some embodiments, the system is further configured to localize at least one object within the localization coordinate system using signals generated and/or sensed by at least some of the external functional elements.

In some embodiments, the at least one object includes at least one catheter.

In some embodiments, the at least one catheter includes at least one diagnostic catheter.

In some embodiments, the at least one catheter includes at least one treatment catheter.

In some embodiments, the system further comprises at least one wearable garment comprising at least some of the external functional elements, including the one or more of the first set and/or second the set of functional elements, the wearable garment maintaining contact, pressure, and/or position of the external functional elements relative to the body.

In some embodiments, the at least one wearable garment takes the form of a vest, suit, shirt, bodysuit, or portion thereof.

In some embodiments, at least some of the external functional elements are removable from the at least one wearable garment.

In some embodiments, at least some of the external functional elements are embedded or disposed within the at least one wearable garment.

In some embodiments, the wearable garment includes at least two different external functional elements, as the one or more of the first set and/or the second set of functional elements, chosen from a group consisting of impedance functional elements, magnetic functional elements, and ultrasound functional elements.

In some embodiments, the at least two external functional elements includes a magnetic functional element and an impedance functional element.

In some embodiments, the at least two external functional elements includes a magnetic functional element and an ultrasound functional element.

In some embodiments, the at least two external functional elements includes an impedance functional element and an ultrasound functional element.

In some embodiments, the group consisting of the magnetic functional element, the impedance functional element, and the ultrasound functional element comprises at least two of an electrode, a voltage or potential sensor, an ultrasound transmitter, an ultrasound sensor, an ultrasound transducer, a magnetic element, and/or a magnetic coil.

In some embodiments, the system further comprises patches comprising at least some of the external functional elements, including the one or more of the first set and/or the second set of functional elements.

In some embodiments, the patches are affixable to a torso of the body.

In some embodiments, one or more of the patches includes at least two different external functional elements, as the one or more of the first set and/or the second set of functional elements, chosen from a group consisting of a magnetic functional element, an impedance functional element, and an ultrasound functional element.

In some embodiments, the at least two external functional elements includes a magnetic functional element and an impedance functional element.

In some embodiments, the at least two external functional elements includes a magnetic functional element and an ultrasound functional element.

In some embodiments, the at least two external functional elements includes an impedance functional element and an ultrasound functional element.

In some embodiments, the group consisting of the magnetic functional element, the impedance functional element, and the ultrasound functional element comprises at least two of an electrode, a voltage or potential sensor, an ultrasound transmitter, an ultrasound sensor, an ultrasound transducer, a magnetic element, and/or a magnetic coil.

In some embodiments, the system is configured to record physiologic data at one or more recording locations of the functional elements and transform the physiological data into patient information at one or more target locations that are different from the recording locations.

In some embodiments, the processor is configured to record physiologic data at one or more recording locations of the first set and/or second set of functional elements.

In some embodiments, at least some of the physiological data is embodied in the first set and/or the second set of signals.

In some embodiments, the processor is configured to apply a transfer matrix to the physiologic data at one or more recording locations to determine patient information at one or more target locations that are different from the recording locations.

In some embodiments, the processor is configured to generate the transfer matrix from the first set and/or the second set of signals.

In some embodiments, the processor is configured to generate the transfer matrix by characterizing tissue properties between the recording locations and target locations.

In some embodiments, the transfer matrix is a scale matrix.

In some embodiments, the scale matrix is a combined scale matrix.

In some embodiments, the processor is configured to generate the combined scale matrix by generating a plurality of scale matrices and combining the plurality of scale matrices into a combined scale matrix.

In some embodiments, the system is configured to generate different ones of the plurality of scale matrices at different locations within the localization coordinate system.

In some embodiments, the processor is configured to determine if at least two of the plurality of scale matrices are sufficiently comparable that the localization data from the at least two scale matrices can be combined.

In some embodiments, if the at least two scale matrices are not sufficiently comparable, the processor is configured to adjust at least one of the at least two scales matrices to make them comparable.

In some embodiments, the processor is configured to adjust at least one of the at least two scales matrices by updating at least one localization parameter impacting a scale estimation of the combined scale matrix, such as a catheter shape.

In some embodiments, if the at least two scale matrices are sufficiently comparable, the processing is configured to stitch the at least two scale matrices together to generate the combined scale matrix.

In some embodiments, wherein the scale matrix is a measure of a rate of change of a field value.

In some embodiments, the field value is a voltage or an impedance field.

In some embodiments, wherein the processor is configured to calibrate the localization coordinate system by estimating the scale matrix.

In some embodiments, wherein the processor is further configured to estimate the scale matrix by measuring voltage differences between functional element having a known spacing.

In some embodiments, the functional elements are on a catheter whose dimensions are predetermined.

In some embodiments, the processor is configured to estimate, at particular cyclic time points of the patient's physiological variations, transformations and/or field properties to describe the field.

In some embodiments, the patient's physiological variations include heart and/or respiration cycles.

In some embodiments, the particular cyclic time points of the patient's physiological variations are time points when a complexity of the field is minimal, to simplify modeling, and at these particular time points, due to favorable physiological conditions, the applied field demonstrates reduced spatial non-linearity which allows for an easier description of the field and with lesser inputs.

In some embodiments, these time points are temporally located proximate a T wave and/or a P wave of an ECG signal of the patient.

In some embodiments, measuring the signal at a particular time point over a wider period of time leads to constancy of the source, and the constancy has a cycle that matches the time period of observation, and contributions to the signal changes from other sources can be observed within these measurements.

In some embodiments, transformations and/or models describing the other sources can be estimated based on the observations.

In some embodiments, an artifact in the signal can comprise a discrete impulse, optionally caused by a short, high amplitude extraneous signal, such as a pacing pulse.

In some embodiments, the discrete impulse produces a waveform comprising a component with a "sharp" structure having a steep leading and/or trailing edge.

In some embodiments, when the artifact present in a localization signal, the processor is configured to observe a short "jump" in the determined position of the recording electrode or electrodes. Optionally wherein the localization signal is an impedance-based localization signal recorded by the electrode or electrodes to be localized.

In some embodiments, the processor is configured to perform a thresholding algorithm based on observing signal variations during a non-artifact period, and the thresholding algorithm is configured to limit the observed jump in the position of the recording electrode or electrodes. Optionally, median filtering of the signal with a filtering period comparable to and/or greater than the length of an extraneous signal causing the artifact can also be used to limit observed positional shift.

In some embodiments, the processor is configured to apply one or more additional filters to the signal comprising a component with a sharp structure, including filtering the artifact sufficiently to be negligible to observe. Optionally, the jump in the position of the recording electrode is negligible after two or more filters are applied.

In some embodiments, the processor limits a sharp structure in the recorded signal by applying a first filter prior to a second filter prevents or mitigates a sharp structure from manifesting as an observable jump in the localized position of catheter. Optionally, wherein the first filter is a median filter.

In some embodiments, the processor is configured to detect a pacing pulse and to, in response, ignore and/or filter signals recorded while the pacing pulse is present to avoid negatively affecting the localization of one or more other electrodes being localized while the pacing is present.

In some embodiments, the system is configured to localize one or more of the functional elements relative to the body, including estimating a location of functional element by measuring a difference in a field value between the functional element and a location whose position with respect to the body and field value is known and multiplying the measured difference by the scale matrix. The resultant output of is the position of the sensor with respect to the known location.

In some embodiments, the localization signals have a predominantly common mode component when recorded via one or more electrodes within the heart, and the processor is configured to filter the common mode signal from unintended circuit pathways and/or inter-connected system to substantially reduce leakage of the localization signals.

In some embodiments, the processor is configured to use a common mode filter or common mode choke to prevent the common mode signal from leaking into the one or more unintended circuit pathways and/or inter-connected system. Optionally, the common mode filter or common mode chokes acts as a high impedance pathway relative to the one or more unintended circuit pathways and/or inter-connected system.

In some embodiments, the common mode filter or common mode choke are configured so that a pacing pulse passing though the common mode filter or common mode choke is unimpeded, allowing for intended pacing functionality. Optionally, the pacing pulse is recorded by an electrode connected to the one or more unintended circuit pathways and/or inter-connected system via the common mode filter or common mode choke.

In accordance with aspects of the inventive concepts, provided is a method of forming a localization coordinate system, as shown and described.

In accordance with aspects of the inventive concepts, provided is a method of localizing and object in a localization coordinate system, as shown and described.

In accordance with aspects of the inventive concepts, provided is a system for establishing and calibrating a localization coordinate system, as shown and described.

In accordance with aspects of the inventive concepts, provided is a system for localizing an object in a localization coordinate system, as shown and described.

In accordance with aspects of the inventive concepts, provided is a localization patch, as shown and described.

In accordance with aspects of the inventive concepts, provided is a localization wearable garment, as shown and described.

The technology described herein, along with the attributes and attendant advantages thereof, will best be appreciated and understood in view of the following detailed description taken in conjunction with the accompanying drawings in which representative embodiments are described by way of example.

DETAILED DESCRIPTION OF THE DRAWINGS

Figure 1:
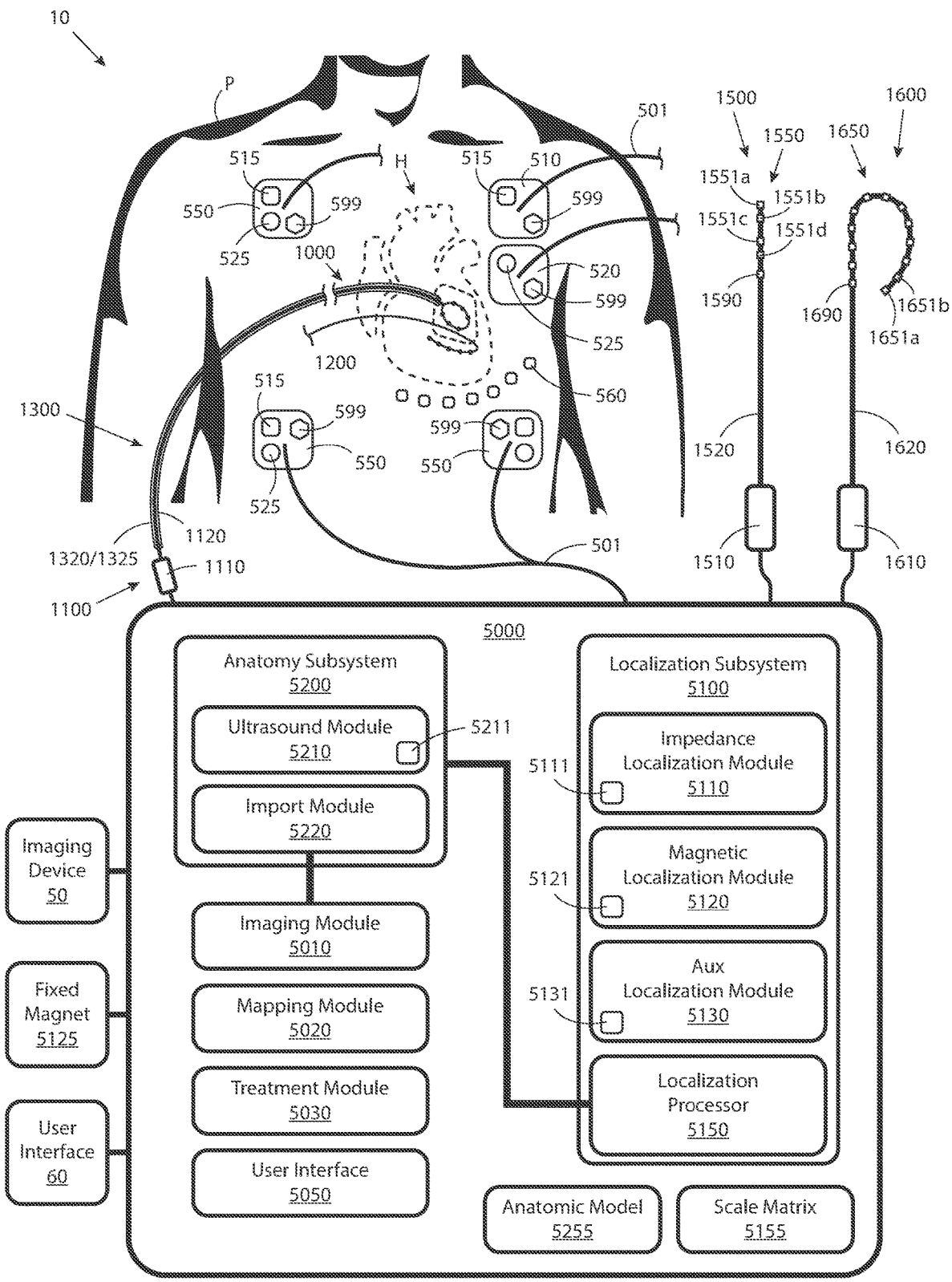
FIG. 1 illustrates a schematic view of an embodiment of a system for performing localization of an apparatus within a body, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input and produces an output. For example, a transducer can include an electrode that receives electrical energy and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "mapping procedure" shall include a clinical procedure performed on a patient that produces electrical activity information related to tissue of the patient, such as organ tissue (e.g. brain or heart tissue).

As used herein, the term "localization procedure" shall include the process of establishing a coordinate system, and using one or more signals, such as electrical signals, to determine the position of one or more objects or portions of objects ("objects" herein) within that system. In some embodiments, the process of localization incorporates one or more signals generated from one or more sources (e.g. electrodes), the signals changing as a function of space and/or time, and a sensor (e.g. an electrode) that measures the generated signals from a recording location. The recording location of the sensor can be on the object being localized or it can be separate from the object being localized. Analysis of and/or calculation performed on the measured signal can be used to determine a positional relationship of the sensor and/or the object to the one or more sources of the generated signal. The method of localization can incorporate two or more generated signals to increase the number and/or accuracy of positional relationships between the sensor and the signal source. The sensor and the object can be a single component and/or they can be multiple components that are co-located. In some embodiments, the signal change as a function of time and/or space includes interactions of the signal with the measurement environment. In other embodiments, the process of localization measures an intrinsic or existing characteristic of the object, sensor, and/or measurement environment, such as by measuring a signal from an accelerometer positioned on the object or sensor and incorporating information from the accelerometer signal in the analysis.

As used herein, the term "ablation procedure" shall include an ablative treatment procedure performed on patient tissue that has been identified as contributing to undesired electrical activity—such as activity associated with an arrhythmia of the heart (e.g., atrial fibrillation) or undesired state of the brain (e.g. seizure or tremor).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Provided herein are systems and methods for calculating patient information. Patient physiologic data is recorded at one or more recording locations, and a transformation, such as a transfer matrix, is used to determine patient information at one or more target locations that can be remote from the recording locations. Electrical information can be recorded by electrodes placed on the skin of the patient and/or within the patient, and electrical and/or other patient information can be calculated at target locations, such as target locations including an organ of the patient (e.g. the heart or the brain). Systems of the present inventive concepts can include components used to determine the transformation, such as electrodes, magnets, coils, or other sensors and transducers that characterize tissue properties between a recording location and a target location, the characterization performed on the patient for whom the patient information is to be calculated, and/or one or more similar mammalian subjects.

Referring now to FIG. 1, illustrated is a schematic view of an embodiment of a system 10 configured to perform localization of at least one apparatus within a body, consistent with the present inventive concepts. The system 10 can comprise a variety of components, subsystems, and the like, that are configured to cooperatively record and analyze physiological information, diagnose physiological conditions and/or maladies, and/or treat physiological conditions and/or maladies. The system 10 can include a console 5000 comprising one or more processors, data storage devices, and functional modules that cooperatively receive data and information from a plurality of different external functional elements, process the received data and information, and generate outputs, e.g., information shown on one or more displays, based at least in part on the processed data and information.

The external functional elements can include one or more catheters 1000 configured for insertion into the body, e.g., such as a human body or patient P. In various embodiments, at least one of the one or more catheters can be insertable in a cardiac chamber of a heart H and the system 10 can be configured to record and analyze physiological information, diagnose physiological conditions and/or maladies, and/or treat physiological conditions and/or maladies associated with the heart H. Such catheters and/or functional elements thereof can be localized using a combination of a plurality of localization technologies or modes, such as impedance localization, magnetic localization, and ultrasound localization. The external functional elements can also comprise one or more patches 500 (e.g., patches 510, 520, 550) comprising electrodes, magnetic elements, and/or combinations thereof. The patches can be external to the patient, e.g., the patches 500 could be configured for application to a torso of the patient P. The patches 500 and catheters 1000, or components thereof, can be configured to provide data and information to the console to perform the functions of the different localization modes used, e.g., impedance, magnetic, and/or ultrasound localization technologies.

Figure 1A:
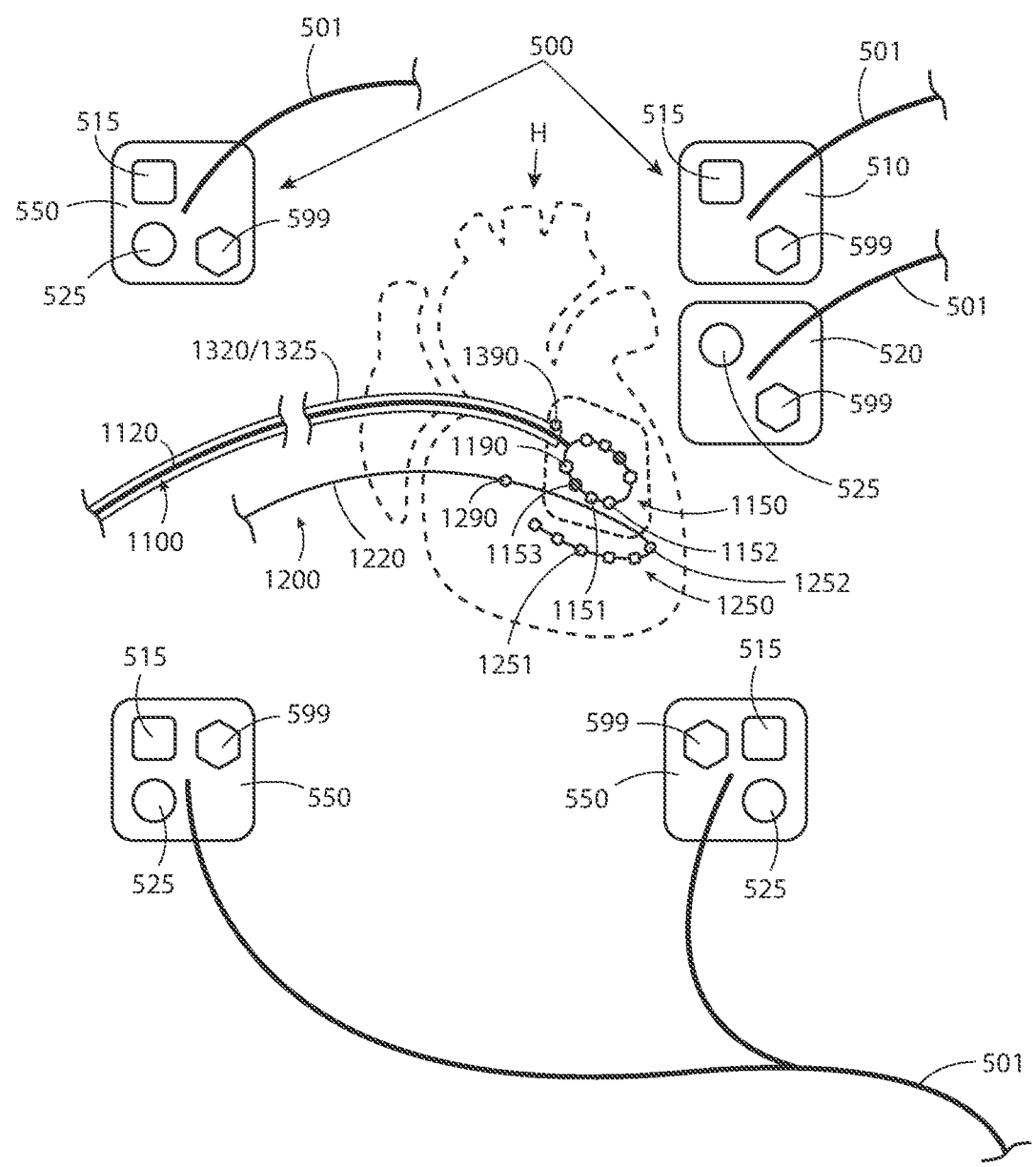
FIG. 1A illustrates a schematic view of embodiments of portions of the system of FIG. 1 useful for localization, consistent with the present inventive concepts.
Figure 2:
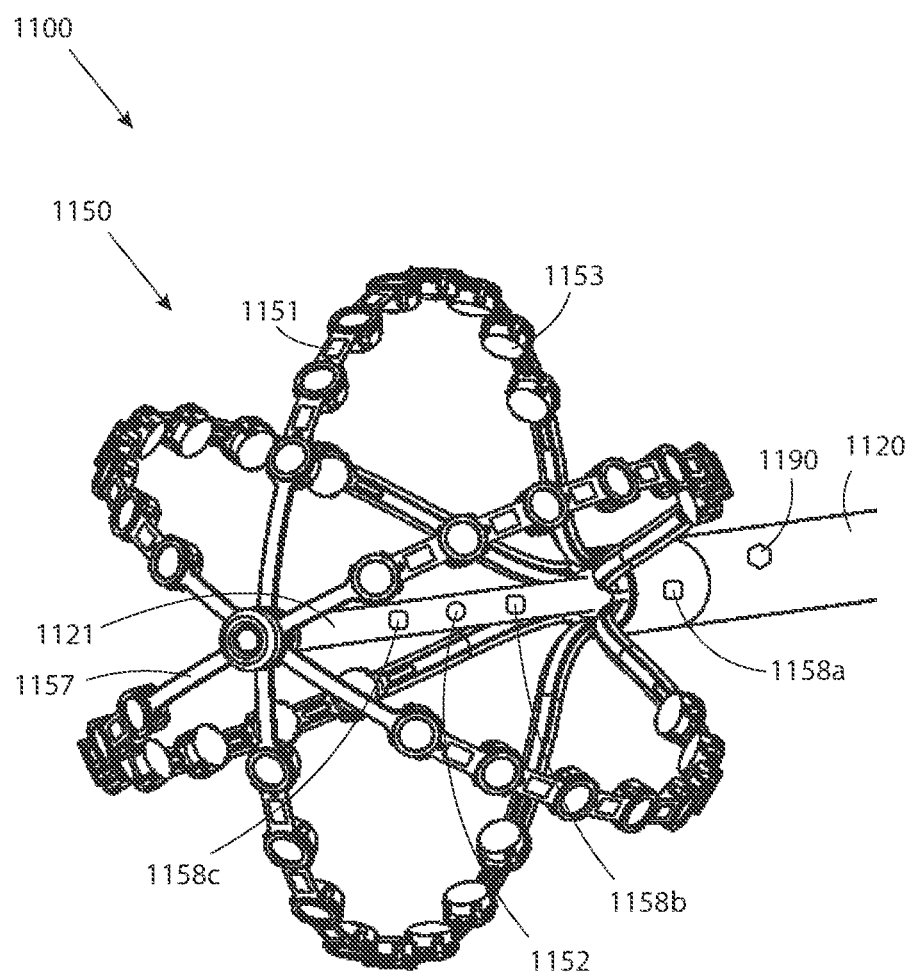
FIG. 2 illustrates a view of an embodiment of portions of one or more catheters forming part of the system of FIG. 1, consistent with the present inventive concepts.

In FIG. 1, a plurality of catheters 1000 are shown, including one or more diagnostic, localization, and/or treatment catheters. FIG. 1A illustrates a schematic view of portions of the system of FIG. 1 useful for localization and FIG. 2 illustrates a view of an embodiment of portions of one or more catheters forming part of the system of FIG. 1. The system can include a console 5000 comprising various processing and data storage elements or functional module of at least one special purpose computer. A variety of different types of diagnostic, treatment, and localization functional elements, e.g., internal and external functional elements, can be coupled to the console 5000 for use on or with patient P. In various embodiments, a display (such as an output component 60, described herebelow) can be coupled to, and at least partially driven by, the console and configured to output information, data, displays, images, graphs, and the like based on the processing of information and data received from one or more external sources, such as a plurality of catheters 1000 and/or a plurality of patches 500.

In the embodiments shown, the plurality of catheters 1100 includes at least one diagnostic catheter, such as diagnostic catheter 1100 and/or diagnostic catheter 1200. FIG. 2 shows an example embodiment of a portion of diagnostic catheter 1100. As an example, the diagnostic catheter 1100 can include a basket array 1150 comprising a plurality of splines 1157. One or more of the plurality of splines 1157 includes one or more functional elements configured to sense and/or record potentials relating to cardiac activity and/or for localization. In various embodiments, the array 1150 can include between 3-8 splines. In the particular example of FIG. 2, the array 1150 includes 6 splines, each spline comprising a plurality of sensing, recording, and/or localizing devices as functional elements.

In FIGS. 1, 1A, and 2, one or more of the splines 1157 includes functional elements in the form of electrodes 1151, which are configured for sensing and recording data useful for cardiac activity mapping, and/or localization. Electrodes 1151 can be used for mapping, localization, and/or, in some embodiments, for delivering ablation energy. The electrodes 1151 can be coupled to console 5000, which can be configured to drive the electrodes 1151 and receive and record data from the electrodes 1151. One or more of the splines 1157 further includes ultrasound transducers (USTs) 1153, which can include at least one ultrasound emitter and ultrasound sensor. The ultrasound transducers 1153 can be configured for localization of the basket array 1150 or other catheters or elements within the heart H, and can also be configured for sensing data useful for generating and/or updating an image of the heart H or other anatomy.

The catheter 1100 includes a catheter shaft 1120 configured to slide within a lumen 1325 in a shaft 1320 of a sheath 1300, such as a transseptal sheath, used for insertion and translation inside the patient P, e.g., to deliver the basket array 1150 to the heart H. The sheath 1300 can comprise at least one functional element 1390, such as an electrode, coil, ultrasound transducer, and/or physiological sensor, located on a distal end of the shaft 1320. In some embodiments, functional element 1390 comprises one or more transducers, as described hereabove. A handle 1110 used to steer the catheter within the patient P is located at a proximal end of the catheter shaft 1120 and sheath 1300. The basket array 1150 extends from a distal end of the catheter shaft 1120. In various embodiments, the array 1150 can be or include an expandable/collapsible basket array coupled to a distal end of the catheter shaft 1120. An actuator 1121 is slideable within the shaft 1120 and has a distal end coupled to or engaged with a distal end of the array 1150. In various embodiments, the actuator 1121 extends distally to collapse array 1150, e.g., by straightening the splines 1157, and retracts proximally to expand array 1150, by outwardly bowing the splines 1157.

In various embodiments, the catheter shaft 1120, the array 1150, and/or the actuator 1121 can include one or more functional elements configured for generating, sensing, and/or recording data useful for performing one or more methods of localization, e.g., magnetic localization, impedance-based localization, and/or ultrasound-based localization. Referring to FIG. 2, the actuator 1121 can include one or more magnetic elements 1152 that can be "driven" via console 5000 to create magnetic field or can "sense" a magnetic field. That is, console 5000 can be coupled to the magnetic elements 1152 and configured to drive the magnetic elements 1152 to establish a magnetic field useful for localization, e.g., localization of array 1150, and/or its functional elements, actuator 1121, and/or other functional elements within the patient P or heart H, such as an ablation catheter or ablation functional element. In this embodiment, at least one magnetic element 1152 is disposed along an intermediate portion, e.g., in the middle or close to the middle, of the actuator 1121 when fully extended or substantially fully extended.

A set of auxiliary functional elements 1158, e.g., electrodes, can optionally be included to measure the actuator 1121 position relative to the distal end of shaft 1120. In the embodiment of FIG. 2, auxiliary electrode 1158a is located on, in or at the distal end of shaft 1120, other auxiliary electrodes 1158b-c are located on, in, or at actuator 1121 used. Relative distance measurements between the auxiliary electrodes 1158a on shaft 1120 and one or more of auxiliary electrodes 1158b-c can be used, e.g., by console 5000, to determine the relative distances. Accordingly, actuator 1121 and shaft 1120 can include electrodes 1158a-c, which can be used as "measuring stick" to help determine the shape of basket array 1150. The catheter 1100 can also comprise at least one other functional element 1190, such as an electrode, a coil, and/or a physiological sensor, located on catheter shaft 1120. In some embodiments, functional element 1190 comprises one or more transducers, as described hereabove. While not shown in FIG. 2, actuator 1121 could include one or more USTs 1153 in various embodiments. In some embodiments, the location and orientation of basket array 1150 is determined using the magnetic sensors 1152 and magnetic localization systems described herein. Using a known configuration of basket array 1150, one or more of USTs 1153 and/or electrodes 1151 can be located based on the determined location of magnetic sensors 1152 (e.g. the entire position and orientation of all elements of basket array 1150 could be estimated using the magnetic localization system). In some embodiments, the position and/or orientation of one or more additional devices (e.g. electrode array 1250 of catheter 1200) is determined using the magnetic localization system by assessing the position of one or more elements of the additional device (e.g. electrodes 1251 of electrode array 1250) relative to the magnetically localized basket array 1150. For example, the relative position of an additional device relative to basket array 1150 can be determined using one or more localization methods, such as ultrasonic localization and/or impedance based localization, such as are described herein. In some embodiments, this intra-device localization is achieved using localization signals applied from the internally-located devices (e.g. signals transmitted and received from devices within the patient) and/or externally (e.g. signals transmitted from external to the patient, such as via one or more patches similar to as described herein).

With respect to FIGS. 1 and 1A, in various embodiments a second diagnostic catheter 1200 can optionally be included. Catheter 1200 can be attached to a shaft 1220 for insertion into the patient P and delivery to the heart H. For example, in some embodiments, catheter 1200 can be a coronary sinus mapping catheter, which is structured and arranged for positioning within the coronary sinus of the heart H. Catheter 1200 can include an electrode array 1250 comprising one or more functional elements in the form of electrodes 1251, e.g., such as electrodes used in cardiac activity mapping and/or localization. The electrode array 1250 can also include one or more magnetic elements 1252, which could be used for magnetic localization. The catheter 1200 can also comprise at least one other functional element 1290, such as an electrode, coil, and/or physiological sensor, located on catheter shaft 1220. In some embodiments, functional element 1290 comprises one or more transducers, as described hereabove.

With respect to FIGS. 1 and 1A, in various embodiments a treatment catheter 1500 can also be included in system 10, e.g., for insertion into the heart H (or other anatomy) of the patient P. The treatment catheter 1500 can be, as examples, an ablation catheter, such as radio frequency (RF) ablation catheter, an alternative light energy catheter, a microwave therapy catheter, a cryoablation catheter, or an ultrasound or other sound energy catheter. Energy delivered by the treatment catheter can be delivered as a constant or direct energy; a switched, alternating, or pulsed energy; and/or a modulated or phased energy. The therapeutic effect of the energy delivered by the catheter can be delivered by direct contact and/or indirect contact (e.g., without physical contact, such as by a field effect). The catheter 1500 can comprise a shaft 1520 with a handle 1510 at its proximal end. At a distal end of shaft 1520 is disposed a treatment array 1550 comprising at least one functional element 1551. As examples, the functional elements of the treatment array 1550 can include one or more type of energy delivery element(s) 1551, such as one or more RF delivery electrode, one or more optical component for delivering light energy, cold energy, and/or one or more sound transducer for delivering ultrasound energy. In some embodiments, electrodes 1551*a-d* can be used for ablation treatment, but in another embodiment, one electrode (e.g., electrode 1551*a*) could be used for ablation and one or more of the remaining electrodes 1551*b-c* could still exist for localization, e.g., if the array 1550 comprises a cryoablation tip. In various embodiments, functional element 1551*a* could be a treatment element (e.g., RF, CRYO, etc.), and functional elements 1551*b,c,d* could be electrodes for localizing treatment element 1551*a*. In another embodiment, the array 1550 includes four electrodes 1551*a-d* for RF ablation. The catheter 1500 can also comprise at least one other functional element 1590, such as an electrode, coil, and/or physiological sensor, located on catheter shaft 1520. In some embodiments, functional element 1590 comprises one or more transducers, as described hereabove.

With respect to FIGS. 1 and 1A, in various embodiments another optional functional catheter 1600 can also be included in system 10, e.g., for insertion into the heart H (or other anatomy) of the patient P. The optional catheter 1600 can be or at least include a diagnostic catheter, a mapping catheter, a treatment catheter, or a combination thereof. The catheter 1600 can comprise a shaft 1620 with a handle 1610 at its proximal end. At a distal end of shaft 1620 is disposed a functional array 1650 comprising at least one functional element. As examples, the functional elements of the treatment array 1650 of electrodes (or other functional elements) 1651, such as mapping, diagnostic, treatment, and/or localization electrodes or elements disclosed herein. In some embodiments, catheter 1600 comprises a lasso catheter, e.g., a mapping catheter biased in a looped configuration as shown.

Referring to FIGS. 1 and 1A, the patches 500 can be configured for placement on the body, e.g., torso, of the patient P. The patches 500 can be coupled to the console 5000 with one or more cables or cable assemblies 501, or other wired or wireless data transfer element or technology. The patches 500 can be skin-contacting patches including an adhesive for removable application to the torso of the patient P, and each patch can include one or more types of functional elements. The patches 500 can include at least one impedance patch 510 (such as a patch that measures and/or applies voltages or currents) having at least one impedance functional element configured to measure impedance at the patch, such as at least one impedance electrode 515. The impedance measurements can be used by console 5000 to perform localization of the impedance mode. The patches 500 can include impedance functional elements to apply the impedance field. The patches 500 can include at least one magnetic patch 520 having at least one magnetic functional element configured to measure a magnetic field, such as at least one coil 525. The magnetic field measurements can be used by console 5000 to perform localization of the magnetic mode. The patches 500 can include magnetic functional elements to apply the magnetic field. The patches 500 can include at least one ultrasound-based functional element, such as an ultrasound sensor and/or transmitter. Ultrasound signals received by and/or transmitted from the patches can be used by console 5000 to perform localization in an ultrasound mode, such as to detect the presence or position of body structures or devices applied to or inserted into the body, such as catheters or sheaths.

In some embodiments, the patches can be configured to be incorporated into a wearable garment or a portion thereof, such as a vest, suit, shirt, bodysuit. The garment can be made of a material that maintains contact, pressure, and/or position of the functional elements relative to the body. The garment can integrate materials with elastic or compressive properties to maintain contact, pressure, and/or position of the functional elements relative to the body. The garment can comprise a plurality of layers, and one or more functional elements or portions thereof can be maintained between on within such layers. The garment can be made of or include materials that are optically, electrically, and/or magnetically transmissive. The garment can be made of or include materials that are electrically conductive. The garment can include an outer surface configured to receive one or more of the patches.

In some embodiments, one or more of the patches 500 can be a combination (or "combo") patch including two or more different types of functional elements. FIGS. 1 and 1A show embodiments of different types of combo patches. As examples, a combo patch 550 can include at least one magnetic element and at least one impedance element, and optionally another type of functional element 599. For example, functional element could be a 12 lead EKG/ECG (electrocardiogram) element generally positioned on patient during procedure. As such, combo patch 550 can comprise an electrode 515 and a magnetic coil 525, similar to patches 510 and 520 respectively, and be configured to do all of the functions of patches 510 and 520, as well as EKG/ECG functions. Alternatively or additionally, system 10 can include one or more EKG/ECG leads (or patches) 560.

In various embodiments, any one or more of patches 510, 520, and 550 can include at least one other functional element 599. Beyond an EKG/ECG functional element, the functional element 599 can be or include, as examples, a generic sensor, transducer, and/or other functional element, e.g. accelerometer, sweat detector, physiologic sensor, and/or imaging marker (e.g., a radiopaque marker, an MR marker, an acoustically reflective marker). As other examples, in some embodiments, functional element 599 could be or include a microwave functional element, an ultrasound functional element, or a combination thereof.

In some embodiments, the patches 500 can comprise a porous material to form a porous conductive patch 500 that allows the patient's skin to breath, thereby mitigating perspiration and stabilizing impedance fluctuations. In some embodiments, a porous patch 500 can be totally immersed in a conductive "coating" material, such that the entire structure (of the patch) conducts, e.g., the "coating" can be for 3D structure rather than a 2D layer on the patch surface. In some embodiments, the conductive coating can comprise the same conductivity wet or dry, to avoid the need to impregnate the patch with a hydrogel to ensure conductivity with the skin of the patient P.

The various catheters 1000 and patches 500 can be coupled to the console 5000 via any of a number of wired or wireless devices and/or technologies. In various embodiments, console 5000 can include one or more processors and data storage devices useful for receiving, processing, and/or storing data and information from a plurality of external sources to perform improved localization of one or more apparatus relative to the body of the patient P. Additionally, in various embodiments, the console 5000 can be configured to drive, query, and/or control one or more external devices, such as the diagnostic, mapping, and/or therapeutic devices for the heart or other anatomy.

In the embodiment of FIG. 1, the console 5000 includes an imaging module 5010, a mapping module 5020, a treatment module 5030, and a user interface module 5050. The imaging module 5010 can be configured to provide, produce, acquire, update, store, and maintain at least one image of the heart or at least one cardiac chamber of the heart H. The imaging module 5010 can receive imaging information from at least one imaging device 50. The imaging device can be configured to gather anatomy information (e.g., heart anatomy information) from one or more image or imaging sources or systems, e.g., from a computerized tomography (CT) scan, fluoroscope, X-Ray, MRI, and/or an ultrasound imager.

In various embodiments, the console 5000 includes an imaging module 5010 that receives and stores image information from at least one imaging device 50. The imaging device 50 can be or include at least one of a magnetic resonance imaging (MRI) device, a fluoroscopy device, and or a source of a heart model. The imaging module 5010 can be configured to provide, generate, and/or update an anatomical model, e.g., of the heart H, based on the data and information received from the imaging device 50.

The console 5000 can further include a mapping module 5020 configured to receive cardiac activity mapping information from electrodes (e.g. catheter or patch electrodes) produces cardiac electrical activity map, wherein cardiac activity as one or more of voltage, surface charge, dipole density, etc.

The console 5000 can further comprise a treatment module 5030 configured to cause or drive the treatment catheter 1500 to deliver treatment energy to one or more locations of the heart H, which could be a closed-loop energy delivery based on mapping or other information produced by system 10. For example, the treatment catheter 1500 could be or include an ablation catheter of any of the types mentioned herein, known in the art, or hereafter developed, or the treatment catheter could be any other type of treatment apparatus otherwise known, e.g., drug or device delivery system or catheter.

The console 5000 can further include a user interface module 5050 configured to exchange data information with one or more user input and output components 60, such as a two-dimensional display, a three-dimensional display, a keyboard, a mouse, a touchscreen, a printer, a 3D printer, a communication system, and so on.

The imaging module 5010 can additionally or alternatively be configured to receive data and information from one or more ultrasound functional elements, such as UST elements 1153 on the catheters 1100.

In various embodiments, the console 5000 includes a localization subsystem 5100 that is configured to establish and maintain multiple localization modes. The localization subsystem 5100 can receive localization information from the patches 500 and catheters 1000 and process the information to produce device location information. The multiple localization modes can be combined, and these modes can include at least one of an impedance localization mode and at least one of a magnetic localization mode. In some embodiments, the multiple localization modes can additionally or alternatively include at least one ultrasound localization mode. In various embodiments, a first localization mode is an impedance localization mode established using one or more impedance electrodes 515 configured to sense impedance values associated with the patient P. From the impedance values, changes in impedance can be determined.

In various embodiments, the localization subsystem 5100 includes an impedance localization module 5110. The impedance localization module 5110 includes processing capabilities to implement an impedance localization mode. The impedance localization module 5110 can include an impedance signal generator 5111 configured to generate drive signals to drive impedance-based localization elements, such as electrodes 1151.

In various embodiments, the localization subsystem 5100 includes a magnetic localization module 5120. The magnetic localization module 5120 includes processing capabilities to implement a magnetic localization mode. The magnetic localization module 5120 can include a magnetic field signal generator 5121 configured to generate drive signals to drive internal and/or external magnetic coils, such as magnetic elements 1152. The console 5000 can also include or couple to an external fixed magnet 5125. The fixed magnet 5125 can be a fixed magnetic field generator and can take the form, for example, of a magnetic sensor that gives a fixed coordinate reference, such as at a surgical suite, surgical bed, patient, and so on. The magnetic localization module 5120 can receive information and data from or associated with the fixed magnet 5125, such as the fixed coordinate reference, to perform magnetic localization.

In various embodiments, the localization subsystem 5100 can optionally include an auxiliary localization module 5130. The auxiliary localization module 5130 can include an auxiliary localization signal generator 5131 configured to drive any signals needed for an auxiliary localization mode. The auxiliary localization mode can be an additional magnetic localization mode, an additional impedance localization mode, an ultrasound localization mode, or a microwave localization mode, as examples.

The localization subsystem 5100 can include a localization processor or processing module 5150 which produces device location information based on output of both the impedance localization processor 5110 and the magnetic localization processor 5120, and, optionally the auxiliary localization processor 5130, if present. For example, the localization processor 5150, using the impedance localization and the magnetic localization can locate catheters 1000 or portions thereof within the patient P and/or the heart H of the patient P.

In various embodiments, the console 5000, includes one or more elements for generating a distribution (e.g. a field) on, within, and/or throughout the body, and elements for measuring one or more characteristics of the distribution. For example, the distribution can be a voltage, current, magnetic, electromagnetic (e.g., RF, microwave), ultrasound, and/or pressure distribution. When the distribution is applied across and/or through a volume of the body, it encodes spatial information. That is, as the distribution varies as a function of position, various characteristics (e.g. values, rate of change, gradients, linearity, and/or orthogonality) of the distribution possess a relationship (e.g. a correspondence or mapped value) to spatial coordinates of the volume. The distribution follows the corresponding physics applicable to the energy modality generated. To estimate the distribution, a solution for unknowns within a set of one or more equations (e.g., field equations such as Maxwell's equations) following the physics of the problem can be established. This can be accomplished through a collection of measurements followed by computation or modeling of the field solution, with or without additional constraints, assumptions, or a-priori knowledge of one or more field characteristics or properties. In some embodiments, computation or modeling of the field solution to obtain the device location information can be a complete solution to the field problem. In some embodiments, computation or modeling of the field solution can be limited to a partial solution. For example, a partial solution can be limited to a geometric or spatial region (such as an anatomical region, such as a heart chamber). As another example, the partial solution can be limited to solving a set of field equations corresponding to a subset of all possible field characteristics (e.g. solving partial differential equations corresponding to the continuity of the field for characteristics such as the field gradient, while not explicitly estimating the field magnitudes).

In some embodiments, a field distribution can be generated by the impedance localization module 5110 by applying one or more electric or electromagnetic sources, such as a voltage or a current source. This application leads to generation of one or more corresponding field distributions, such as a voltage, current, and/or magnetic field generated through space. Measurements of the field distribution or corresponding properties of the space over which the field is applied (such as the distribution of local impedances across a volume, such as a patient's torso) can be performed using a set of one or more sensor elements, distributed at one or more locations within the field. The information from the sensor elements can be combined to estimate a quantitative description of the field and its characteristics (e.g., a model). For example, at least 3 sensors providing simultaneous recordings can be used to model a field with 3 degrees of freedom, e.g. a 3-dimensional field.

In some embodiments, the number of required simultaneous measurements can be reduced by taking advantage of known limits of the degrees of freedom of the field, or where the number of sensors uses a series of constrained or controlled measurements through time, such as through a controlled mechanical displacement of the sensor (e.g. a known series of maneuvers). As an example, using a single electrode, movement of the electrode over a known distance or in controlled directions (e.g., three cardinal directions for a 3D Cartesian coordinate system) can sufficiently sample 3D space in a short amount of time (e.g., seconds) and estimate the field. As another example, using a set of 2 or more electrodes with a known spacing (e.g., Euclidean distance, manufactured spacing), the two electrodes can be maneuvered to be oriented in three or more directions (e.g., three cardinal directions for a 3D Cartesian coordinate system), such as by deflecting, rotating, sweeping, retracting, advancing, or some combination of these. Some embodiments require only that the electrodes are oriented in three unique directions (such as directions separated by 3° or more), or that the set of sampled orientations contain enough unique directions to form two unique planes in 3D space. In some embodiments, a set of algorithms can be used to quantify the degree of directional sampling and provide feedback to the user as to the quality of the sampled data set. The feedback may be used to provide a visual indicator to a user that the sampling is sufficient, the sampling is insufficient, or how the user can optimally or efficiently complete the sampling to a sufficient level. In some embodiments, the sources and sensors as described above can be interchanged (sensors can remain in static positions while sources are distributed in or moved throughout space).

The following section describes an approach for simple, linear fields. The source(s) of the field (e.g., patches) can be optimally configured to reduce the degrees of freedom of the field. For example, a patch configuration (e.g., positions and/or orientations) that produces constant currents in the measurement volume can yield a linearly varying voltage field along the direction of the current (with parallel equipotential planes) such that a three-dimensional spatial description of this field can be fully obtained by 2 or more sensors distributed in space. Further, the generated field satisfies Maxwell's equations governing electromagnetic fields. Applying the same technique for a second, unique, current direction, requires only one or more additional sensors to be used. Applied, again, to a third, unique, current direction requires only a total of 4 or more sensors to obtain a model of three simultaneous but independent fields, each satisfying their independent set of Maxwell's equations. This configuration is one method for full, three-dimensional localization using three independent fields.

The following section describes an approach for satisfying the governing field equations for general field. A field established by applying current to the patches 500 from the surface of the body can be described by the following simplified Maxwell's equations:

$$\nabla \cdot (\sigma \nabla v) = 0,$$

through the volume and the corresponding boundary condition being $$J \cdot n = \begin{cases} 0, \text{ where current source is not present on the outer surface} \\ \text{applied current density, at the patches} \end{cases}$$

A complete solution to this problem that provides the distribution of the voltage field v in the body can be obtained with the knowledge of the boundary condition (J), which depends on the patches and their placement on the body surface, and the conductivity distribution σ of the body. A-priori knowledge of the patient specific boundary conditions and conductivity distribution can be challenging to obtain. A simplified model of the torso can be used to generate an approximate solution to this problem. This solution can be further augmented by a 3D model of the patient specific torso, for example, one obtained from a segmented CT and/or MRI image.

In some embodiments, to navigate an electrode in the heart, the distribution of the field in the heart needs to be estimated, thereby alleviating the need to know the surface boundary conditions, J. Since the conductivity of the blood pool is spatially constant, the governing equation simplifies to a Laplacian equation $\nabla^2 v=0$, thereby alleviating the need to know the conductivity distribution σ. The problem is therefore substantially reduced and can be solved with a reduced set of sensor measurements. Additionally, some tissue structures (a region of limited conductivity change) might produce negligible deviation of the field and therefore still fit the Laplacian equation. So the solution to the Laplacian equation can be applied accurately to these regions as well. For example, these regions can consist of thin conductive tissue structures (such as atrial walls). In some embodiments, the solution to the Laplacian equation can be analytically approximated by utilizing a Green's function:

$$\int_{volume} (\phi \nabla^2 v - v \nabla^2 \phi) dv = \int_{surface} (\phi \nabla v - v \nabla \phi) \cdot n ds \quad \text{(Equation 1)}$$

Here, the 'surface', with normal 'n', encompasses a 'volume' of uniform conductivity which satisfies the Laplacian equation. ∅ is a Green's function. In some embodiments, the design of the Green's function can be formulated such that:

$$\nabla \phi = 0 \text{ at the 'surface' and } \nabla^2 \phi \cong \delta.$$

The δ function's choice can be different from the traditional Dirac delta function, which leads to Green's function with singularities. The choice of this function can be optimized to deliver numerical stability (eliminating singularities) while maintaining high resolution of the reconstruction of the field distribution, for example by choosing a Gaussian pulse for δ. With the Green's function, as described herein, the solution to estimate the voltage distribution in the volume can be shown to be:

$$v = \int_{surface} (\phi \nabla v) \cdot n ds \quad \text{(Equation 2)}$$

With this Equation 2, and with an estimate (or measurement) of the term based on the gradient of the voltage (∇v·n) at the 'surface', the distribution of voltage v in the volume can be obtained. Estimation of the voltage gradient (∇v·n) can be accomplished by measuring a series of voltages in the 'volume' at known locations and formulating an inverse solution using equation 2. Alternatively, a Green's function can be formulated that works directly with the voltage term v, by ensuring ϕ=0 at the surface. This would enable measurements of the voltage v to be made directly on the surface. The voltage could be easier to measure, with a simple electrode, as compared to the gradient of the voltage ∇v.

The limitations of designing a Green's function can be circumvented by estimating a transformation that provides the voltages, in a desired region, as a function of a set of measurements (voltages or other field characteristics such as current can also be used) from a set of distributed points. The points at which measurements are obtained can lie within the desired region or outside the desired region. As the governing equation for the applied field is same for a variety of sources, a series of measurements made from simulations, analytical solution or experiments with a set of controlled sources (that ascribe to the same physics) can be used to estimate the transformation. The measurements needed to create the transformation consists of both the points at which voltages are known and the points at which the voltages are desired to be found.

The estimated transformation can then be used to predict the voltages in a desired region from measurements made at the locations used in the estimation process (points for which the voltages are known). This transformation would be capable of working with all the sources that ascribes to the same physics (that describes the controlled sources). This method can be extended to different configurations of points, at which voltages are measured (known), by storing the voltage generated by the controlled sources throughout the region of interest (that contains all the voltages used in the prediction process). When a new configuration of points with measured voltages are available, the transformation to obtain the voltage at all the other locations can be estimated from the stored values.

Simplifying the solution to a set of linear fields is advantageous because the number of measurements required to calculate a field model are reduced. One way to simplify to a set of linear fields is to measure the nonlinearities of the field and compensate for them. The nonlinearities can be estimated by methods described herein. The nonlinearities as seen from multiple sources applied to the patient can then be numerically combined (e.g., via addition, weighted addition, and/or nonlinear combination) to generate a field with minimal or at least reduced nonlinearity. This method then reduces the burden of accurately estimating the structure of the nonlinearity in the fields. The accuracy of the field estimation can then be limited to the extent needed to guide the combination of fields for reducing the nonlinearity, wherein the process could be iterative. A reduced burden on estimation could imply a reduced number of sensor measurements, noise requirements of measurements, etc. In addition to numerically combining fields generated by different sources, the placement of physical patches (e.g., patches of various sizes and/or shapes) at various locations can be guided based on this method.

Due to natural variations in the various parameters that govern the setup of the field, it can vary as a function of time. The change in various parameters could be due to physiological changes, such as the impedance of the torso, shape of torso, or artifacts such as change in interface between patch and torso or motion of the torso. At various time instances, the field distribution changes and if the change is substantial it can impact the localization process. At various time instances, the field can be said to be in a different state. The description of the field can then be updated for the various temporal states. The updates could be an adjustment or correction applied to the estimate or could be a different estimate based on the field state. The applicable field adjustment or the temporal states can be determined through measurements of various properties of the field or the medium in which the field persists. These measurements correlate to the state of the field. A process of creating consistency, stability, and accuracy between the field in its various states is termed as applying a 'reference'. In various embodiments, the application of a reference of the field, to make it consistent through various temporal states, can be performed using an adjustment to the sensor measured signals. The adjustment could be from a measurement or a series of measurements from various sensor locations. The measurements from these sensors can be used to extract an adjustment signal corresponding to the temporal profile of the change in the field. When 2 or more fields are applied, the different fields can be used to increase the redundancy in the localization process and can be then used to correct various artifacts. For example, impedance and magnetic field sources can be both applied to create a localization system with each energy modality. The signals measured by the electrode/magnetic sensor belonging to the 2 different energy modality can be described as follows:

$$S(t) = \text{Position}(t) + \text{Physiology}(t) + \text{Artifacts}(t)$$

Where 'S' is the measured sensor signal which changes as a function of position of the sensor and other physiological and external (e.g., artifact) factors that impact the field. Now, the physiological changes are experienced by both the magnetic and the electric field simultaneously (e.g., respiration). This impact allows for describing the Physiology(t) part of the signal between the two modalities as follows:

$$\text{Physiology}_{one\ magnetic\ sensor}(t) = [\text{Physiology}_{group\ of\ electrical\ sensors}(t)] \times [trs1]$$

$$\text{Physiology}_{one\ magnetic\ sensor}(t) = [\text{Physiology}_{group\ of\ magnetic\ sensors}(t)] \times [trs2]$$

$$\text{Physiology}_{one\ electrical\ sensor}(t) = [\text{Physiology}_{group\ of\ electrical\ sensors}(t)] \times [trs3]$$

$$\text{Physiology}_{one\ electrical\ sensor}(t) = [\text{Physiology}_{group\ of\ magnetic\ sensors}(t)] \times [trs4]$$

Additionally, for magnetic and electrical sensors (one or more) that are physically coupled we have:

$$\text{Position}_{magnetic\ sensor} = \text{Position}_{electrical\ sensor}(t) \times [trs5],$$

where [trs1], [trs2], [trs3], [trs4] and [trs5] can be estimated either from training data from the current patient during a case, or a computational model can be generated to estimate these transforms. The computational model can also be estimated by pre-collected clinical data from another set of one or more patients or with bench top measurements. These transformations represent (or are derivable quantities of) the solutions to the electric and magnetic fields applied to the body. The physiological signal of the electric and magnetic field is connected by the volume conductor problem (e.g., physics governing the fields applied to torso). These transformations then co-register the 2 localization systems. This allows elimination of any disturbance on one or the other energy modality based system that does not fit the model. These variations can be caused by, for example, physiological drift or magnetic field disturbances or patient motion.

The various transformations can be estimated by relying on specific signatures (temporal/spatial/frequency) within an energy modality to separate the various factors. For example, from signals measured in a clinical case, frequency separation can be performed to separate individual contributors to signals from an energy modality. Modelling of the fields can also be used in the creation of the transformation functions. Additionally, specific steps, such as controlled motion of the sensors or source, controlled field disturbance, and the like, can be performed to estimate the transformation.

As an example, the transformation shown above is that of linear combinations, however other forms of transformation can also be employed. These transformations are governed by the physics of the problem.

In various embodiments, the spatial description of the field can be used to estimate the position of a sensor. The description of the field is an estimate of the spatial distribution of a certain characteristic of the field, such as voltage values of an impedance localization field. A sensor measurement can be converted through processing into the characteristic of the field that is estimated to be used in decoding the position of the sensor.

The transformations and/or field properties used by system 10 to describe the field can be estimated at particular cyclic time points of the patient's physiological variations (e.g. heart and/or respiration cycles), such as time points during which the complexity of the field is minimal (e.g. to simplify modeling). At these particular time points, due to favorable physiological conditions, the applied field demonstrates reduced spatial non-linearity which allows for an easier description of the field and with lesser inputs. In some embodiments, these time points are temporally located proximate the T wave and/or P wave of the ECG signal. Additionally, measuring the signal at a particular time instance over a wider period of time can lead to constancy of the source. The constancy has a cycle that matches the time period of observation, and contributions to the signal changes from other sources can be observed within these measurements. Transformations (e.g. models) describing these other sources can be estimated based on the observations.

In some embodiments, an artifact in a recorded signal can comprise a discrete impulse (e.g. caused by a short, high amplitude extraneous signal, such as a pacing pulse). This discrete impulse can produce a waveform comprising a component with a "sharp" structure (e.g. a waveform with a steep leading and/or trailing edge). When such an artifact is present on a localization signal (e.g. an impedance-based localization signal recorded by an electrode to be localized), a short "jump" in the determined position of the recording electrode can be observed by system 10. In some embodiments, system 10 includes a thresholding algorithm based on observing signal variations during a non-artifact period. The thresholding algorithm can be configured to limit the observed jump in the position of the recording electrode or electrodes. For example, median filtering of the signal with a filtering period comparable to and/or greater than the length of the extraneous signal causing the artifact can also be used to limit observed positional shift. In some embodiments, by applying one or more additional filters to this signal comprising a component with a sharp structure, system 10 filters the artifact sufficiently to be negligible to observe (e.g. the jump in the position of the recording electrode is negligible after two or more filters are applied). The process of limiting a sharp structure in a recorded signal by applying a first filter (e.g. a median filter) prior to a second filter can help prevent such a sharp structure from manifesting as an observable jump in the localized position of catheter. In some embodiments, when a pacing pulse is delivered via an electrode (which is also being localized using impedance localization), an artifact caused by the pacing pulse can be substantial, and in some embodiments, this artifact can be sufficient to saturate the localization recording circuitry. This saturation and/or significant change in recorded signal amplitude can be used by system 10 to readily detect the presence of pacing on a channel, such that system 10 can ignore those signals recorded while the pacing is present, or otherwise filter the signal such as to avoid negatively affecting the localization of one or more other electrodes being localized while the pacing is present.

In various embodiments, the console 5000 can include a transformation (such as a scale matrix) 5155 that translates raw localization information to a position relative to an anatomic model 5255, which can also form part of console 5000 or can be external to console 5000. The scale matrix 5155 is a measure of rate of change a field value (e.g., rate of change of voltage of an impedance field) and it is a specific example of a field characteristic that can be used in the localization process. The process of localization using a scale matrix allows for a simple linear operation to estimate the position of the sensor. A simple linear operation allows for better numerical stability within the computational process. The process of estimating the location of a sensor involves measuring the difference in the field value (e.g., voltage) between the sensor and a location (e.g., a location whose position with respect to the anatomy and field value is known). The measured difference is then multiplied by the scale matrix and the resultant output of the process is the position of the sensor with respect to the known location. The scale matrix 5155 is formed of localization data that can be adjusted or corrected based on at least one reference point or frame of reference, such as is described in detail herein.

In various embodiments, the console 5000 can include an anatomy subsystem 5200 that receives anatomy information from the diagnostic catheter 1100 and produces an anatomic model of the heart H or portions thereof. The anatomical model produced can include information received from the external imaging device 50 via imaging module 5010, in some embodiments. The anatomy subsystem 5200 can be configured to update the anatomical model in real-time, near real-time, or from time-to-time. In various embodiments, the anatomy subsystem 5200 can include an ultrasound module 5210 and an ultrasound signal generator 5211. The ultrasound module 5210 can be configured to drive/record ultrasound transducers of the first diagnostic catheter 1100, and can drive any other ultrasound transducer elements of the system 10, e.g., functional elements 1153. The ultrasound module 5210 can use the ultrasound signal generator 5211 to generate ultrasound drive signals to excite ultrasound transducers of the catheter 1100 and, more generally, the system 10.

The anatomy subsystem 5200 optionally includes an anatomy import module 5220 that receives anatomy information from the external imager 50 and "combines" the information with information from the ultrasound module 5210 to create an "enhanced" anatomic model 5255, e.g., with improved accuracy and/or resolution.

Figure 3:
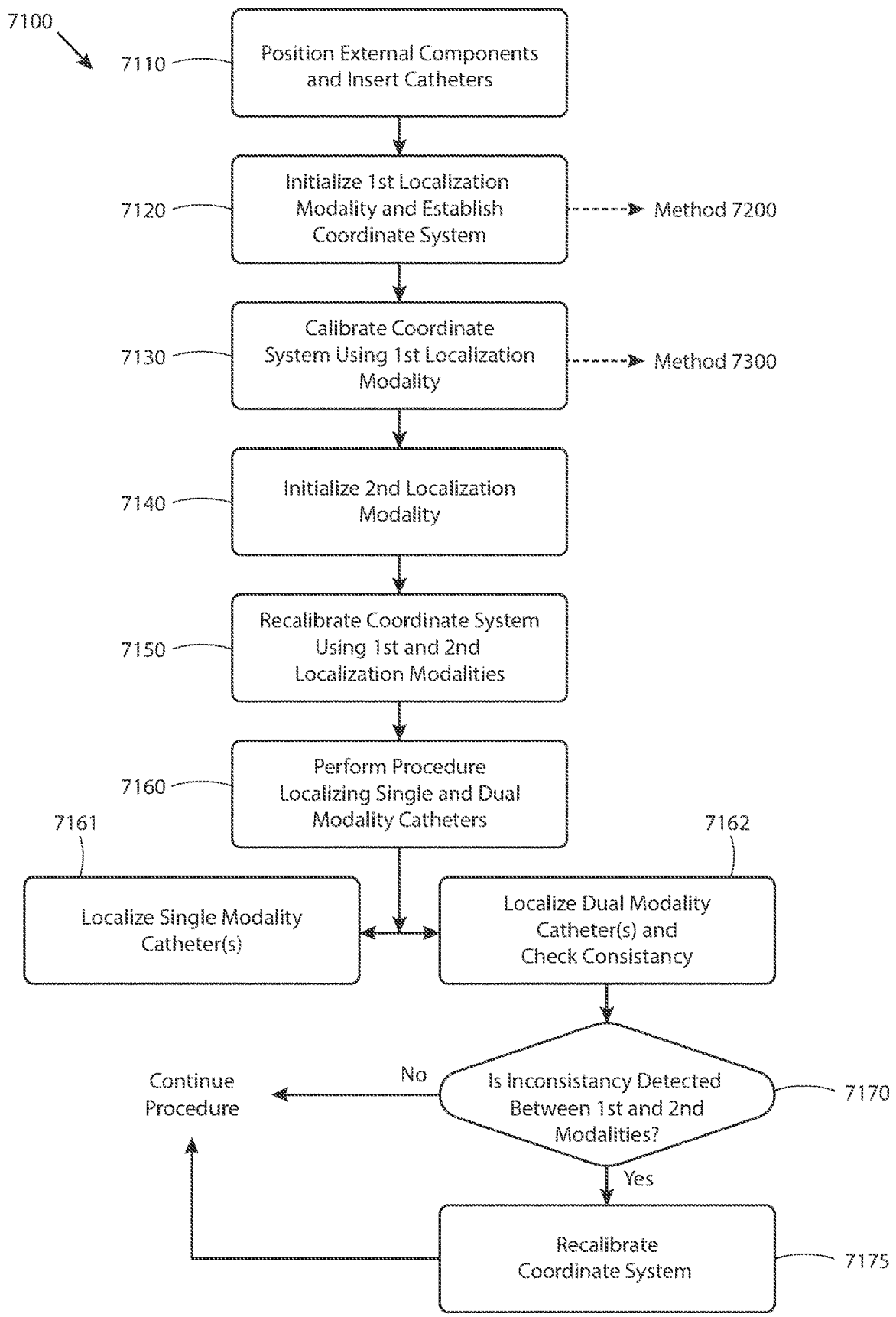
FIG. 3 illustrates a flowchart of an embodiment of a method for initializing, calibrating, and/or correcting a localization system, consistent with the present inventive concepts.

FIG. 3 illustrates a flowchart of an embodiment of a method 7100 for initializing, calibrating, and/or correcting a localization system, consistent with the present inventive concepts. Various data storage, processing, and generation portions of method 7100 can be carried out by console 5000 of FIG. 1, or components thereof.

In step 7110, external components are positioned and one or more of catheters 1000 is inserted into the patient P. In various embodiments, a first localization mode is initialized and a coordinate system established, then a second localization mode is initialized and the coordinate system is recalibrated using the first and second localization modes. The coordinate system is established to provide a frame of reference for localizing devices within the patient P.

For example, in an embodiment, a first localization mode could be the impedance localization mode and a second localization mode could be the magnetic localization mode. Initializing the impedance localization mode can include applying the external patches 500 to the torso of the patient P, where the patches 500 include at least impedance electrodes 515. Then, the second mode of localization, the magnetic localization mode, can be setup. Initializing the magnetic localization mode can include applying the external patches 500 to the torso of the patient P, where the patches include at least magnetic elements 525. That is, in various embodiments, impedance patches 510, magnetic patches 520, and/or combo patches 550 could be used. The fixed magnet 5125 could also be positioned, such as beneath a table supporting the patient P. Step 7100 can also include inserting one or more of the catheters 1000 into the patient P, wherein such catheters include elements useful in establishing at least one of the two localization modes, e.g., impedance and magnetic. For example, either one or both of the diagnostic catheters 1100/1200 could be inserted into the body of the patient P to initialize and calibrate one or more localization modes.

Figure 4:
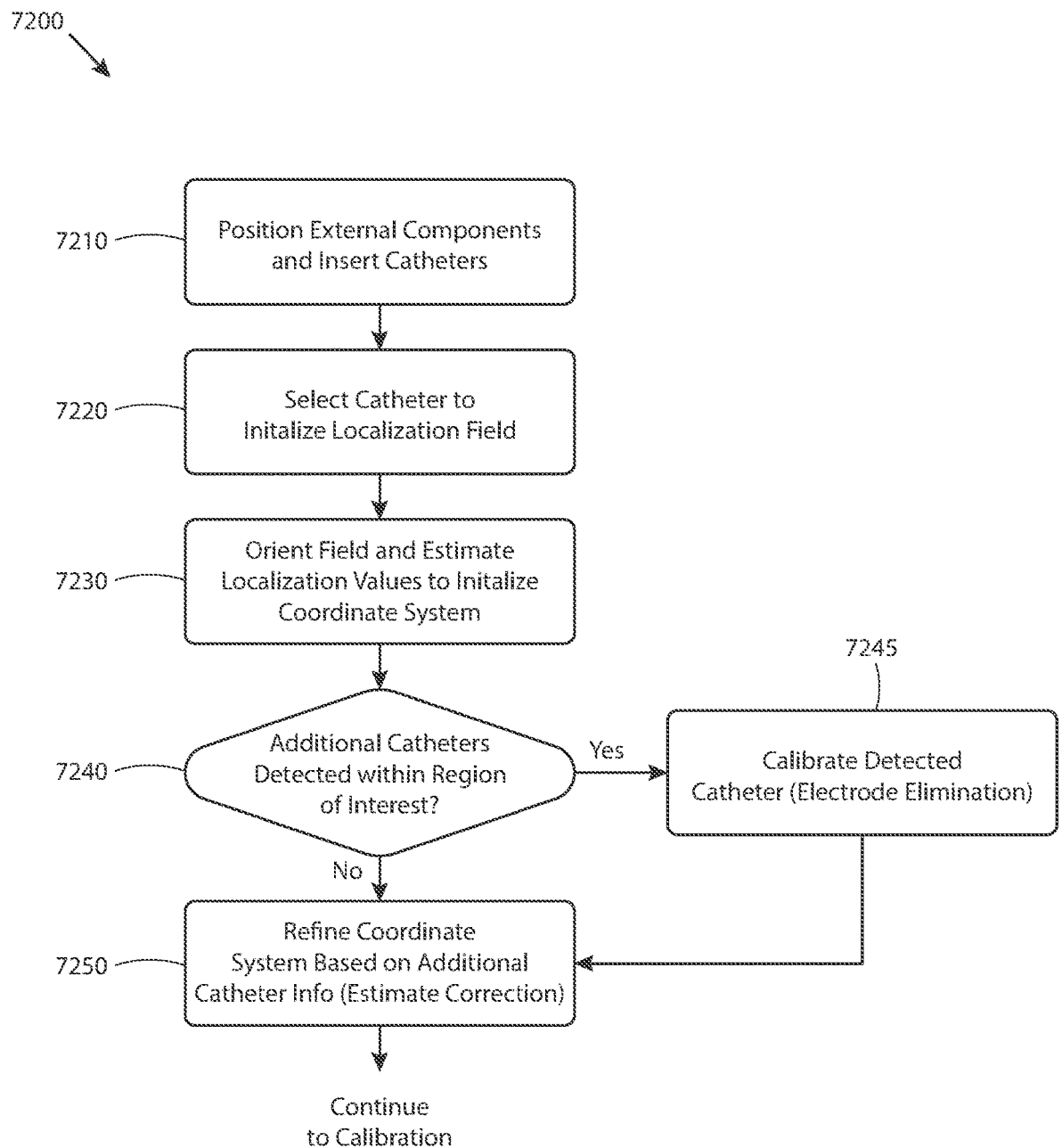
FIG. 4 illustrates a flowchart of an embodiment of a method of initializing a coordinate system within the body, consistent with the present inventive concepts.

In step 7120, with the physical patches 500 and catheters 1000 in place, the first localization mode is initialized. Initializing the first localization mode includes activating various localization components, such as electrodes 515 for the impedance localization mode or magnetic elements 525 for the magnetic localization mode, to establish the coordinate system within the patient P. That is, patches 500 can be used to generate signals that establish a three dimensional coordinate system (X, Y, Z). The coordinate system is established to determine the position of, i.e., to localize, catheters and elements of the catheters within the patient P. FIG. 4 provides an embodiment of the method 7200 that could be used to accomplish step 7120.

In step 7130, the coordinate system is calibrated using the first localization mode and an inserted catheter, such as catheter 1100 having basket array 1150. FIG. 4 provides an embodiment of a method 7200 that can be used to accomplish step 7130. According to the method, the established coordinate system is initially calibrated so that localization can be performed. The calibration can be used to determine the initial scale of the X, Y, Z axes of the coordinate system and the origin of the coordinate system with an initial assessment of a region where localization of sensor will be applied (e.g., in a cardiac chamber).

In step 7140, the second localization mode, e.g., the magnetic localization mode, can be initialized. Initializing the second localization mode in this step presumes that physical placement of magnetic elements relative to the patient P has been accomplished in step 7110, such as the magnetic elements 525 of patches 500. However, if placement of the magnetic elements necessary for performing the second localization mode has not been accomplished, then they can be accomplished in this step. The magnetic elements are activated or energized to initialize the magnetic localization mode. The method 7200 of FIG. 4 can be adapted to initialize the magnetic localization mode.

With both localization modes initialized, the coordinate system is recalibrated using the first and second localization modes, in step 7150. That is, the coordinate system can be calibrated with the first localization mode and then with the second localization mode. Differences between the two calibrations can be resolved mathematically to generate a single calibration of the coordinate system. Further, the fixed magnet 5125, can be used to establish a reference point or a fixed magnetic field with respect to the room (or other volume) which establishes a coordinate system independent of the position of the patient P. The information from the fixed system can be used to ascertain an adjustment to the coordinate system setup by the patches on the patient's torso. These adjustments maintain the calibration of the localization throughout the procedure. As an example, the need for such an adjustment could be due to the shape of the patient's torso changing during the procedure, e.g., with respiration.

In step 7160, the coordinate system has already been established and calibrated using the first and second localization modes. Therefore, processes are executed in step 7160 to localize a device (e.g., a catheter 1000) within the coordinate system using a single localization mode and/or using both localization modes to localize the device. Step 7160 includes sub-steps 7161 and 7162. Sub-step 7161 includes localizing a catheter using a single localization mode, i.e., impedance localization or magnetic localization. Sub-step 7162 includes localizing at least one of the catheters 1000 using two localization modes, e.g., impedance localization and magnetic localization. This can be referred to as dual mode localization. In either case, localizing a catheter includes determining a location of the catheter or its functional elements within the patient P and within the coordinate system as a frame of reference. To localize the catheter, functional elements of the catheter are used to record signals. For example, electrodes on a catheter or a sheath can be used to record localization signals being emitted into the patient P by one or more patches 500 for impedance localization, as in sub-step 7161. At least one magnetic element on the catheter or sheath can be used to record (or sense) a magnetic field being generated, such as by one or more patches 500, to localize the catheter using magnetic localization. Alternatively or additionally, to localize the catheter, functional elements of the catheter or sheath can be energized to become sources of signals. For example, electrodes on a catheter can be considered sources of voltages that can be localized using impedance localization, as in sub-step 7161. At least one magnetic element on the catheter can be energized to generate a magnetic field and localized using magnetic localization. For catheters enabled with both impedance and magnetic functional elements, both localization modes can be used to localize the same catheter with respect to the same coordinate system, as in sub-step 7162.

With respect to localization using two modes (or dual mode localization), the magnetic field-based localization mode is not impacted by variations in the impedance of the body. In accordance with aspects of the inventive concept, it is desired to have a magnetic localization at least as a means of augmenting an impedance-based localization system. In various embodiments, the magnetic localization mode can require an electronic subsystem or components different from those used in impedance localization to generate and measure the magnetic fields.

In various embodiments, the currents generating the impedance field could be sent through coils 525 created in-line with the patches 500 (e.g., in-line with patch electrodes 515) to generate the magnetic field and the same method for measuring the impedance fields in the electronics can then be used to also measure the magnetic fields.

A magnetic sensor (e.g. one or more coils 1152 of basket 1150) could be included on the device being localized. The drive coils/sensors could include a magnetic material (ferrite) added for improved sensitivity. The various coils 525 created in-line with the impedance electrodes 515 can be organized on the body for optimal sensitivity for the localization of the device (e.g., basket array 1150) in the body.

While still using the same receive method as is used with the impedance electrodes 515, the drive coils 525 generating the magnetic fields could be driven with higher currents to achieve improved sensitivity for the magnetic localization. This method generates higher currents applied to the coils 525 and the lower current applied to the impedance localization patch electrodes 515, which could be accomplished through splitting the power output from the driver electronics of the console 5000 or having second driver electronics. Power splitting schemes can be based on the design of the impedance of the coil, patch, and/or the interface connecting these elements. These methods can be based on frequency of field, and/or a combination of the measurement of nominal torso impedance with respect to the impedance of the coil (which could also be augmented with a coupling circuit to optimize the power splitting process) to direct the output power to various elements.

In step 7170, the console 5000 checks the consistency between the results in sub-step 7162, e.g., localization results for catheters localized using both impedance and magnetic localization. The inconsistency can be determined by assessing a location of a device or functional element within the coordinate system determined from each localization mode. If there is an inconsistency determined in step 7170, the method moves to step 7175 were a recalibration procedure is performed, which could include returning to step 7130 or step 7150 to again calibrate the coordinate system. But if there is no inconsistency, or the inconsistency is within acceptable limits or below an established threshold, then the system 10 can be used to perform a procedure, e.g., a diagnostic and/or a treatment procedure, using impedance and magnetic modes of localization for devices used in the diagnostic and/or a treatment procedure. Localization using both localization modes can continue during such procedures.

FIG. 4 illustrates a flowchart of an embodiment of a method 7200 of initializing the coordinate system within the body of the patient P, consistent with the present inventive concepts. Various data storage, processing, and generation portions of method 7200 can be carried out by console 5000 of FIG. 1, or components thereof. The method 7200 of FIG. 4 can be used to implement the method step 7120 of method 7100 of FIG. 3. The method of FIG. 4 could be used for the impedance localization mode (step 7120) or the magnetic localization mode (step 7140).

In step 7210, the external components, such as patches 500, are positioned on the patient P and one or more of the catheters 1000 are inserted into the patient P. In various embodiments, the localization patches 500 are intended to be placed on the body of the patient P such that the resulting set of field vectors are roughly orthogonal and form a right handed (RH) coordinate system. Once the patches 500 are applied to the torso, an RH system can be established from the measured voltages. The generated voltages follow the temporal pattern of the applied source which can be a DC, AC, and/or pulsed field (DC/AC) source. The voltage measurement method can determine the sign of the measured values. For example, in case of an AC field, the measured value of the created AC voltage can be either positive or negative based on the phase of the applied waveform at which the measurement is made. The change in sign of voltage can invert the axis with respect to the physiological coordinate system. The process of computationally determining the orientation of the localization system with respect to the patient is called auto-orientation. At the first portion of auto orientation, the sign of the voltages is established to create the desired axis directions. This auto orientation can be performed according to the following steps. The direction of change in voltage between electrode pairs placed in a known orientation with respect to the localization axis can be used to establish the direction of the axis. The ECG leads can be placed at various fixed locations on the body with respect to the heart. This placement gives the collection of electrodes a known orientation with respect to the cardiac chamber. This orientation can be used to establish the directions of the coordinate axis. In the current implementation, the localization X axis spans the left-right direction of the body, and the ECG leads V5 and V6 are to the left of the heart chamber. The voltages from these leads are then compared to the voltage of an electrode from the cardiac volume to establish the direction of the X axis.

The position of reference electrode/patch for the localization system is next to one of the patches creating the Y axis, on the lower back. This placement fixes the origin of the Y axis on the lower back. The voltage at this location would be zero; and, from comparison to the voltages from catheters placed in the vicinity of the heart, the orientation of this axis can be established.

The position of various internal electrodes with respect to each other can be used as well. For example, the unipolar electrode place in the lower IVC is along the inferior direction with respect to the heart.

The voltage differential between patches are a function of the direction of the demodulated current and impedance. By observing this voltage differential the orientation of the axis can be established.

A spatial coordinate system that satisfies the right hand rule can be used. This rule provides an additional condition to establish the directions of the coordinate system. The currents flowing between the patches indicates the direction of the patch orientation, which in-turn establishes the direction of the localization axis. In the present implementation, the right-handedness condition is used with the estimated direction of the currents from the 3 axes in the cardiac chamber to fix the direction of the Z axis.

Additional approaches to determine magnitude inversing can be based on voltage vectors on pre-grouped electrodes 1151 on the basket 1150 used to determine the direction. As shown above, the basket electrodes 1151 can be seen as Z-axis direction from the spline 1157 bottom to spline 1157 top. This direction is represented by pairs of the first and the last electrode 1151 on each spline 1157, and second and last second pairs on each spline 1157 for backup. For the X-Y plane that is perpendicular to the Z-axis, four symmetrical and opposite electrodes 1151 on selected splines 1157 are grouped to represent the X-direction and Y-direction, each with a pair of electrodes 1151. It is generally preferred to use the pair of electrodes 1151 farthest apart from each other to calculate the Z-direction.

For example, the search for two pairs of electrodes 1151 for the X-axis and Y-axis directions can start from the bottom up (bottom of spline 1157). Whenever these four electrodes 1151 are good nodes, they are chosen for determination of the direction. That is, if the 4 electrodes 1151 at the bottom are good nodes, they will be used for the calculation. In some instances, when these electrodes 1151 are close to each other, noise could obscure the calculation. The console can be configured to search the two pairs of electrodes 1151 from the middle (of each spline 1157) down and up, alternatively, to find the electrodes 1151 that are all good nodes and to determine the X- and Y-directions using those electrode pairs. In this way, two pairs of good-quality electrodes 1151 farthest apart from each other will be used to calculate the direction, resulting in a more robust approach that mitigates the possibility of noise.

In step 7220, a catheter, e.g., catheter 1100, is selected to initialize the localization field. That is, in some embodiments, a single catheter, e.g., a diagnostic catheter, can be used to initialize the calibration field and reliably establish a coordinate system to be used for localization. This catheter, when located within the heart H, sets up the origin of the coordinate system. This system can be then used to determine if additional catheters are in the vicinity of the heart. From this preliminary catheter, an initial calibration of the field can also be established. An initial calibration can involve an estimate of the scale matrix 5155. Consequently, the initial scale and the nominal expected shape of a catheter can be further used to detect if additional catheters are in the region of interest.

In step 7240, the console determines if additional catheters are detected within the region of interest, e.g., within the initialized coordinate system. If another catheter is detected, the method proceeds to step 7245 where the calibration is continued using the detected catheter. The calibration can be performed to eliminate electrodes on the catheter that are not functioning properly or at all. If no additional catheters were detected, the method proceeds directly to step 7250. The method also proceeds to step 7250 from completion of step 7245, if performed. Step 7250 includes refining the coordinate system based on the additional catheter information, if any.

Figure 5:
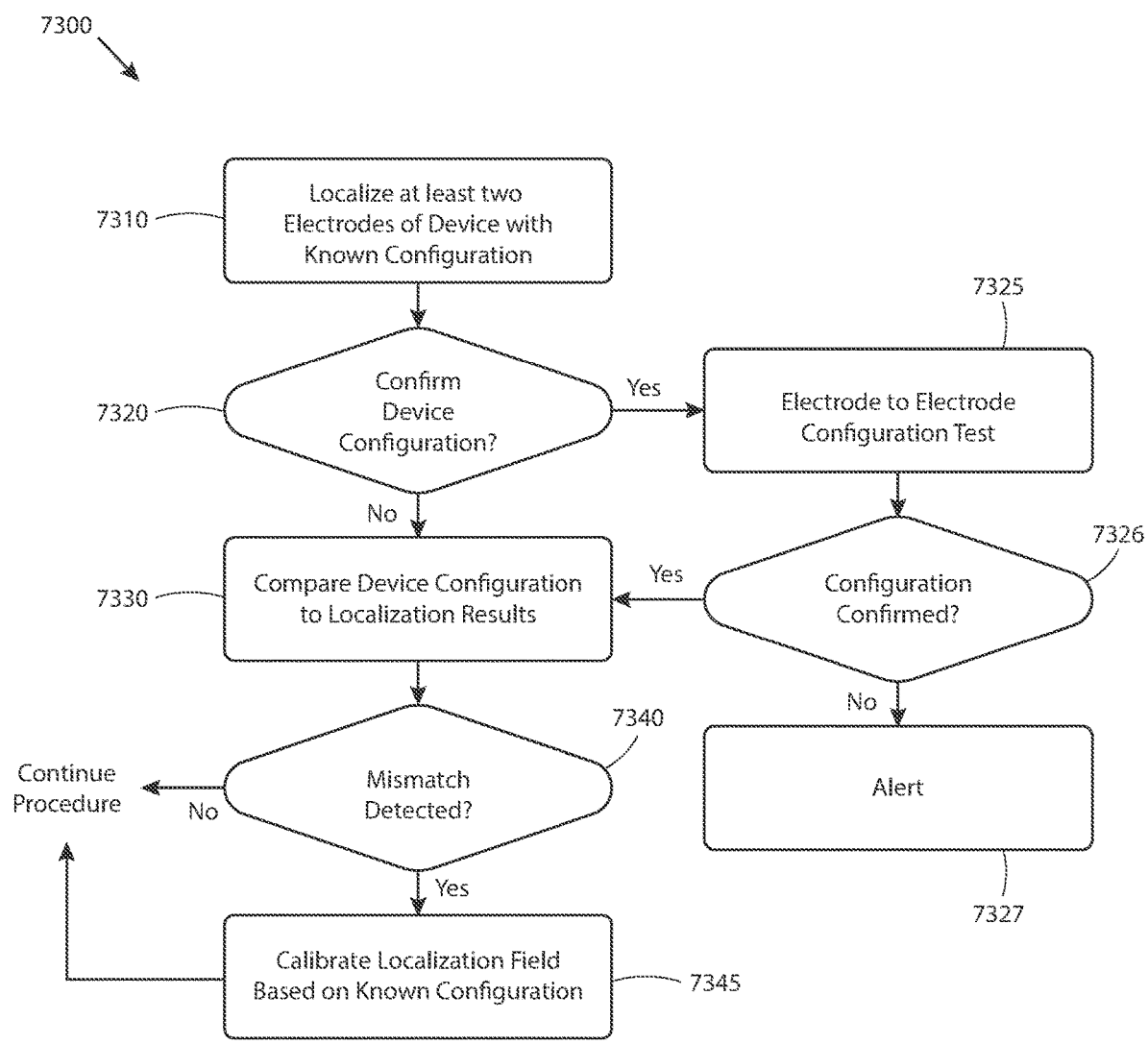
FIG. 5 illustrates a flowchart of an embodiment of a method of localization calibration, consistent with the present inventive concepts.

FIG. 5 illustrates a flowchart of an embodiment of a method 7300 of localization calibration, consistent with the present inventive concepts. Various data storage, processing, and generation portions of method 7300 can be carried out by console 5000 of FIG. 1, or components thereof. The console 5000 may have local or remote access to a predefined catheter configurations, e.g., for different basket arrays or other catheter types. As an example, the device could be basket array 1150 of catheter 1100, which comprises a plurality of electrodes 1151. Console 5000 may select a known device configuration for the catheter, e.g., basket array 1150.

Localizing at least two of the electrodes 1151 can confirm that the catheter has a particular basket configuration. In step 7310, the system 10 localizes at least two electrodes of the device.

The localization process for producing the field characteristic, such as scale factors, can be dependent on basket dimensions and shape (e.g., basket array 1150 of catheter 1100), but manufacturing variance and sheath deflection (e.g., sheath 1300) may alter the actual shape from the default shape. If the device shape is not well known, then the localization results are adversely affected. In addition, system outputs that depend on reliable knowledge of the position of various sensors (with respect to each other or anatomy) could also suffer from errors in localization and device shape model.

In various embodiments, the console 5000 has a set of predetermined or known catheter shapes (e.g., basket array 1150 shapes) and the method includes estimating a scale factors by finding which one of the known basket shapes optimizes the system performance. Basket 1150 shape and scale factor optimization for localization are, therefore, determined.

Scale matrix 5155 can be used for localization voltage to spatial position conversion. The scale matrix can be estimated by measuring voltage differences between electrodes with known spacing. This can be accomplished by measuring voltages of a catheter whose dimensions can be predetermined. For example, a mapping catheter 1100 having a known shape can be used for this purpose. However, the estimation of the scale matrix 5155 is susceptible to differences in the predetermined catheter shape and the actual catheter being used.

A series of scale factors can be initially estimated. For example, a series of predetermined catheter shapes can be used to generate a series of scale factors. The use of the correct scale factors can minimize the error in various system outputs which depend on having a reliable localization of catheter. This error can be used to determine an optimal scale factor to be used. Examples of system outputs that could be used are as follows: (1) shapes and/or dimensions of catheters or electrodes with known spacing, e.g., collapsed basket array 1150 could have a known inter-electrode spacing; (2) ultrasound point cloud; and (3) consistency in imaging of focal sources (ultrasound or electric).

Ultrasound-based basket shape detection can also be used to determine basket 1150 shape. The ultrasound point cloud is a representation of ultrasound values in three-dimensional space, where the values can indicate the presence or absence of an object a particular point in the 3D space. Measurement of the shape of a catheter (e.g., shape of basket 1150) is needed for understanding spatial variations in the various measured signal. These signals could be electrical signals, such as biopotential or localization signals. For example, within localization, the shape of the catheter is used to establish a scaling (scale matrix 5155), which gives the conversion from the voltage field to spatial distribution. Errors in predicting the shape of the catheter could lead to errors in localization of the catheter due to impact of the scaling factor.

Catheters that have ultrasound transducers (e.g. ultrasound transducers 1152 on basket 1150) on them can be used to measure the shape of the catheter. This could be done by measuring an ultrasound pulse from another transducer. If the transducers 1152 are facing away from each other (even under the condition of not being fully opposite), ultrasound signals that leak out of the backplane can be measured by the transducers 1152. A lower frequency ultrasound signal can also be used for this, due to the efficiency of backplane in attenuating ultrasound signal goes down with frequency. This could make detecting the signal through the backplane easier. The resolution of estimation of the position of the transducer 1152 can still be maintained while going to a lower frequency as the method involves a single source whose temporal/spatial transfer function through the backplane is known and/or measured. The resolution of detecting the position of the source can be high, even with a lower frequency, using methods such as phase locked detection, and/or template matching with the expected transfer function.

Catheter shape can also be determined by applying sources to various electrodes. These sources can be an electric/electromagnetic source applied at specific electrodes (e.g., at least 1 electrode). These sources produce a distinct field structure. This field structure can be used to determine the shape of catheters. Further, measurement of this field by electrodes with known positions can enhance the estimation process by providing additional independent inputs. The measurement from these electrodes could be used as a reference to guide the estimation of the catheter shape.

Additionally, information about the state of an electrode can be determined by making additional measurements. The state of an electrode can include, for example, contact with an object or structure (such as tissue), lack of contact with an object, intermittent contact with an object, orientation of the electrode relative to an object, and/or gross or detailed geometry of a nearby structure. In some embodiments, this determination can be achieved by applying sources to one or more electrodes and measuring the change in a property at or between nearby electrodes (such as impedance change, field potential, or current amplitude or density). For example, the system can determine that an electrode is in contact with tissue at a moment in time by sourcing a current from the electrode and sinking the current at an adjacent electrode while measuring the voltage at each electrode to determine the impedance between the electrodes. When either electrode comes in contact with an object or structure such as tissue, the impedance will change. Detection of the change in impedance between electrodes would indicate contact with tissue. Additionally, when a source is applied between two electrodes, the distribution of the field generated by the source depends on the impedance distribution of the medium. By measuring the field at a few positions, as described above, an estimate of the field distribution can be obtained. This information can then be extended to estimate the impedance distribution of the medium. Alternatively, the impedance distribution of the medium can also be estimated directly from the measurements. Once the distribution of impedance is estimated, tissue structures that show change in impedance can be reconstructed as well and useful information such as the proximity of an electrode to a tissue structure and the like can be determined.

Further, by applying a source-sink scheme among a set of several electrodes (e.g., continuously or iteratively; simultaneously or sequentially) the system can dynamically determine the state of tissue contact at each of the electrodes in the set. In some embodiments, the set of impedance measurements can be used to calculate not only direct contact of one or more electrodes with tissue, but also proximity of electrodes to tissue. In some embodiments, the state of tissue contact or tissue proximity can be used to provide feedback to the user, or it can be used in conjunction with other functions of the system to refine or augment the information calculated by the system or presented to the user. In some embodiments, tissue contact can be used to establish or refine the display of an anatomical object by using only anatomical data from an electrode that possesses simultaneous state information, such as contact with tissue or rejecting anatomical data that lacks such state information. In some embodiments, the creation of an anatomic structure can be established using tissue proximity detection from a network of electrodes.

In some embodiments, the source-sink scheme can be performed with more than one frequency if the sensitivity or specificity of one or more states vary as a function of frequency. For example, if two different tissue types respond similarly to one frequency, but differently to a second frequency, contact with or proximity to the two tissue types could be differentiated by evaluating the response at both frequencies. The two frequencies can be delivered simultaneously or sequentially. Additionally, since all tissue types have a capacitive and resistive component to their impedance, the capacitive portion responds differently to different frequencies and this can be used to further improve the information extracted by using impedance as the contrast property between different states, such as proximity to tissue.

The method moves to step 7320 where a determination is made of whether the device configuration from step 7310 should be confirmed based on localizing the electrodes. An affirmative indication sends the process to step 7325. In step 7325, an electrode-to-electrode configuration test can be performed to confirm the device configuration, e.g., the shape of basket array 1150. Additionally or alternatively, ultrasound or other configuration tests can be performed in step 7325, as described hereabove. In an embodiment of step 7325, one electrode 1158*a* on the catheter shaft just proximal to the basket 1150, and two electrodes 1158*b,c* placed on the basket actuator 1121 (i.e., the shaft which expands or collapses the basket) can serve as rulers in the localization field by which the basket's state of extension and shape may be estimated (as shown in FIG. 2). The two electrodes 1158*b,c* on the actuator 1121 are always separated by a fixed distance, because the actuator 1121 is linear and relatively rigid, in this embodiment. The voltage offset between these electrodes V(1, 2) is compared to the voltage offset between one of the actuator electrodes 1158*b,c* and the shaft electrode 1158*a* V(1,3). Scaling the known separation of the actuator electrodes 1158*b,c* by the ratio of voltage V(1,3) to voltage V(1,2) provides an estimate of the position of the actuator 1121 relative to the catheter shaft 1120. Tables of basket shape versus actuator extension may be interpolated to provide the shape of the basket 1150 (with electrode 1151 location, ultrasound transducer 1153 location, and ultrasound vector orientation) in any state of extension. Equivalently, two fixed electrodes on the catheter shaft and a single electrode on the actuator 1121 may serve the same purpose.

In various embodiments of step 7325, the sensor measurements from a group of sensors with certain coupled aspects of their position can be used to determine the quality of a measurement or a sub-group of measurements. Based on the quality of the measurement, the data from the sensor is used in further localization processing. The measurement quality of sensors can be ascertained since the applied localization fields contain spatial features that lead to a limited group of possible measurements for certain sensor configurations. For example, a voltage field that is designed to be linear, over a certain region within the localization space, can only produce linear voltage variations on a distributed group of sensors. With this example field, a catheter with 3D sensor distribution measuring the voltage would be fully represented by a first order spatial function. Any electrodes that deviate from this first order structure can be eliminated from further analysis. The spatial function can be a set of spherical harmonic functions and this ensures the physics of the problem is also satisfied in this process. To allow for certain practical nonlinear variations in this field setup, a $2^{nd}$ order function can be added to the field description. The energy of the $2^{nd}$ order function can be controlled based on the understanding of the expected nonlinearity of the field. This understanding of field nonlinearity can be measured from historical data or from experiments and simulations. In addition, electrode groups that are physically setup parallel to each other or at a certain known angle to each other, in a linear field, have known ratio metric measurement relationships. This can also be used to test the quality of the electrode measurement. In addition, the calibration process (e.g., scale factor) from a neighboring or current region can be used to check the consistency of fit of the measurement from a set of sensors (e.g., one or more sensors with known positional relationships).

Following step 7325, the method proceeds to step 7326 to determine if the device configuration was confirmed. If not, an alert can be generated in step 7327. But if the configuration was confirmed in step 7326, the method proceeds to step 7330. The method could also proceed to step 7330 from step 7320.

In step 7330, the device configuration is compared to the localization results and a determination is made of whether a mismatch exists, in step 7340. The localization field is calibrated based on the known device configuration, in step 7345. Whether from 7340 or from 7345, the method continues to step 7140 of the method 7100 of FIG. 3.

Figure 6:
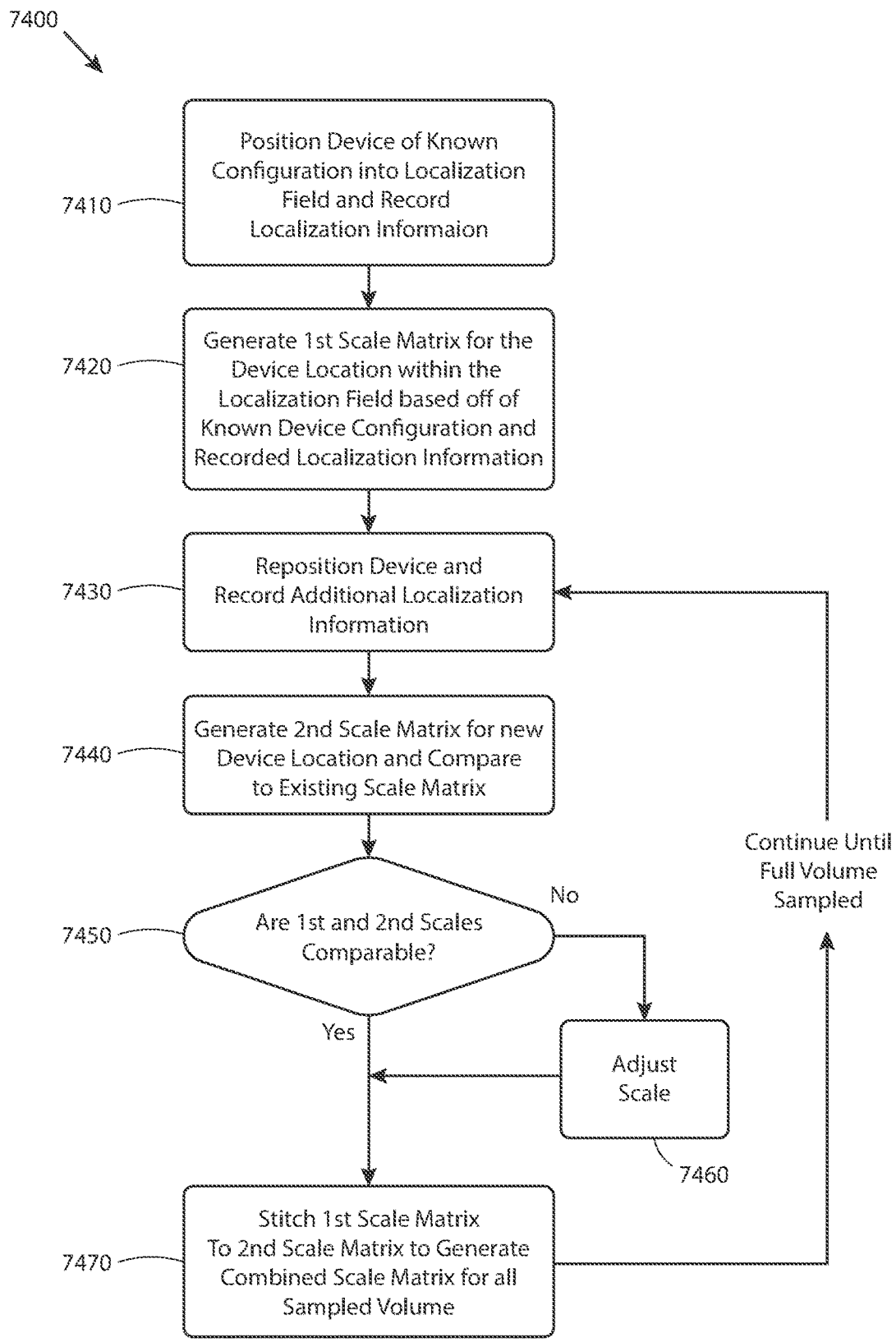
FIG. 6 illustrates a flowchart of an embodiment of a method of generating a combined scaled matrix, consistent with the present inventive concepts.

FIG. 6 illustrates a flowchart of an embodiment of a method 7400 of generating a combined scale matrix 5155, consistent with the present inventive concepts. Various data storage, processing, and generation portions of method 7400 can be carried out by console 5000 of FIG. 1, or components thereof. In various embodiments, the console 5000 can include the scale matrix 5155 to translate raw localization information for a device or functional element of a device to a position relative to an anatomic model 5255. In various embodiments, the scale matrix 5155 can be formed of localization data that can be adjusted or corrected based on at least one reference point or frame of reference.

In step 4710, a device, such as basket array 1150 of catheter 1100 is positioned within a patient P, e.g., within a cardiac chamber of heart H which can be referred to as the region of localization or region of interest. The device has a known configuration, as previously discussed. Using the device, localization information is recorded for the particular device position in the region of interest. For example, electrodes 1151 of basket array 1150 could record voltages used to determine the localization information for each electrode 1151.

In step 7420, a first scale matrix 5155 can be generated for the particular device location within the region of interest based on the known device configuration and the recorded localization information from step 7410. In step 7430, the device is repositioned within the region of interest and additional localization information is recorded. In step 7440, a second scale matrix for the new device location is generated. The second scale matrix is compared to the existing (or first) scale matrix.

In step 7450, a determination is made about whether the second and existing scale matrix were comparable in step 7440. In step 7450, the console 5000 determines if the scales from the two scale matrices are sufficiently similar that the localization data can be combined. If the scales are not sufficiently comparable, the method continues to step 7460 where one or both of the scales are adjusted to make them comparable. In various embodiments, the second scale is adjusted to be comparable to the first scale. Adjusting the scale can include, for example, updating a localization parameter impacting the scale estimation, such as catheter shape, and this update can be performed based on various methods described herein. When the scales are considered to be comparable, the method moves on to step 7470, where the second scale matrix and the existing (e.g., first) scale matrix are stitched together to generate a combined scale matrix. The process can be repeated by returning to step 7430 to generate a combined scale matrix for all or substantially all of the sampled volume, e.g., a cardiac chamber, in step 7470.

The method 7400 of FIG. 6 can be implemented with one or more different types of catheters (e.g., catheter 1110 having a basket array 1150 and/or a lasso shape catheter 1200). Method 7325 can output catheter shape (e.g. basket or lasso shape) and ablation catheter quality and estimates suitable electrodes for field calibration. Next, these catheter measurements can be used to estimate scales from the catheter shape and field estimation model, as described herein. In various embodiments, applied internal sources (e.g., sources at electrodes) on a catheter can detect catheter shape and/or ultrasound transducers can be used to detect catheter shape or position of electrodes with respect to other.

Catheter shape can be further ascertained by checking the consistency of voltage distribution on various subsets of electrodes forming the physical structure of the catheter. For example, a lasso array and/or a basket array can be composed of electrodes organized in sets of parallel lines and/or planes and/or perpendicular lines and/or planes. The lines are composed of two or more electrodes and the lengths of these lines are ratio-metrically related, which leads to ratio metric relationship of their measured voltages. To study this ratio metric behavior, currents can be designed to flow perpendicular to a direction and the voltage dropped by a current on a line depends on the length of the line. This allows checking the quality of a catheter or determining the shape of a catheter based on if the various lines present the right ratio of voltage measurements with respect to each other. The design of currents to flow in a direction involves a computational combination of applied localization currents. Further, a projection of the voltage due to a constant current on a circle consisting of electrodes in plane produces a sinusoidal pattern of measured voltages. So a catheter composed of equal length segments facing different directions placed in a field with approximately constant current (fields from patches described above) measures voltages that can be fit to a sinusoid over a collection of these segments. Based on the quality of fit, the quality of electrode can be ascertained. Also, the quality or shape of basket can be determined by similar method. Further, using a field consisting of linear regions, a first order spherical harmonic can describe the field. A fit to a first order function can be used to estimate the local field and determine electrodes deviating from the fit to check on electrode quality. In regions where some nonlinearity is expected, up to a 2nd order function can be also be used.

Alternatively, when the basket shape is determined, the above described steps can be used to estimate the scale matrix in a region of interest from a collection of electrodes. In a particular embodiment, using a collection of segments, with electrodes, from a catheter (e.g., a lasso, ablation, and/or basket catheter), the scale matrix for currents along a line can be determined first, and then the scale on a plane can be determined. To determine the scale on a plane, the scales for two currents are estimated. These currents are generally non-orthogonal to each other. The scales can be estimated by using a collection of segments and fitting a sinusoidal function to the voltages of each current. Alternatively, to stabilize the scale estimate (e.g., especially when a limited distribution of segments is available and fitting to a sinusoidal function is challenging), the various segments can be organized to utilize the ratio-metric structure of a sinusoidal function and the currents can be combined to create a pair of orthogonal currents for which the individual scales can be determined stably. The orthogonalization process and stable estimate of scale involves selecting suitable segments along certain directions, for example the segment along the direction of a current provides the scale for that current and segments at equal and opposite angle to the direction of a current can be used to create a $2^{nd}$ orthogonal current. This process can then be repeated for one additional plane to get scales along 2 planes. These 2 scales on planes can be then combined to produce a complete 3-dimensional scale.

Measurement of scale change in space can be further accomplished with a linear field region, which by design of a simple localization current, can describe sub-regions within a cardiac chamber. A linear field can be readily characterized with a sub dimensional catheter (e.g., a lasso, ablation, and/or basket catheter) as described above. An example of a simple localization current is the one that is produced in the heart by patches 500 applied to the surface of the patient P. The fields smooth out over space and can be estimated by piecewise linear assumption within the heart. Changes from one field region to the next can be ascertained when a catheter of known dimension changes length along a line or deviates from a fit to a sinusoidal function along an arc trajectory. A region that can be fully described by a first order spherical harmonic function can be considered linear region and deviations from a first order fit can be used to determine the complexity of field estimation needed to describe the localization field in a region.

When the scale change is observed the scales can be expanded. As the catheter moves to new location a continuity in scale is expected. This allows for expanding the scale using even a one-dimensional (1D) catheter, such as an ablation catheter. The field stitching process involves estimating a new scale for a neighboring region and creating a unified field with the previously known region. The parameters governing the continuity of scale information and the expected smoothness of the fields can be estimated through historical data. This can give a set parameters to guide the quality of the field stitching process.

One such parameter is the amount of expected scale change between two neighboring positions. This can be used to ascertain if the new estimated field is a reasonable estimation. If the field is reasonable, it is stitched into the estimated field collection. In addition, the previous neighboring field can be used to assess the shape and quality of the catheter as being suitable for use in localization. This produces a smooth and consistent field. In addition, the field can be geared to be from a certain point in respiration cycle by controlling the parameters that allow for an estimated field to be stitched in. Different fields or a correction to the field can be also produced by this type of gating process.

Some examples of the parameters that can be estimated from historical data can include: distribution in field due to spatial, physiological variation and/or characteristic structure of field in certain regions, e.g., veins. Alternatively, the historical data could be used to estimate templates that describe the structure of the field and measurements from the actual catheter can be used to estimate the parameters of the template that can then represent the field in the region or interest for a given patient.

In some embodiments, the field characterization can be obtained by using all of the possible pairs of electrodes of basket array 1150, resulting in a highly overdetermined system of equations ($48^2 \times 3$). In such a case, the scale matrix formulation can assume the field is linear and the scale matrix formulation method finds an average scale matrix 5155, as follows:

$$\begin{bmatrix} \frac{\partial x}{\partial Vx} & \frac{\partial x}{\partial Vy} & \frac{\partial x}{\partial Vz} \\ \frac{\partial y}{\partial Vx} & \frac{\partial y}{\partial Vy} & \frac{\partial y}{\partial Vz} \\ \frac{\partial z}{\partial Vx} & \frac{\partial z}{\partial Vy} & \frac{\partial z}{\partial Vz} \end{bmatrix}$$

for the centroid position at a given time for the basket array 1150, which might not represent the full picture of the field near the basket region.

To have a better field characterization, the system 10 can compute the above scale matrix 5155 at each electrode 1151 position by solving a 47×3 system of equations. This yields 48 scale matrices 5155, which characterize the field at 48 different positions in 3D space for the centroid position at a given time for the basket array 1150. This might not represent the full picture of the field near the basket region locations (i.e., the electrode 1151 positions) instead of just the centroid, hence, having electrode-specific scale matrices 5155 for a given timeframe.

The above scale matrix 5155 formulation approaches assume the field is a linear field. However, any deviation from the linear assumption can be a source of error for localization (in fact the localization field can be a nonlinear field).

The system 10 can be configured to implement a method to capture the curvature of the field, where the scale matrix 5155 can be equipped with the terms that are able to characterize the curvature of the field. A scale matrix having higher order terms allows the field to deviate from being linear, while being able to characterize it's nonlinearity, and can be given by:

$$\begin{bmatrix} \frac{\partial x}{\partial V_x} & \frac{\partial x}{\partial V_y} & \frac{\partial x}{\partial V_z} & \frac{\partial^2 x}{\partial V_x^2} & \frac{\partial^2 x}{\partial V_y^2} & \frac{\partial^2 x}{\partial V_z^2} \\ \frac{\partial y}{\partial V_x} & \frac{\partial y}{\partial V_y} & \frac{\partial y}{\partial V_z} & \frac{\partial^2 y}{\partial V_x^2} & \frac{\partial^2 y}{\partial V_y^2} & \frac{\partial^2 y}{\partial V_z^2} \\ \frac{\partial z}{\partial V_x} & \frac{\partial z}{\partial V_y} & \frac{\partial z}{\partial V_z} & \frac{\partial^2 z}{\partial V_x^2} & \frac{\partial^2 z}{\partial V_y^2} & \frac{\partial^2 z}{\partial V_z^2} \end{bmatrix}$$

In various embodiments, the system can be configured to depict a better picture of how the field varies, in addition to electrode-specific scale matrix calculation. There are enough measurements for the computation of higher terms, and therefore, the curvature as well as the scale factors can be determined.

In various embodiments, a 2-step predictor-corrector method for electric field (E-field) estimation using sub-dimensional electrode arrays can be implemented. The method can include obtaining an estimate for the electric field vectors in regions un-sampled by the basket electrode array 1150 of catheter 1100, which requires sampling with some set of electrodes with known inter-electrode distances. In general, the regions of interest (e.g., veins or atrial appendages) may be restricted in the sense that sampling with the basket 1150, even in its contracted state, may not be possible. In this case, it may be feasible to obtain potential measurements using sub-dimensional electrode arrays such as lasso catheter 1600 and/or ablation catheters 1500 which span 1 or 2 spatial dimensions. A lasso presents a set of electrodes 1651 positioned around the perimeter of a nominally circular catheter while an ablation catheter 1500 presents, typically, three (useful) electrodes 1551 in a linear array. In both cases, the physical separation between adjacent electrodes is known.

Both catheters may be flexible, but restricting attention to pairs of adjacent electrodes, the separation between electrodes may remain nearly constant even with distortion of the associated catheter shape. To compensate for the reduced dimensionality of the associated electrode array, the catheter must be oriented or moved in space (e.g., by an operator or robotically by the system) in a manner such that all three spatial dimensions are sampled. An additional complication arises due to the absence of any a-priori orientation information through which to relate the electrode positions to physical coordinates. In other words, while the physical separation between electrodes and electrode pairs may be well constrained, the axial projections (i.e. projections of segment length onto the global x, y, z axes) of any segment are unknown.

A 2-step predictor/corrector method is developed to overcome the above mentioned difficulties. The E-field vectors can be assumed to form an orthogonal basis, then any catheter segment with known length l between adjacent electrodes provides a constraint relating length, field strength, and potential difference as:

$$l^2 = \left( \frac{dx^2}{dVx} \Delta Vx^2 + \frac{dy^2}{dVy} \Delta Vy^2 + \frac{dz^2}{dVz} \Delta Vz^2 \right)$$

in which, e.g., $$\frac{dx}{dVx}$$

is the 'x' component of the E-field vector in the direction of $\nabla Vx$. Recalling our assumption that the E-field vectors form an orthogonal basis, the above three components completely describe (within the bounds of the stated assumptions) the local E-field which is then given by the columns of the array:

$$\begin{bmatrix} \frac{dx}{dVx} & 0 & 0 \\ 0 & \frac{dy}{dVy} & 0 \\ 0 & 0 & \frac{dz}{dVz} \end{bmatrix}$$

Note that here the spatial coordinates are aligned with the three field gradients. By expressing the above relation for every valid pair of electrodes (i.e., every pair in which the physical separation is known independent of catheter deformation) over the sampling time interval, we obtain an overdetermined system of equations for the three field vector components in a basis aligned with the local field gradients. For lack of any other registration information, it is assumed that these vectors are parallel to the global 'patch' reference frame formed by the E-field source patches. Additionally, it is implicitly assumed that the sampled field is homogeneous and constant over the time required to obtain the samples. The field components obtained above are then rotated into the localization reference frame, producing the following array of 'predictor' scale factors by which a potential difference may be transformed into a physical vector:

$$\begin{bmatrix} \frac{\overline{dx}}{dVx} & 0 & 0 \\ 0 & \frac{\overline{dy}}{dVy} & \frac{\overline{dy}}{dVz} \\ 0 & \frac{\overline{dz}}{dVy} & \frac{\overline{dz}}{dVz} \end{bmatrix}$$

The corrector step generalizes the set of field vectors/scale factors by assuming that the orientation of each segment produced by the above set of scale factors is correct. The axial projection of a segment between two electrodes is then given by:

$$\Delta X = \Delta x \frac{L}{l}$$

L and l are, respectively, the actual and computed segment lengths, and $\Delta X$ and $\Delta x$ are the 'corrected' and computed projections of the segment onto, in this case, the anterior-posterior (AP) x axis. The computed projections are, again, obtained with the set of predictor scale factors. Now with three axial projections of each catheter segment in the desired (AP) reference frame, we obtain a set of equations relating the nine field vectors components (in AP space) to measured potential differences as:

$$\begin{bmatrix}\Delta X \\ \Delta Y \\ \Delta Z\end{bmatrix} = \begin{bmatrix} \frac{dx}{dVx} & \frac{dx}{dVy} & \frac{dx}{dVz} \\ \frac{dy}{dVx} & \frac{dy}{dVy} & \frac{dy}{dVz} \\ \frac{dz}{dVx} & \frac{dz}{dVy} & \frac{dz}{dVz} \end{bmatrix} \begin{bmatrix}\Delta Vx \\ \Delta Vy \\ \Delta Vz\end{bmatrix}$$

in which, e.g., $\Delta X$ and $\Delta Vx$ are 1-D (one dimensional) arrays of all possible realizations of the axial projections and measured potential differences over the sampling catheter. The three resulting systems of equations are solved for the 9 'corrector' scale factors which may subsequently be used to localize any electrodes which are introduced into the sampled region.

Localization of electrodes using the 'corrector' set of scale factors may proceed by one of two methods depending on the characteristics of the sampling catheter. For catheters with multiple electrodes, the centroid of the electrode array may be localized using the mean measured potential and a 2-point approximation to the integral:

$$\Delta x = \int_1^2 \nabla x \cdot dV$$

in which points 1 and 2 represent, respectively, some known reference position in the core and the desired peripheral point and $\nabla x$ is the array of scale factors (which is necessarily variable between the reference and peripheral points). Once the center of the electrode array is localized, the position of each electrode relative to the localized center is obtained using only the peripheral scale factors. For individual electrodes not spatially connected (e.g., if a single electrode is employed to sample the characterized space over some short time interval), each measurement may be localized relative to some reference point using the 2-point approximation as described above. Alternatively, the center of the 'cloud' of electrode data may be localized using the 2-point approximation, and each individual measurement localized relative to the center using only the peripheral field estimation.

The method can include estimation of peripheral field by conjugate gradient descent down a robustly defined 10-D (ten-dimensional) error surface. Estimating field vectors in regions peripheral or exterior to the core volume sampled by the basket catheter 1100 is complicated by the absence of any information by which orientation of a catheter (e.g. a lasso catheter 1200, 1600) sampling the peripheral region may be related to a known coordinate basis. One way to proceed is to assume that the peripheral field may be represented as a perturbation on the known core field and to define an error function in nine-dimensional (9-D) 'scale factor' space which can be queried by means of the conjugate gradient method. Iteration moves an initial guess along the resulting 10-D error surface in the conjugate gradient direction until the error assumes a sufficiently small value. One possible error function is the square of the magnitude of the difference between the known (physical) length of the electrode-bearing segment of the sampling catheter (e.g. lasso catheter 1600) and the sum of the Euclidian distances between adjacent electrodes, localized with the current estimates of the field vectors. The most convenient initial guess is an average scale matrix 5155 obtained from a subset of the core field 'close' to the region of interest. In what follows, this will be referred to as the 'reference' field.

The proposed error function is defined as:

$$\varepsilon_t = \sum_{i=1}^{n}\{D_i - [\nabla x \Delta V_i \cdot \nabla x \Delta V_i]^{1/2}\}^2$$

in which i indicates the set of all n catheter segments between adjacent electrodes, $D_i$ is the known physical length of each segment, and $\Delta V_i$ is the (triplet of) potential difference between the two electrodes bounding the i'th segment. The goal of this form is to minimize the sum of the differences in length between the known and localized segments.

The gradient of the error function with respect to the 9 scale factors $\lambda_{k,l}$ is then:

$$\varepsilon_t = \sum_{i=1}^{n}\{D_i - [\nabla x \Delta V_i \cdot \nabla x \Delta V_i]^{1/2}\}^2$$

in which i indicates the set of all n catheter segments between adjacent electrodes, $D_i$ is the known physical length of each segment, and $\Delta V_i$ is the (triplet of) potential difference between the two electrodes bounding the i'th segment. The goal of this form is to minimize the sum of the differences in length between the known and localized segments.

The gradient of the error function with respect to the 9-D scale factors $\lambda_{k,l}$ is then:

$$\frac{d\varepsilon_t}{d\lambda_{k,l}} = -2\sum_{i=1}^{n}\{D_i - [\nabla x \Delta V_i \cdot \nabla x \Delta V_i]^{1/2}\}\frac{1}{[\nabla x \Delta V_i \cdot \nabla x \Delta V_i]^{1/2}}\Lambda_{k,l}$$

in which:

$$\Lambda = \begin{bmatrix} \Delta V_x C_1 & \Delta V_y C_1 & \Delta V_z C_1 \\ \Delta V_x C_2 & \Delta V_y C_2 & \Delta V_z C_2 \\ \Delta V_x C_3 & \Delta V_y C_3 & \Delta V_z C_3 \end{bmatrix}$$

And:

-continued $$C_1 = \frac{\partial x}{\partial V_x}\Delta V_x + \frac{\partial x}{\partial V_y}\Delta V_y + \frac{\partial x}{\partial V_z}\Delta V_z$$

$$C_2 = \frac{\partial y}{\partial V_x}\Delta V_x + \frac{\partial y}{\partial V_y}\Delta V_y + \frac{\partial y}{\partial V_z}\Delta V_z$$

$$C_3 = \frac{\partial z}{\partial V_x}\Delta V_x + \frac{\partial z}{\partial V_y}\Delta V_y + \frac{\partial z}{\partial V_z}\Delta V_z$$

The 9 gradient terms are then the local direction in scale-factor space along which error increases most rapidly. Reversing the direction of each term in the gradient array yields the conjugate gradient which is the direction of steepest descent towards smaller error.

From the initial guess (i.e., the 9-D scale factor terms defining the reference field) the 9 gradient terms are computed iteratively and the reference field sequentially modified until the error assumes a sufficiently small value. The final 9-D scale factors are those which, in the coordinate basis of the reference field, admit localization of the sampling catheter with minimum length error relative to the known physical dimensions of the catheter.

An alternative form of the error function is given by:

$$\varepsilon_t = \left\{\sum_{i=1}^{n} D_i - \sum_{i=1}^{n}[\nabla x\Delta V_i \cdot \nabla x\Delta V_i]^{1/2}\right\}^2$$

with terms and subscripts defined as before. With this error function, the goal is to minimize the difference in length between the sums of the known and localized segments. This is a more global approach in contrast with the previous function, which attempts to minimize the sum of the differences in individual segments. While the gradient terms are slightly different, the resulting form is apparent and the solution procedure is identical.

A slightly more involved approach is to apply the two forms of the error function sequentially, switching from one to the other in subsequent iterations. This methodology would, attempt to minimize both the sum of differences in segment lengths and, simultaneously, the difference between the sums of segments lengths, in order to (attempt to) control both the total catheter length and the length of each segment.

In various embodiments, the system 10 can implement a high-performance implementation of position planarity evaluation algorithm. The purpose of the algorithm is to check if the auxiliary catheters (e.g. 1200, 1500, 1600) are well-distributed in space during the calibration process so that the data can be used for the best scale matrix 5155 fitting.

The algorithm is to examine data, e.g., 1000 frames of data, representing 1000 positions inside the atrial chamber. The voltages at selected three electrodes (e.g. 1251, 1551, 1651) on the auxiliary catheters are examined. Each frame of voltage data is transferred to two position vectors, from electrode 1 to electrode 3, and electrode 2 to electrode 3, respectively.

$$M = \begin{bmatrix}\overrightarrow{\Delta V_1}\\ \overrightarrow{\Delta V_2}\end{bmatrix} = \begin{bmatrix}\Delta V_{1x} & \Delta V_{1y} & \Delta V_{1z}\\ \Delta V_{2x} & \Delta V_{2y} & \Delta V_{2z}\end{bmatrix} \text{ where}$$

$$\Delta V_{ix} = V_{ix} - V_{3x}$$
$$\Delta V_{iy} = V_{iy} - V_{3y}$$
$$\Delta V_{iz} = V_{iz} - V_{3z}$$

To evaluate multiple positions, all the related position vectors are analyzed:

$$M_{\overrightarrow{\Delta V}} = \begin{bmatrix}\Delta V_{11x} & \Delta V_{11y} & \Delta V_{11z}\\ \Delta V_{12x} & \Delta V_{12y} & \Delta V_{12z}\\ \Delta V_{21x} & \Delta V_{21y} & \Delta V_{21z}\\ \Delta V_{22x} & \Delta V_{22y} & \Delta V_{22z}\\ & \vdots &\\ \Delta V_{K1x} & \Delta V_{K1y} & \Delta V_{K1z}\\ \Delta V_{K2x} & \Delta V_{K2y} & \Delta V_{K2z}\end{bmatrix}$$

The algorithm includes:
1) select various numbers of positions to analyze,
2) calculate the covariances of the positions,
3) do singular value decomposition (SVD) to check dimensionalities and transform position in planar spaces,
4) further evaluations of planarity.

In general, covariance is calculated in according to the following (e.g., using MatLab®, by The MathWorks, Inc.):

$$M_{COV} = M'_{PM} * M_{PM}$$

The same could be done with Eigen using C++.

However, this is not the most efficient approach. Since there are hundreds or even thousands of combinations of the positions, the process of organizing different combinations of positions into different sizes of matrices, doing matrix transposition and multiplications can be computationally intensive. This would also imply a lot of memory stress.

For the specific algorithm, there are two vectors for each catheter position. One combination of N positions would have position matrix in size of 2N×3. And the covariance matrix would be a 3×3 symmetrical matrix.

To remove the redundancy in covariance calculation, the covariances within each catheter position are calculated first:

$$COV_{11} = \Delta V_{1x} * \Delta V_{1x} + \Delta V_{2x} * \Delta V_{2x}$$
$$COV_{12} = \Delta V_{1x} * \Delta V_{1y} + \Delta V_{2x} * \Delta V_{2y}$$
$$COV_{13} = \Delta V_{1x} * \Delta V_{1z} + \Delta V_{2x} * \Delta V_{2z}$$
$$COV_{22} = \Delta V_{1y} * \Delta V_{1y} + \Delta V_{2y} * \Delta V_{2y}$$
$$COV_{23} = \Delta V_{1y} * \Delta V_{1z} + \Delta V_{2y} * \Delta V_{2z}$$
$$COV_{33} = \Delta V_{1z} * \Delta V_{1z} + \Delta V_{2z} * \Delta V_{2z}$$

The calculation of covariances of different combinations of positions would become summation rather than multiplication, wherein no extra memory is consumed:

$$M_{COV} = \begin{bmatrix}\sum_{i=1}^{K}COV_{11_i} & \sum_{i=1}^{K}COV_{12_i} & \sum_{i=1}^{K}COV_{13_i}\\ \sum_{i=1}^{M}COV_{12_i} & \sum_{i=1}^{M}COV_{22_i} & \sum_{i=1}^{K}COV_{23_i}\\ \sum_{i=1}^{K}COV_{13_i} & \sum_{i=1}^{K}COV_{23_i} & \sum_{i=1}^{K}COV_{33_i}\end{bmatrix}$$

For a symmetric matrix, the singular values are the same as the eigenvalues and so Eigen decomposition can be used instead of the more costly SVD.

Also, for matrix X[M, N], the singular values are the square root of the eigenvalues of the N×N matrix of X*X. The same strategy is also applied here. The following formula can be used to calculate the inverse of 2×2 matrix:

$$\begin{bmatrix} a & b \\ c & d \end{bmatrix}' = \frac{1}{ad-bc}\begin{bmatrix} d & -b \\ -c & a \end{bmatrix}$$

In our case, we have even more special case: b=0, therefore:

$$\begin{bmatrix} a & 0 \\ c & d \end{bmatrix}' = \begin{bmatrix} 1/a & 0 \\ -c/ad & 1/d \end{bmatrix}$$

Figure 7:
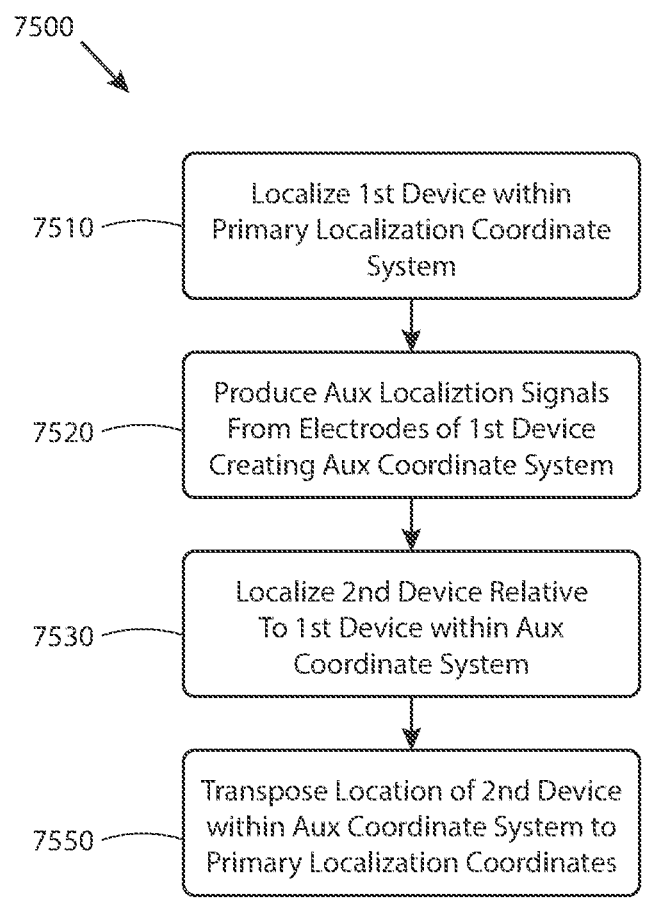
FIG. 7 illustrates a flowchart of an embodiment of a method of transposing a location of a device to a set of localization coordinates, consistent with the present inventive concepts.

FIG. 7 illustrates a flowchart of an embodiment of a method 7500 of transposing a location of a device to a set of localization coordinates, consistent with the present inventive concepts. Various data storage, processing, and generation portions of method 7500 can be carried out by console 5000 of FIG. 1, or components thereof.

In step 7510, a first device, e.g., one of catheters 1000, is localized within a primary localization coordinate system. The catheter can be localized using impedance and/or magnetic localization modes, as discussed herein. In step 7520, auxiliary localization signals are produced from electrodes of the first device, such as aux functional elements 1190, which could be, as examples, electrodes, magnetic coils, ultrasound transducers, or a physiological sensor.

In step 7530 a second device is localized relative to the first device within the aux coordinate system. In step 7550, the location of the second device is transposed from the auxiliary coordinate system to the primary localization coordinate system. Accordingly, the first and second devices are localized within the primary localization coordinate system.

The console 5000, and components thereof, can further be configured to provide localization during a procedure, e.g., a diagnostic or therapeutic procedure. However, insufficient sampling of the target volume (e.g. left cardiac atrium) may result in field estimates which are compactly distributed. Thus, if the basket array 1150 is not moved smoothly and continuously during an anatomy scan (e.g., building of anatomic model 5255), field estimates, which are created at each discrete centroid position, may be clustered such that significant gaps exist in which field estimates are not explicitly available. An electrode (e.g., an electrode 1551 of catheter 1550) moving across this gap may experience localization discontinuities as the field estimates transition between clusters.

In various embodiments, the console 5000 is configured to construct a convex hull around the entire centroid cloud. Within the convex hull, the console constructs a conformal orthonormal grid. Here, conformal means the grid fills the volume of the convex hull without extending exterior to its boundaries. On this grid, at specified intervals on each coordinate axis, the console interpolates IQ potential and field scale factors by assigning each grid point to an element of the Delaunay triangulation of the centroid cloud. The console 5000 interpolates from the corner points onto the grid point using, e.g. barycentric interpolation. Localization is then executed by averaging distances from a set of closest grid points using known grid position and interpolated IQ potential and scale factors. Averaging is advantageous due to uncertainty inherent in interpolation from four centroids comprising the corners of the bounding Delaunay volume element.

Another issue is that changes in blood conductivity due to continuous infusion of conductive fluid (e.g. saline) during electrophysiology (EP) procedures can adversely influence impedance-based localization. However, in accordance with the inventive concepts, a catheter with known inter-electrode spacing and configuration (e.g. catheter 1100 with electrodes 1151) can be configured to measure impedance from which conductivity at the desired frequency may be computed. This can be done at intervals during the procedure to correct scale factors computed during anatomy construction. The corrected scale factors permit improved localization of auxiliary EP electrode arrays (e.g. treatment catheter array 1550), for example.

The console 5000, and components thereof, can further be configured to build or update the anatomy during a procedure, e.g., a diagnostic or therapeutic procedure. The algorithmic steps that generate anatomy (anatomic model 5255) using catheter 1100 having array 1150 are sufficiently different from the algorithmic steps that generate auxiliary localization (e.g. localization of one or more catheters 1000 used with system 10, such that a mismatch can occur between navigation of conventional catheters and the surface of the anatomy (anatomic model 5255). This potential mismatch is especially undesirable in the case where catheter 1500 is an ablation catheter.

In accordance with aspects of the inventive concepts, console 5000 can be configured to address the potential mismatch issue. During the process of scanning anatomy (creating anatomic model 5255), the so-called "raw" localization data for all functioning electrodes 1151 of basket array 1150 (e.g., the 48 electrodes 1151 in FIG. 2) is available, continuously, throughout the recording process. While scanning, the spline-electrodes 1151 are maneuvered broadly around the entire chamber and are also likely to reach the endocardial surface on a broad-scale. If one imagines plotting the trajectory of all electrodes 1151 through the entire time of scanning the anatomy, it is easy to picture a surface that can be algorithmically defined as the outer-boundary of the spline-electrodes 1151 for which said trajectory is limited by the endocardial surface. It is possible for a mismatch to occur between said trajectory-surface and the generated anatomy-surface and which can correlate, at least in part, with the mismatch between auxiliary catheter navigation and the generated anatomy-surface. Thus, since the anatomic model 5255 is an average of the chamber size over the heart cycle, there may be recorded locations that "localize" as "outside" of the cardiac chamber, such as if an electrode is located on the endocardial surface during diastole. However, the raw, spline-electrode 1151 localization domain ought to correlate, at least in part, with the auxiliary localization domain, e.g., the volume that encloses all points of any electrode 1151 during anatomy creation, should also enclose any localized electrode thereafter.

This characteristic can be applied to volumetrically scale the localization domain to be optimally fitted to the anatomy domain. There is a range of algorithmic sophistication that could be applied to achieve an effective improvement of auxiliary navigation upon the anatomy 5255. Such algorithms include, but are not limited to:

1) A radial projection of x,y,z values from each localized point to the anatomy-surface, relative to the anatomy-centroid.

2) A best-fit, volumetric, affine transform of the localization-domain to the anatomy-domain based on 3 elements,
3) A best-fit, volumetric, affine transform of the localization-domain to the anatomy-domain based on 9 elements.
4) Intermediary processing steps can also be applied before transforming from the localization domain to the anatomy domain. For example, the "anti-jitter" filter could be applied on the localization data obtained during scanning to more closely match the dimensional dynamics of the spline-electrodes 1151 to the auxiliary electrodes (e.g. 1551).
5) The online scanning tool can be updated to provide feedback to the operator to be certain that the spline-electrodes 1151 sufficiently sample the endocardial surface for the purpose of scale-matching.

The console 5000 can be configured to build an anatomical model 5255, e.g., using ultrasound transducers of the basket array 1150. However, the anatomy (anatomic model 5255) created by radial averaging from a fixed origin suffers from shadowing and inappropriate averaging of structures which are nearly parallel to the radial vector. However, using the anatomy 5255 created by radial averaging as a starting point, identify and average all ultrasound hits lying within the right prism associated with each surface element. The resulting point is placed at the averaged distance from the element center along the element normal. New vertex coordinates are generated by averaging over adjacent elements to retain the original element/vertex map.

Also during a procedure, localization accuracy can be improved by better estimating the size and shape of the diagnostic catheter 1100 (e.g., the shape of basket 1150) during a procedure. One method to do this is to generate localization signals between catheter electrodes 1151 to create a field that can be used to estimate the distance between electrodes 1151, the local field constant, and the distance from the cardiac wall. Another is to create an external magnetic field which can be sensed by a coil 1152 in physical contact with the catheter 1100.

The local field can be set-up by generating a differential electric field at localization frequencies between two separate catheter electrodes 1151 or by generating a single ended magnetic field between a remote electrode (such as a skin patch 500) and a local receiver such as a coil 1152 positioned on the catheter itself.

With further regard to localization of auxiliary electrodes (e.g. 1551, 1651), such localization can be accomplished by extrapolation from a region in which the localization source fields are well characterized (i.e. the 'core' region populated by basket 1150 centroids) into peripheral regions which are un-sampled by the basket array 1150. Any field curvature outside the 'core' region can therefore introduce localization errors relative to the physical position of the auxiliary electrode.

Considered as a static scalar field, each localization source field is harmonic and charge-free such that variation of the field satisfies Laplace's equation. Extrapolation of the field exterior to the 'core' region may therefore be accomplished using a spherical harmonic approximation, and auxiliary catheters (e.g. 1500, 1600) may then be localized using the extrapolated fields. Field estimation and localization of peripheral electrodes proceeds as follows:

Localize the basket centroid at each frame, preferably using the auxiliary localization integration technique utilizing the measured properties of the three source fields at each basket 1150 position. Each centroid position is associated with a mean potential in each of the source fields.

Construct a surface interior to the anatomy 5255 which is largely coincident with the centroid cloud. In practice, a spherical shell meshed by a non-structured triangular grid will suffice, although a higher order surfaces such as a symmetric or generalized ellipse may also be employed. Onto each node of the mesh, interpolate the three source potentials using the inverse of the 'core' based auxiliary localization procedure:

$$V = \frac{1}{n}\sum_{i=1}^{n} V_{c_i} + \nabla x_i^{-1} (\vec{x} - \vec{x}_c) c$$

in which n is some number of centroids (multiple centroids are employed to average any errors and periodicities present in the source field measurements), and c indicates a centroid value (i.e. position or source potential). $\nabla x$ is interpreted as 'the gradient of position with respect to source potential'.

Once the spherical shell is populated with the source field values, a set of spherical harmonic coefficients $a_{l,m}$ is computed which are consistent with:

$$V = m \sum_{l=0}^{n} \sum_{m=-l}^{l} a_{l,m} r^l Y_l^m(\vartheta, \varphi)$$

in which n is the user-specified order, r $\vartheta$ and $\varphi$ are the spherical-polar coordinates of a point on the mesh, and $Y_l^m$ are the spherical harmonic basis functions or order l and degree m. The above equation is solved in the sense of LLS for the coefficients $a_{l,m}$ using the coordinates and potential at each point on the mesh. Since each source field is independently harmonic, the potential of the associated source field at a point in space is obtained with the computed coefficients and the basis functions associated with the coordinates of the point in question.

Solution of the LLS problem for the three sets of coefficients requires specification of the order (l above) of basis functions to be considered. The total number of basis functions is the square of one plus the order. So that, e.g., 3 orders provides 16 total basis functions to describe the angular variation of, in this example, each of the three potential distributions. A loose rule is that the angular resolution is given approximately by pi/l, so that along any hemispherical meridian, three distinct regions may be recognized. Specification of higher orders (i.e. greater than 3) will frequently result in a poorly posed inverse problem in which the condition number of the 'S' component of the singular value decomposition increases and eigenvalues associated with noise or non-physical variations dominate. In practice, it may be possible to permute the requested order to obtain a decomposition with a viable condition number.

The spherical harmonic transformation is a nonlinear transformation from position (in terms of the coordinates r $\vartheta$ and $\varphi$) to potential. As such, localization, which is a determination of position based on three measured values for the source fields, requires the inverse transformation which is not analytically representable. Instead, we obtain an estimate of position using a "current aux loc" procedure, then update the position iteratively until the potential associated with the updated position (via the spherical harmonic transformation) matches the measured potential. A simple Newtonian iteration is sufficient, with the gradient at each sample point approximated by a set of difference terms constructed from potentials computed with the spherical harmonic basis functions.

Alternately, once the spherical harmonic coefficients are computed, the source fields may be extended and tabulated on a grid both interior and exterior to the core region, and position is obtained from potential by means of a look-up table. Arbitrary accuracy may be obtained by construction of and sampling on a sufficiently fine grid, along with tri-linear interpolation of the gridded data, if necessary.

Note that localization by spherical harmonic extrapolation will not exactly reproduce the positions and potentials of centroids since the coefficients are computed from averaged centroid potentials (via the 'localized' potentials populating the spherical mesh). The spherical harmonic field is thus a representation of the 'averaged' potential within the target volume.

Additionally, issues may arise with auxiliary localization by integration of superimposed discrete harmonic fields. That is, localization of electrodes in peripheral regions of the cardiac atria using field estimates obtained from centrally positioned electrode arrays (e.g. basket 1150) may be confounded by field curvature. For example, localization fields in the center of the left atrium may not accurately describe the potential gradient near PV ostia or other structures. Unless field estimates are available across the entire volume in which localization may be required, electrodes distant from the sampled volume may be localized inaccurately. It is therefore desirable to obtain field estimates over the entire volume, and given the absence of charge within the region of interest, the assumption of harmonic source fields may be advantageously employed.

However, the system 10 may address this by executing various localization methods. A globally harmonic field satisfying the potential measured by the mapping catheter 1100 may be constructed by assuming the existence of a set of points, typically distributed approximately uniformly, on a spherical surface circumscribing the anatomy 5255. At each point, a charge is positioned, and the voltage at any point in space induced by that charge is the Coulomb potential given by:

$$\varphi = \frac{K}{r}$$

in which K is a constant proportional to the charge and r is the Euclidian distance between the charge and the point of interest.

Superposition of fields produced by the combination of charges distributed over the surface is then:

$$\varphi = \sum_n \frac{K_n}{r_n}$$

The potential induced on the collection of centroid positions (i.e. the positions of the basket array 1150 at which localization potentials are known) may be written in matrix form as a function of now unknown charge as:

$$\begin{bmatrix} \varphi_1 \\ \vdots \\ \varphi_n \end{bmatrix} = \begin{bmatrix} \frac{1}{r_{11}} & \cdots & \frac{1}{r_{m1}} \\ \vdots & \ddots & \vdots \\ \frac{1}{r_{1n}} & \cdots & \frac{1}{r_{mn}} \end{bmatrix} \begin{bmatrix} K_1 \\ \vdots \\ K_m \end{bmatrix}$$

in which n is the number of points at which potential is known, and m is the number of charges distributed on the circumscribing surface. If n>m, then the system is ostensibly overdetermined, but proceeding naively will likely result in predominance of noise resulting from amplification of the smallest eigenvalues.

It is therefore necessary, in most cases, to employ regularization such that:

$$K = [A^t A + \lambda^2 I]^{-1} A^t \varphi$$

in which A is the n×m matrix above, and $\lambda$ is a regularization parameter which is chosen to damp the higher order contributions, leaving a distribution dominated by low order contributions approximating a dipole field. With the charge distribution determined, localization potential may be computed at any point in space.

In some embodiments, the system 10 can be configured to implement a method to achieve accurate computation of scale matrix for localization. The localization of the basket 1150 and other EP catheters (e.g. 1200, 1500, 1600) all depends on the scale matrix 5155, which maps voltages to positions. The current method for computation of this matrix 5155 is under the assumption of having a perfectly linear voltage field and hence, any deviation from linearity introduces errors into localization, which can happen near the pulmonary veins as an example. With the goal of reaching 1 mm localization accuracy, it is essential to consider the feasibility of other methods of calculating scale matrix 5155. The linearity of the voltage can be a good assumption in some regions of the localization field but not in the entire atrium where the catheters are maneuvered near the pulmonary veins.

The basket 1150 potentials provide a great sampling information from the region in which they are located. This can be used to characterize the voltage field in the region of the basket array 1150. In various embodiments, system 5000 can use a known high-order and nonlinear analytic function to fit to the electrodes' potentials (e.g. electrodes 1151). In fact, this function characterizes the voltage variation within the region enclosed by the basket 1150. As an example, a complete cubic polynomial can be chosen to fit to the basket 1150 voltages, as follows:

$$f_i(x, y, z) = \\ c_1 x^3 + c_2 y^3 + c_3 z^3 + c_4 x^2 y + c_5 x^2 z + c_6 y^2 x + c_7 y^2 z + c_8 z^2 y + c_9 z^2 x + \\ c_{10} x^2 + c_{11} y^2 + c_{12} z^2 + c_{13} xy + c_{14} xz + c_{15} yz + c_{16} x + c_{17} y + c_{18} z + c_{19}$$

where i=1, 2, 3 for the field generated by x-, y-, and z-patches (e.g. impedance patches 510). The $c_i$ coefficients will be obtained by solving an overdetermined system of equations for each patch 510 by utilizing the standard basket definition (coordinates) as well as the measured voltages of the electrodes 1151. A special case of the above function is a spherical harmonic function. Assuming the field is harmonic, it can constrain the above method to a group of solutions that ensures that the estimated field satisfies the physics of the problem, i.e., Laplace's equation for fields in a constant impedance region (e.g., a blood pool).

Compared to other methods of computing the scale matrix 5155, the above method characterizes the field with a better agreement with respect to the ground truth (e.g. the actual electrophysiological activity of the cardiac tissue).

In various embodiments once the voltage distribution over space is produced, measured potentials can be localized by integration from a known position (e.g. from a centroid position for which potential is known) so that:

$$\vec{x_p} = \vec{x_c} + \int_c^p \nabla x \cdot dV$$

in which $$\nabla x = \begin{bmatrix} \frac{dx}{dV_x} & \frac{dx}{dV_y} & \frac{dx}{dV_z} \\ \frac{dy}{dV_x} & \frac{dy}{dV_y} & \frac{dy}{dV_z} \\ \frac{dz}{dV_x} & \frac{dz}{dV_y} & \frac{dz}{dV_z} \end{bmatrix}$$

and p and C denote, respectively, the potential for which localization is required and a reference point with known position and potential. Integration is done by, e.g., a $2^{nd}$ order Runge-Kutta method or any other discrete approximation yielding the desired accuracy. This is representative of the current aux loc procedure.

It may be advantageous to average the integrated position over a set of reference centroids so that any noise in centroid position or potential is not carried over into aux electrode positions.

Once a field description is established, a sensor can be localized based on the spatial encoding of the field. A map from voltage to spatial coordinates can be used for this purpose. Interpolation functions can be created that can perform this mapping. The scale matrix generation is a method that can produce a piecewise linear conversion between voltage and space as described above. The scale matrix-based method is advantageous due to simplicity of the computation (numerical stability, computation resource needs) and it works in a piecewise linear or near linear field, while a voltage to spatial coordinate mapping can work with a more general field.

In various embodiments once the voltage distribution over space is produced, the voltage is a nonlinear transformation from position (in terms of the coordinates r ϑ and φ in spherical coordinates or x,y,z in cartesian coordinates) to potential. As such, localization, which is a determination of position based on three measured values for the source fields, requires the inverse transformation of voltage to position which is not analytically representable. In various embodiments, an estimate of position is obtained using the current aux loc procedure, then the position iteratively updated until the potential associated with the updated position (via the spherical harmonic transformation) matches the measured potential. A straightforward Newtonian iteration is sufficient, with the gradient at each sample point approximated by a set of difference terms constructed from potentials computed with the spherical harmonic basis functions.

Alternately, once a method to estimate the voltage field is established, the source fields may be extended and tabulated on a grid, both interior and exterior to the core region, and position is obtained from potential by means of a look-up table. Arbitrary accuracy may be obtained by construction of and sampling on a sufficiently fine grid, along with tri-linear interpolation of the gridded data, if necessary.

Localization of electrode potentials is a unique function of the continuous, but (possibly) curved electric field vectors in the target chamber. Use of a single set of scale factors (i.e., field vectors) to localize a potential far from the associated region of validity will result in an offset from the 'true' (but unknown) position. Use of a set of scale factors obtained from a region near the target potential can result in non-physical offsets between localized electrodes if different scale factors are used for different electrodes.

In various embodiments, the system 10 can execute a method configured to address this issue. According the method, each centroid in a group of localized basket array 1150 positions, if the position is known relative to some arbitrary origin, defines a single realization of the continuous 'averaged' localization field in the target chamber. If that field could be described analytically or numerically, then any electrode could be trivially localized by simply computing the coordinates within the field consistent with the measured potential.

To find a continuous field consistent with the known positions and potentials of a set of localized basket array 1150, specify the functional form of the target manifold. Here, we assume a generalized quadratic form:

$$\alpha_{ij} V_i V_j + \beta_i V_i + \gamma_i$$

in which the indices refer to the three localization source fields. Those skilled in the art will realize that any suitable functional form could be similarly employed.

The position of each localized centroid is then approximated as:

$$X = \alpha_1 V_x V_x + \alpha_2 V_y V_y + \alpha_3 V_z V_z +$$
$$\alpha_4 V_x V_y + \alpha_5 V_x V_z + \alpha_6 V_y V_z + \alpha_7 V_x + \alpha_8 V_y + \alpha_9 V_z + \alpha_{10}$$
$$Y = \beta_1 V_x V_x + \beta_2 V_y V_y + \beta_3 V_z V_z + \beta_4 V_x V_y +$$
$$\beta_5 V_x V_z + \beta_6 V_y V_z + \beta_7 V_x + \beta_8 V_y + \beta_9 V_z + \beta_{10}$$
$$Z = \gamma_1 V_x V_x + \gamma_2 V_y V_y + \gamma_3 V_z V_z + \gamma_4 V_x V_y +$$
$$\gamma_5 V_x V_z + \gamma_6 V_y V_z + \gamma_7 V_x + \gamma_8 V_y + \gamma_9 V_z + \gamma_{10}$$

Expression of the above for each localized centroid results in a set of equations which can be solved in the linear least squares (LLS) sense, assuming more than 10 localized centroids, for the coefficients $\alpha$, $\beta$ and $\gamma$.

Once the coefficients associated with each of the three coordinate dimensions are available, localization is a simple matter of substituting the potential obtained from an electrode into the above quadratic equation and computing the appropriate sum.

In other embodiments of field-based localization, neglecting the quadratic components leaves three linear terms (and a constant) on each IQ axis. The combined nine linear terms are equivalent to a scale matrix averaged over the region sampled by the basket array 1151. Using these terms may provide benefit over the 'single central scale factor' technique by averaging out any anomalous behavior sampled by the 1st frame.

On producing a reliable localization of a group of electrodes, the position of a $2^{nd}$ group of electrodes can be established by fitting the structural model of the combined $1^{st}$ and $2^{nd}$ group of electrodes to the localized position of the $1^{st}$ group of electrodes. Least squares fit, SVD based best fit are some examples of methods that can be used here. This allows for localizing the position of a sensor from which localization field measurements are not available.

In accordance with aspects of the inventive concepts, the system 10 can be configured to implement a method to predict the voltages of $1^{st}$ and $2^{nd}$ electrodes of the ablation catheter during RF delivery. The impedance of electrodes 1551a (tip) and 1551b (the second electrode) of the ablation catheter 1500 can be affected significantly by therapy delivery as well as by electrophysiology (EP) equipment connected to the catheter (electronics modulation). This leads to disrupting the voltage and consequently shifting the position of electrodes 1551a and 1551b.

The voltage measurements at electrodes 1551c and 1551d (the third and fourth electrodes) are significantly less affected, e.g., when RF energy is being delivered through the tip electrode 1551a. These two electrodes 1551c,d can be used to predict true voltages of both $2^{nd}$ electrode 1551b and tip electrodes 1551a and therefore their positions to improve their localization. The ablation catheter 1500 lives in a source-free environment and therefore the voltage distribution of its electrodes must have harmonic properties, a linear field satisfies the harmonic condition, so the voltages of the ablation catheter can be represented as follows:

$$V_{2estimate} = V_3(1+\alpha_1) - \alpha_1 V_4 \text{ where } \alpha_1 = \frac{L_{2-3}}{L_{3-4}}$$

$$V_{1estimate} = V_{2estimate}(1+\alpha_2) - \alpha_2 V_3 \text{ where } \alpha_2 = \frac{L_{1-2}}{L_{2-3}}$$

For a standard ablation catheter, e.g., a 2-5-2 catheter, $L_{3-4}=2$, $L_{2-3}=5$, and $L_{1-2}=2$.

These estimations can then be used to localize the catheter instead of the measured voltages.

Thus, the method provides for predicting the voltages of $1^{st}$ and $2^{nd}$ electrodes (1551a,b) of the ablation catheter 1500 during RF delivery. The equations built into the original estimate for ablation catheter position were:

$V2 = V3 +$ (scale factor derived from $V3$ & $V4$) * (distance between $V3$ and $V2$), which can be written:

$V2 = V3 + ((V3 - V4)/D34) * D23 = V3(1+D23/D34) - V4(D23/D34)$

The same concept was applied to get the distal tip position using the distance from electrode 3 1551c to the distal tip 1551a:

$V1 = V3 + ((V3 - V4)/D34) * (D23 + D12)$

Starting at the equation for the V1 estimate and substituting in the equation for the V2 estimate, it reduces exactly to the estimate above for V1 based on V3 and V4.

In various embodiments, the system 10 can implement a method to accomplish Iterated Close Point (ICP) with scaling for registration of geometrically similar point sets with differing axial extent. Anatomies produced via differing methodologies, for example by tracing the localized path of a catheter (e.g. 1100, 1200, 1500, 1600) in contact with the surface of interest, or by ultrasound projected from a set of localized positions as is done with the system (e.g. basket 1150) may have differing numbers of mesh nodes, different origins, different orientations, and different sizes, possibly including different scales along each coordinate axis (in patent as "anatomic model(s) 5255). The standard technique of ICP may be confounded by size differences, resulting, instead of concentric registration, in close coincidence of part of the anatomy at the expense of poor correlation in all other regions.

The system 10 can address such issues by combining multiple executions of ICP with scaling operations, registration between different anatomic meshes (models 5255) may be iteratively improved to a 'best possible' state in which the RMS offset between corresponding points/features is effectively minimized. For the purpose of this description, the ultrasound anatomy is termed the 'fixed' anatomy ($5255_F$), while the contact anatomy is termed the 'mobile' anatomy ($5255_M$). The procedure is implemented as follows:

1) Execute the standard ICP procedure. Rotate and translate the mobile anatomy using ICP output.
2) Determine axial ratios between the registered anatomies (e.g. ratio of the fixed anatomy to the mobile anatomy along each of the three coordinate axes) and scale the mobile anatomy.
3) Execute steps 1 and 2 a total of three times The output of the iterated ICP procedure is three sets of rotation, translation, and scaling matrices (Different scaling matrix than 5155 used in localization) which may be applied to any point on the mobile (contact) anatomy for the purpose of transformation into the space of the ultrasound anatomy.

Best results are obtained when extended structures, such as veins and appendages, are trimmed to match between the mobile and contact anatomies, and outliers are removed to mitigate bias.

Using the translation, rotation, and scaling matrices obtained from each of the three ICP registration steps, transform position from the space of the mobile contact anatomy to the space of the fixed ultrasound anatomy:

$$P_{us} = (R_3[(R_2[(R_1P_c + T_1)S_1] + T_2)S_2] + T_3)S_3$$

in which R is a rotation, T is a translation, and S represents scaling (independently on each of the AP axes). $P_c$ is a physical location obtained via the 'contact' strategy ("mobile" strategy, same thing) and $P_{us}$ is the position transformed to the space of the ultrasound anatomy.

The scaling steps are implemented as:

$$\hat{P}_i = P_i S_i$$

in which Einstein summation is not implied.

Figure 8:
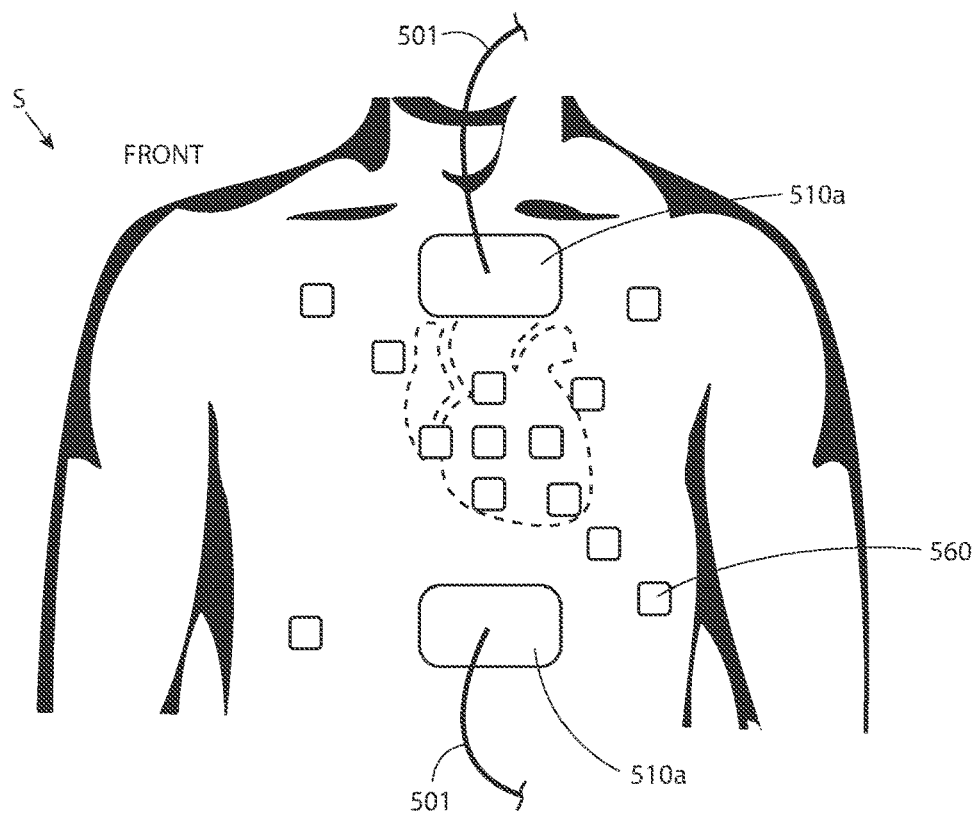
FIG. 8 illustrates a schematic view of an embodiment of portions of the system of FIG. 1 applied to a body, consistent with the present inventive concepts.
Figure 8:
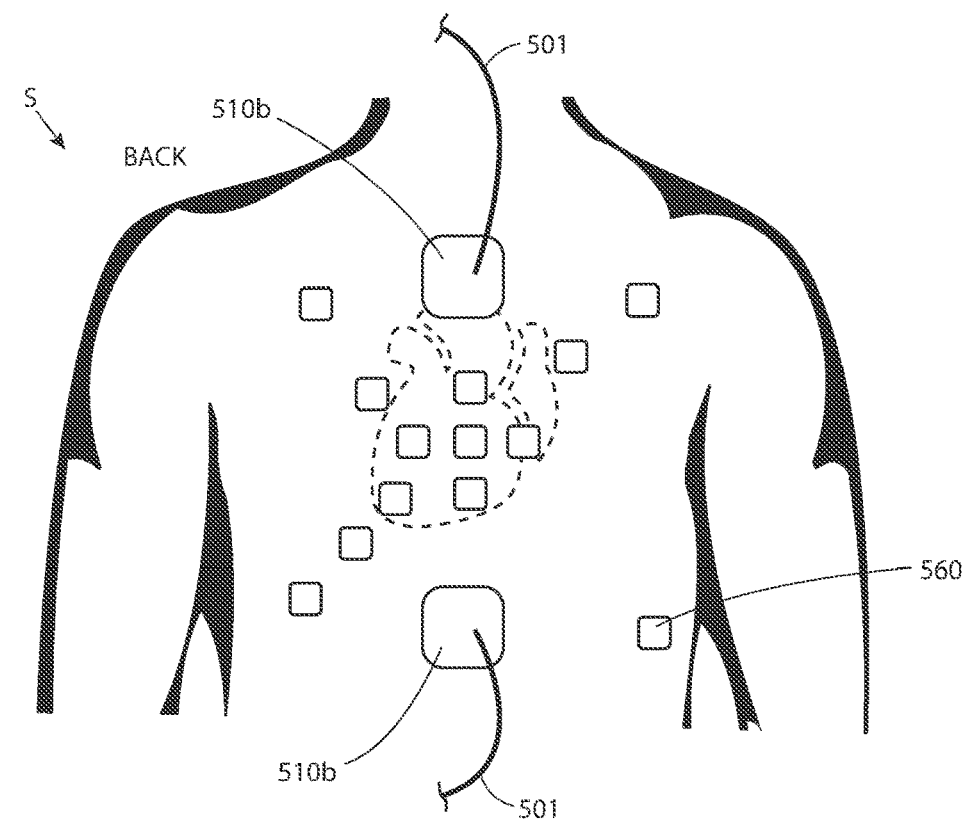

FIG. 8 illustrates a schematic view of an in-vivo/in-vitro hybrid test method setup, consistent with the present inventive concepts. One or more impedance patches 510 are placed on a subject S, such as patches 510a shown on the front of subject S, and 510*b* shown on the back of subject S. The test setup includes an array of EKG/ECG type leads 560, positioned about the torso of subject S, for example as shown.

Using the test setup of FIG. 8, a voltage (or impedance) field can be evaluated on a living subject. For example, an impedance field driven between patches 510 can be affected by several factors, including patch size, patch impedance, and anatomic structures within subject S. By varying the parameters, e.g., patch 510 size, dispersive electrode disturbances can be recreated on various anatomies, e.g., various subjects S, with the localization signal (voltage field) evaluated for patch characterization and simulation correlation. As shown, for example, the surface area of patches 510*b* can be reduced (for example by folding or pealing back a portion of patch 510*b* such that only a portion of the patch is in contact with the skin of subject S), and the effects of this surface area reduction can be measured by the surrounding EKG/ECG leads 560.

In some embodiments, EKG/ECG leads 560 can be equally spaced along an axis of the voltage field at known distances for simulation correlation. This setup can enable detailed evaluation of voltage field changes related to patch 510 parameter changes (size, shape, etc.).

Figure 9:
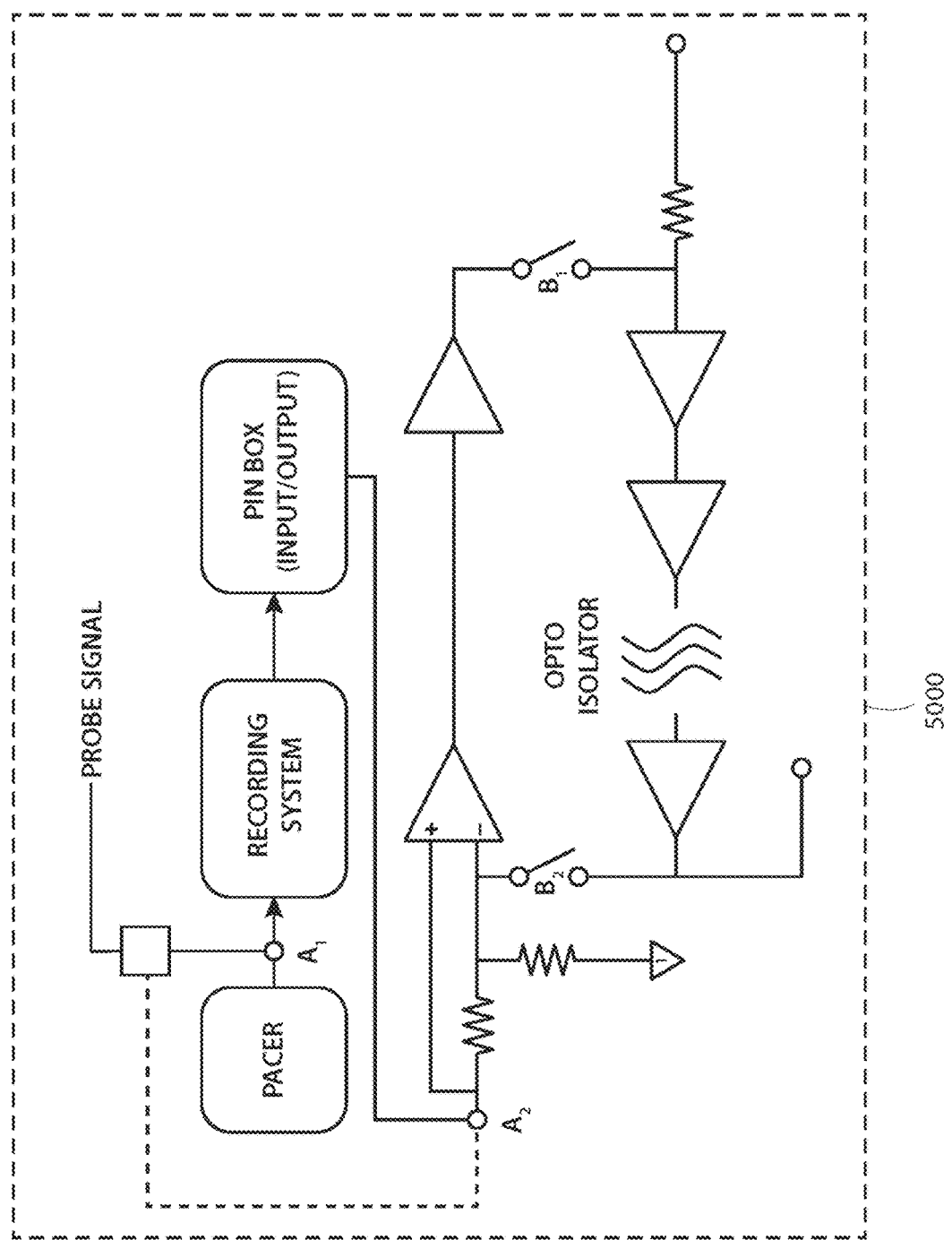
FIG. 9 illustrates an embodiment of a circuit schematic of a high input impedance mapping system, consistent with the present inventive concepts.

FIG. 9 illustrates a circuit schematic of a high input impedance mapping system. Impedance localization stability is correlated with the input impedance of the mapping system. A high input impedance is optimal. The native input impedance of a mapping system can be degraded by interconnecting peripheral equipment such as stimulators, recording systems, and/or other 3D mapping systems. The illustrated schematic is configured to strategically protect the input impedance while allowing the delivery of a stimulus to an electrode.

The circuit exists within the auxiliary interface box, e.g., an interface between a patient P and console 5000 of FIG. 1 (PIN BOX shown in FIG. 9). The pacing stimulus can be detected by a probe represented in FIG. 9 between nodes A1 and A2. The probe applies an electrical pulse applied to node A1 when a pacing channel is enabled the signal shows up on A2 which in turn enables the correct switch configuration to allow the pulse to be delivered. Alternatively, the application of the probe signal can be eliminated, and the pacing pulse can be detected to control the switches. The first pacing pulse detected at A2 enables the correct switch configuration which allows subsequent pacing pulses to be delivered.

Upon detection of a pacing pulse, the switch configuration, B1 closed and B2 open, allows the signal to bypass the buffer circuit which protects the input impedance. When no pacing pulse is detected (normal operation), switch B1 opens and B2 closes thus buffering localization signals from leaking through external pathways and creating voltage variations.

Alternatively, signals can be directed through different pathways based on the signal's amplitude and frequency. Coupling circuits can be designed to take advantage of the various signal features to allow different paths to be selected by a signal and thus providing capability for optimal system functioning. For example, the pacing signal can be bypassed around the isolation circuit, e.g., buffer circuit, using various P-N junction semiconductor devices utilizing various semiconductor device characteristics, such as diodes. This reduces the burden on using detection and (or) switching methods needed for routing various signals appropriately. In some embodiments, a signal can comprise differential and common mode components (e.g. a signal carried on two or more channels of an electrical system can comprise common and differential components). This common mode and differential nature of the signal can be used to prevent (e.g. filter) one or more signals (e.g. one or more components of one or more signals) from leaking through unintended circuit pathways, for example, pathways connected to peripheral equipment such as stimulators, recording systems, and/or 3D mapping systems. The localization signals, as described herein, have a predominantly common mode component when recorded via one or more electrodes within the heart. Filtering the common mode signal from these unintended circuit pathways substantially reduces leakage of localization signals. In some embodiments, a common mode filter (also referred to as a common mode choke herein) can be used to prevent the common mode signal from leaking into inter-connected electronic systems (e.g. one or more unintended circuit pathways). By implementing a common mode choke between a channel carrying a localization signal and an inter-connected electronic system, the common mode choke would appear as a high impedance pathway to the inter-connected system, blocking the common mode localization signal from these inter-connected systems. Additionally, a differential signal, such as a pacing pulse (e.g. a pacing pulse recorded by an electrode connected to an inter-connected system via the common mode choke), would pass though the common mode choke unimpeded, allowing for intended pacing functionality.

Figure 10:
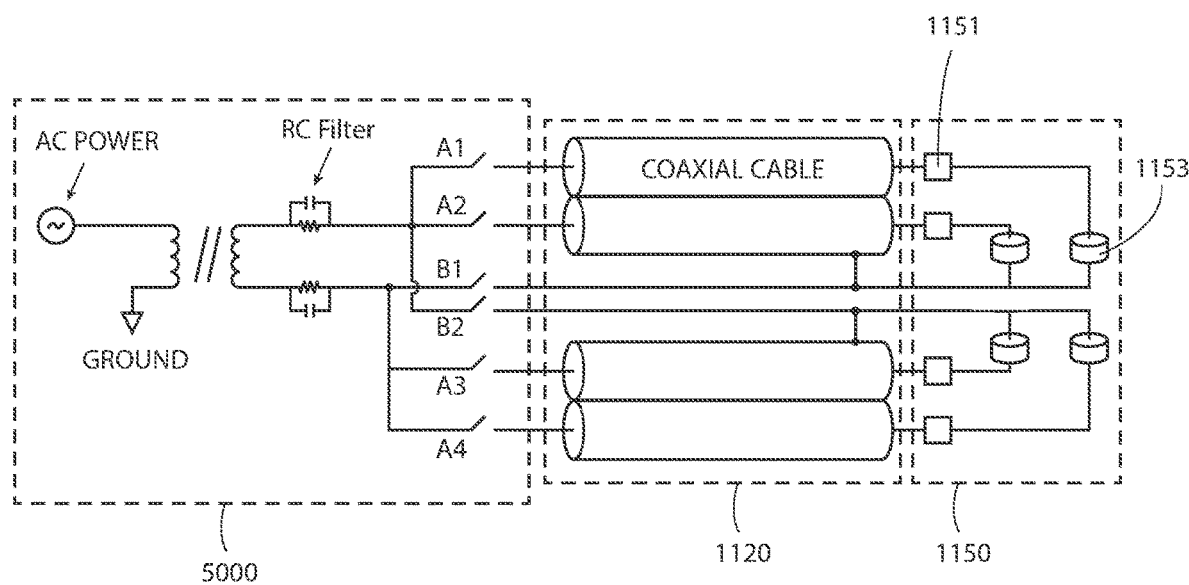
FIG. 10 illustrates an embodiment of a schematic of a portion of a console and mapping catheter, consistent with the present inventive concepts.

FIG. 10 illustrates a schematic of a portion of a console and mapping catheter, including electrodes and ultrasound transducers. Localization accuracy can be improved by better estimating the size and shape of the array 1150 during a procedure. One method to do this is to generate localization signals between electrodes on or in the body, e.g., electrodes 1151 of array 1150. In some embodiments, the localization signals can be delivered through one or more electrodes (in or on the body, the subsequent examples will assume they are in the body and on the same catheter) and can be used to create a field in the vicinity of the catheter. One or more electrodes 1151 of catheter 1100 can be used to measure the generated impedance field at one or more locations in space, simultaneously or sequentially, and can be used to calculate properties of the impedance field, such as geometric properties, e.g., scaling, skew, and/or nonlinearity. In some embodiments, the calculated properties may be temporally-varying (such as gradual drift over time that may occur from physiological processes or acute shifts that may occur from the interconnection of additional equipment).

In some embodiments, measurements of the generated impedance field are made from a set of electrodes that include electrodes that were not used to deliver the generated localization signals. Such 'passive' electrodes can be used to spatially sample the field in the vicinity of the catheter. A mathematical model can be 'fit' to the set of measurements made by the 'passive' electrodes to create an estimate or approximation of the impedance field characteristics within the vicinity of the catheter. In some embodiments, the method of 'fitting' can be an optimization method (such as least-squares) or principal component analysis. In some embodiments, the method of fitting can utilize historical information (from the same subject and/or other subjects) as a starting point and can be computationally adapted, e.g., by weighting, to the present measurements. The computational adaptation can be sequentially improved or optimized based on a set of criteria describing the accuracy of the fit, thereby 'learning' the correspondence between the present measurements to prior measurements. Particularly, these sources that are applied to individual electrodes create a point source like field distribution in space. If the source is away from tissue the distortion of this point source like field from tissue is negligible. In proximity to tissue, a narrow region of the tissue will create a dispersion of the field (depending on impedance change at the tissue interface and the current density due to the source at the interface). The current density is the highest closest to the source and thus the tissue region closest to the source produces the most significant portion of the distortion. As this region could be small in size and only come into existence when the source is in close proximity to tissue, the resultant field would still have a structure similar to a point source. This knowledge of the spatial distribution function of the field can be used to estimate the field distribution by fitting a model to a group of sensor measurements as described above. The estimated field can then be used for various localization processes. For example, these could be to estimate the shape of a catheter, position of a catheter with respect to another catheter including locating the position of the source electrode.

For further accuracy in this localization method, the distortion due to tissue can be further reduced by an iterative process used while estimating the field model that can account for the presence of nearby impedance changes (tissue structure). Multiple sources on the catheter or applied to the torso surface can be used for this purpose to decipher the presence and the structure of the tissue interacting with the applied fields.

Further, an application of being able to detect the presence of tissue in the neighborhood of a catheter could be to obtain a measure of the displayed mismatch in localization, showing a separation of the electrode from the anatomy surface, when the electrode is in contact with the anatomy. This measure of anatomy surface to catheter mismatch can be then be corrected for as an adjustment to the localization or the anatomy in the vicinity of the mismatch. In some embodiments, the user can also indicate through software input that a local mismatch exists between localization and anatomy. This user feedback can also be used to setup the adjustment to account for the mismatch.

In other applications, the structure of the neighboring tissue can be determined using the above method and a display of contact (coupling) of a catheter with tissue can be created using this information.

In some embodiments, the localization signals can be used to directly measure the distance between electrodes, such as by measuring the difference in electric potential (voltage) between electrodes when current is sourced into the body through one or more electrodes, conducts through the impedance of the body, e.g., the blood, and returns (is 'sinked') through one or more electrodes.

In some embodiments, the applied source at an electrode can be used to measure the impact of unintended leakage currents from an electrode. The leakage currents could occur due to low input impedance of various electronics attached to the electrode. The leakage current produces a field distribution that can distort the actual measurement of the applied localization field. A point source produces the same field distribution as the leakage current. Thus having a measure of the leakage current (or its impact on a measurement at electrodes) in combination with the field pattern of the distortion estimated by the applied source can be used to correct for the error in the measurement. Alternatively, the applied source can be used to cancel the leakage current by matching the amount of leakage current going out of an electrode. This allows for having reduced computational burden (in turn impacts accuracy) in creating correction for measurements.

Below is a description of a system and/or method to generate and deliver the aforementioned localization signals within the context of the existing electronics of the system 10 as described herein. In addition to the generation, delivery, and measurement of localization signals, system 10 generates and receives ultrasound information, e.g., at 10 MHz, and measures and records biopotential recordings (electrical recordings of heart activity).

System 10 can comprise a single ended switched ultrasound transmitter to be configured to generate a 10 MHz pulse to excite the transducers on the catheter. As an example, closing switches A1 and B1 (as shown in FIG. 10) will allow the 10 MHz pulse to pass through the labeled transducer and return on the common conductor per the diagram above. A simple modification to this single-ended system allows the same transmitter to drive different localization signals (between frequencies of 10 and 100 kHz, preferably between 15 and 40 kHz) between electrodes that neighbor each transducer on a common conduction path. In the diagram above, this would be accomplished by closing switch A1 and any of the other {A2, A3, A4} switches to source and sink the field from each electrode that coincides with the closed switches. Specifically, a wideband transmitter can be configured to transmit either a unipolar high energy high frequency pulse to the ultrasound crystal (standard mode of operation for ranging to the cardiac surface) through a local RF ground or a differential low current low frequency current between two catheter electrodes (alternate mode for measuring distance between electrodes).

Console 5000 can comprise a signal coupling circuit, such as a signal coupling circuit comprising an RC Filter and transformer as shown in FIG. 10. Alternatively or additionally, console 5000 can comprise an alternate signal coupling circuit, configured to attach to the multiplexed conduction path described herein. An appropriate signal coupling path can then be combined for optimally delivering a certain type of signal (e.g., pacing signal coupled based on frequency). This allows for the switching setup to handle a wide variety of signals without needing additional switching hardware.

In some embodiments, ultrasound module 5210 can be configured to detect magnetic signals (e.g. high frequency magnetic signals) from a magnetic field-generating coil of a catheter of the present inventive concepts, such as to determine the location of that catheter (e.g. a location within a chamber of the patient's heart). System 10 can include a wideband generator capable of generating single ended and/or differential wideband and/or narrowband signals, such as signals with a frequency of 1.5 kHZ to 10 MHz, or 10 kHZ to 10 MHz. These drive signals can be of arbitrary complexity and can be configured as ultrasound transmit pulses, magnetic field generators (e.g. high frequency magnetic field generators), and/or differential electric field generators. These drive signals can be provided using the same transmit circuitry of ultrasound module 5210, such as via signal path switching on the output circuitry of ultrasound module 5210. These drive signals can be applied to externally positioned coils and/or antennas ("coils" herein) of system 10 to create an external magnetic field which can be sensed by a coil of a catheter to be localized. Alternatively or additionally, these drive signals can be configured to generate a single ended magnetic field between a remote electrode (e.g. a skin patch of system 10) and a local receiver (e.g. a coil) positioned on the catheter to be localized. Alternatively or additionally, these signals can be configured to generate a single ended magnet field (e.g. a high frequency magnetic field) between a remote electrode of system 10 and a local receiver positioned on the catheter to be localized, and these drive signals can further comprise single ended bursts (e.g. high energy bursts) provided to the ultrasound transducers 1153 (e.g. for ultrasound ranging).

Frequencies used to localize devices within the heart H must be selected to overcome various challenges. Low frequencies (e.g., 1 kHz<x<20 kHz) enable high input impedances which serve to reduce interactions between localized devices. Frequencies in the 1 Hz to 1 KHz range are a part of the biopotential measurements and any external signals applied in this range would impact the reliable measurements of biopotential. However these signals also provide high input impedance advantage and can also be used for localizing devices in a scheme that does not interfere with the biopotential measurement (e.g., pulsing for a short time <5 mSec). Frequencies between 1 kHz to 10 kHz could add additional challenges due to tissue impedance variability. Higher frequencies tend toward a more linear impedance field, making scaling and measurement easier. In some embodiments, higher frequencies are sensed by system amplifiers with a lower input impedance that can result in crosstalk between localized devices. However, interleaving or simultaneously applying low and high frequencies may allow the system 10 (or console 5000) to take advantage of both higher input impedances, linear fields, and adequate sampling rates without diminishing performance. For example, when a piece of electronics is attached to the patient that has different input impedance at low versus high frequency, a correction term can be applied to account for change in localization signals based on the measured differences at the two frequencies. Similarly, the tissue impedance has both a resistive and capacitive term, consequently the field distribution which is dependent on tissue impedance shows a phase variability that depends on the two terms. The influence of the capacitive term changes with frequency, this allows to reduce the impact of the impedance of tissue on field distribution by combining fields at different frequencies. A field distribution with lower complexity improves the ability to localize electrodes with it as described herein. With the scheme of interleaved signals the ratio between high and low frequencies can vary depending upon implementation requirements.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

It is appreciated that certain features of the invention, which are, for clarity, described in the context of separate embodiments, may also be provide in combination in a single embodiment. Conversely, various features of the invention which are, for brevity, described in the context of a single embodiment may also be provided separately or in any suitable sub-combination.

For example, it will be appreciated that all of the features set out in any of the claims (whether independent or dependent) can combined in any given way.

What is claimed is:

1. A method of processing physiological information, comprising:
    providing a processor coupled to a data storage device and providing a plurality of functional elements coupled to the processor and disposed within, on and/or proximal to a body;
    establishing and calibrating a localization coordinate system by processing a first set of signals from a first set of the functional elements using a first localization mode; and
    recalibrating the localization coordinate system by processing a second set of signals from a second set of the functional elements using a second localization mode, wherein the first localization mode is different from the second localization mode.

2. The method of claim 1, wherein the method includes:
    inserting at least one object into at least one of an organ and the body, the at least one object comprising functional elements from the plurality of functional elements.

3. The method of claim 2, wherein the at least one object includes at least one catheter comprising catheter functional elements.

4. The method of claim 2, wherein the at least one catheter comprises a diagnostic catheter.

5. The method of claim 4, further comprising:
    localizing the diagnostic catheter within the localization coordinate system,
    wherein the diagnostic catheter includes at least one of:
        one or more magnetic elements used for magnetic-based localization;
        one or more electrodes used for impedance-based localization; and
        one or more ultrasound elements used for ultrasound-based localization.

6. The method of claim 4, wherein the diagnostic catheter is a cardiac mapping catheter and the catheter functional elements include a plurality of electrodes configured to at least one of sense and record potentials related to at least one of cardiac activity and localization.

7. The method of claim 4, wherein the diagnostic catheter is a basket catheter and the catheter functional elements comprise a basket array of electrodes.

8. The method of claim 4, wherein the diagnostic catheter is a lasso catheter and the catheter functional elements comprise an array of electrodes.

9. The method of claim 4, wherein the diagnostic catheter includes a shaft having a distal end comprising an actuator slidable within a lumen of a sheath to deploy an array of functional elements within the body, and wherein at least one of the shaft, sheath, and actuator include one or more functional elements.

10. The method of claim 9, wherein each of the shaft and the actuator include one or more functional elements in the form of auxiliary electrodes, the method comprising:
    the processor determining relative distance measurements between the auxiliary electrodes on the shaft and the auxiliary electrodes on the actuator.

11. The method of claim 10, further comprising:
    the processor determining a shape of the array of functional elements based on the distance measurements.

12. The method of claim 11, wherein the array of functional elements is a basket array and the processor determines a shape of the basket array.

13. The method of claim 1, wherein the plurality of functional elements comprises external functional elements arranged outside and/or on the body, and wherein the external functional elements include one or more of the first set and/or the second set of functional elements.

14. The method of claim 13, wherein the method includes:
providing at least one wearable garment comprising at least some of the external functional elements, including the one or more of at least one of the first set and second set of functional elements, the wearable garment maintaining at least one of contact, pressure, and position of the external functional elements relative to the body,
wherein the at least one wearable garment takes the form of a vest, suit, shirt, bodysuit, or portion thereof.

15. The method of claim 14, wherein at least one of:
at least some of the external functional elements are removable from the at least one wearable garment, and
at least some of the external functional elements are embedded or disposed within the at least one wearable garment.

16. The method of claim 14, wherein the wearable garment includes at least two different external functional elements, as the one or more of at least one of the first set and the second set of functional elements, chosen from a group consisting of impedance functional elements, magnetic functional elements, and ultrasound functional elements.

17. The method of claim 16, wherein the method includes:
providing patches comprising at least some of the external functional elements, including the one or more of at least one of the first set and the second set of functional elements; and
affixing the patches to a torso of the body.

18. The method of claim 17, wherein one or more of the patches includes at least two different external functional elements, as the one or more of at least one of the first set and the second set of functional elements, chosen from a group consisting of a magnetic functional element, an impedance functional element, and an ultrasound functional element.

19. The method of claim 1, further comprising:
recording physiological data at one or more recording locations of the functional elements and transforming the physiological data into patient information at one or more target locations that are different from the recording locations.

20. The method of claim 19, further comprising:
the processor estimating, at particular cyclic time points of a patient's physiological variations, at least one of transformations and field properties to describe the field.

21. The method of claim 19, further comprising:
applying a transfer matrix to the physiologic data at one or more recording locations to determine patient information at one or more target locations that are different from the recording locations.

22. The method of claim 21, wherein the transfer matrix is a scale matrix and the scale matrix is a measure of a rate of change of a field value.

23. The method of claim 22, wherein calibrating the localization coordinate system includes estimating the scale matrix, including estimating the scale matrix by measuring voltage differences between functional element having a known spacing.

24. The method of claim 23, wherein the functional elements are on a catheter whose dimensions are predetermined.

25. The method of claim 22, further comprising:
localizing one or more of the functional elements relative to the body, wherein the localizing includes estimating a location of functional element by:
measuring a difference in a field value between the functional elements and a location whose position with respect to the body and field value is known; and
multiplying the measured difference by the scale matrix,
wherein the resultant output of multiplying the measured difference by the scale matrix is the position of the sensor with respect to the known location.

* * * * *